US005859230A

United States Patent [19]
Kim et al.

[11] Patent Number: 5,859,230
[45] Date of Patent: Jan. 12, 1999

[54] NON-A/NON-B/NON-C/NON-D/NON-E HEPATITIS AGENTS AND MOLECULAR CLONING THEREOF

[75] Inventors: Jungsuh P. Kim; Gregory R. Reyes; LaVonne Marie Young, all of Palo Alto, Calif.

[73] Assignee: Genelabs Technologies, Inc., Redwood CIty, Calif.

[21] Appl. No.: 611,757

[22] Filed: Mar. 6, 1996

Related U.S. Application Data

[60] Division of Ser. No. 246,985, May 20, 1994, which is a continuation-in-part of Ser. No. 25,396, Feb. 24, 1993, abandoned, which is a continuation-in-part of Ser. No. 922,493, Jul. 30, 1992, abandoned.

[51] Int. Cl.$^6$ .................................................. C07H 21/04
[52] U.S. Cl. ................. 536/24.33; 536/24.3; 536/24.32; 536/23.72
[58] Field of Search ............................... 536/24.3, 24.32, 536/24.33, 23.72

[56] References Cited

U.S. PATENT DOCUMENTS

| | | | |
|---|---|---|---|
| 4,870,026 | 9/1989 | Wands et al. | 436/548 |
| 5,032,511 | 7/1991 | Takahashi et al. | 435/69.1 |
| 5,043,272 | 8/1991 | Hartley | 435/91 |
| 5,077,193 | 12/1991 | Mishiro et al. | 435/5 |
| 5,218,099 | 6/1993 | Reyes et al. | 536/23.72 |
| 5,275,947 | 1/1994 | Arima et al. | 435/252.33 |
| 5,283,171 | 2/1994 | Manos et al. | 435/5 |

FOREIGN PATENT DOCUMENTS

| | | |
|---|---|---|
| 0 318 216 | 5/1989 | European Pat. Off. . |
| 0 363 025 | 4/1990 | European Pat. Off. . |
| WO 90/00597 | 1/1990 | WIPO . |
| WO 91/06562 | 5/1991 | WIPO . |
| WO 91/15603 | 10/1991 | WIPO . |
| WO 94/18217 | 8/1994 | WIPO . |
| WO 95/21922 | 8/1995 | WIPO . |

OTHER PUBLICATIONS

Bradley, D.W., et al., "Posttransfusion Non–A, Non–B Hepatitis: Physicochemical Properties of Two Distinct Agents," *The Journal of Infectious Diseases*, 148(2):254–265 (1983).

Buti, M., et al., "Non–A, Non–B, Non–C, Non–E Acute Hepatitis: Does it Really Exist?" *Journal of the European Association for the Study of the Liver*, in Abstracts Of The 28th Annual Meeting Of The European Association For The Study Of The Liver, 1–4 Sep. 1993, Paris, France. 18(Suppl 1):S25 (1993).

Chan, S.W., et al., "Analysis of a new hepatitis C virus type and its phylogenetic relationship to existing variants," *Journal of General Virology*, 73(5):1131–1141 (1992).

Choo, Q–L., et al., "Isolation of a cDNA Clone Derived from a Blood–Borne Non–A, Non–B Viral Hepatitis Genome," *Science*, 244:359–362 (1989).

Jiang, X., et al., "Norwalk Virus Genome Cloning and Characterization," *Science*, 250:1580–1583 (1990).

Jones, W.F., et al., "The Role of Hepatitis C Virus (HCV) and Hepatitis E Virus (HEV) in Acute Hepatitis: Evidence for a Non–A,B,C,D,E Syndrome," *The American Association for the Study of Liver Diseases*, 16(2 Pt. 2):77A (1992).

Karayiannis, P., et al., "Studies of GB Hepatitis Agent in Tamarins," *Hepatology*, 9(2):186–192 (1989).

Matsui, S.M., et al., "The Isolation and Characterization of a Norwalk Virus–specific cDNA," *J. Clin. Invest.*, 87:1456–1461 (1991).

Matsuura, Y., et al., "Expression of the S–coded Genes of Lymphocytic *Choriomeningitis Arenavirus* using a Baculovirus Vector," *J. Gen Virol.*, 67:1515–1529 (1986).

Overton, H.A., et al., "Identification of the N and $NS_S$ Proteins Coded by the Ambisense S RNA of Punta Toro Phlebovirus Using Monospecific Antisera Raised to Baculovirus Expressed N and $NS_S$ Proteins," *Virology*, 157:338–350 (1987).

Reyes, G.R., et al., "Molecular Biology of Non–A, Non–B Hepatitis Agents: Hepatitis C and Hepatitis E Viruses," *Advances in Virus Research*, 40:57–103 (1991).

Reyes, G.R., "New Strategies for Isolation of Low Abundance Viral and Host cDNAs: Application to Cloning of the Hepatitis E Virus and Analysis of Tissue–Specific Transcription," *Seminars in Liver Disease*, 12(3):289–300 (1992).

Reyes, G.R., et al., "Hepatitis E virus (HEV): epitope mapping and detection of strain variation," in Viral Hepatitus C, D, and E. Proceedings of the International Meeting on Non–A, Non–B Hepatitus, Tokyo, 27–30 Sep. 1989, T. Shikata, et al., eds. Elsevier Science Publishers, Amsterdam, NL. Chapter 43:237–245 (1989).

New England Biolabs, Inc. 1986/87 Product Catalog, pp. 60–62, 1986.

*Primary Examiner*—Michael P. Woodward
*Assistant Examiner*—Brenda G. Brumback
*Attorney, Agent, or Firm*—Gary R. Fabian; Susan T. Evans; Peter J. Dehlinger

[57] ABSTRACT

Polypeptide antigens are disclosed which are immunoreactive with sera from individuals infected with non-A, non-B, non-C, non-D, non-E hepatitis. Also disclosed are corresponding genomic-fragment clones containing polynucleotides encoding the open reading frame sequences for the antigenic polypeptides. The antigens are useful in diagnostic methods for detecting the presence of N-(ABCDE) hepatitis agent infection in primates. The antigens are also useful in vaccine and antibody preparations. Methods are presented for the isolation of entire genomes corresponding to the N-(ABCDE) hepatitis agents.

1 Claim, 5 Drawing Sheets

NON-A/NON-B/NON-C/NON-D/NON-E HEPATITIS AGENTS AND MOLECULAR CLONING THEREOF

This application is a division of U.S. patent application Ser. No. 08/246,985, filed on May 20, 1994, which is a continuation-in-part of U.S. patent application Ser. No. 025,396, filed 24 Feb. 1993, abandoned, herein incorporated by reference, which is a continuation-in-part of U.S. patent application Ser. No. 07/922,493, filed 30 Jul. 1992, abandoned, herein incorporated by reference.

FIELD OF INVENTION

This invention relates to nucleic acid, antigen, and antibody compositions related to nonA/nonB/nonC/nonD/nonE hepatitis (N-(ABCDE)) viral agents.

REFERENCES

Arankalle, V. A., et al., The Lancet, 550 (Mar. 12, 1988).
Ausubel, F. M., et al., *Current Protocols in Molecular Biology*, John Wiley and Sons, Inc., Media Pa.
Beames, et al., Biotechniques 11:378 (1991).
Bradley, D. W., et al., J. Infec. Dis., 148:2 (1983).
Bradley, D. W., et al., J Gen. Virol., 69:1 (1988).
Bradley, D. W. et al., Proc. Nat. Acad. Sci., USA, 84:6277 (1987).
Chomozynski et al, Anal. Biochem. 162:159 (1987).
Crea, R., U.S. Pat. No. 4,888,286, issued Dec. 19, 1989.
Dayhoff, M. O., in *Atlas of Protein Sequence and Structure*, National Biomedical Research Foundation 5:101–110, and Supplement 2 to this volume, pp. 1–10.
Deinhardt, F., et al., J. of Experimental Med., 125:673 (1967).
Dieckmann, C. L., et al., J. Biol. Chem. 260:1513 (1985).
Dienstag, J. L., et al, Sem Liver Disease, 6:67 (1986).
Eaton, M. A. W., et al., U.S. Pat. No. 4,719,180, issued Jan. 12, 1988.
EPO patent application 88310922.5, filed 11/18/88.
Feramisco, J. R., et al., J. Biol. Chem. 257(18):11024 (1982).
Gravelle, C. R. et al., J. Infect. Diseases, 131:167 (1975).
Goeddel, D. V., Methods in Enzymology 185 (1990).
Gubler, U., et al, Gene, 25:263 (1983).
Guthrie, C., and G. R. Fink, Methods in Enzymology 194 (1991).
Harlow, E., et al., *Antibodies: A Laboratory Manual*, Cold Spring Harbor Laboratory Press (1988).
Hieter, P. A., et al., Cell 22:197–207 (1980).
Hopp, T. P., et al., Proc. Natl. Acad. Sci. USA 78:3824–3828 (1981).
Houghton, M., et al., EPO Patent Application No. 88/310922.5, Publication No. 0 318 216 A1, published 31 May 1989.
Houghton, M., et al., EPO Patent Application No. 90/302866.0, Publication No. 0 388 232 A1, published 19 Sept. 1990.
Hunyh, T. V., et al, in *DNA Cloning Techniques: A Practical Approach* (D. Glover, ed.) IRL Press (1985).
Jacob, J. R., et al., in *The Molecular Biology of HCV*, Section 4, pages 387–392 (1991).
Jacob, J. R., et al., Hepatology 10:921–927 (1989).
Jacob, J. R., et al., J. Infect. Dis. 161:1121–1127 (1990).
Kane, M. A., et al., JAMA, 252:3140 (1984).
Karayinnis, P., et al., Hepatology 9:186 (1989).
Kawasaki, E. S., et al., in *PCR Technology: Principles and Applications of DNA Amplification* (H. A. Erlich, ed.) Stockton Press (1989).
Khuroo, M. S., et al., Am. J. Med., 68:818 (1983).
Khuroo, M. S., *Am. J. Med.,* 48:818 (1980).
Kumar, R., et al., AIDS Res. Human Retroviruses 5(3): 345–354 (1989).
Lanford, R. E., et al., In Vitro Cell. Dev. Biol. 25:174–182 (1989).
Maniatis, T., et al. *Molecular Cloning: A Laboratory Manual,* Cold Spring Harbor Laboratory (1982).
Michelle, et al., International Symposium on Viral Hepatitis.
Miller, J. H., *Experiments in Molecular Genetics.*, Cold Spring Harbor Laboratories, Cold Spring Harbor, N.Y. (1972).
Mullis, K. B., U.S. Pat. No. 4,683,202, issued 28 Jul. 1987.
Mullis, K. B., et al., U.S. Pat. No. 4,683,195, issued 28 Jul. 1987.
Osikowicz, G., et al., Clin. Chem. 36:1586 (1990).
Reilly, P. R., et al., *Baculovirus Expression Vectors: A Laboratory Manual* (1992).
Reyes, G., et al, Science, 247:1335 (1990).
Reyes, G., et al., Molecular and Cellular Probes 5:473–481 (1991).
Sanger, et al., Proc. Natl. Acad. Sci. 74:5463 (1977).
Sambrook, J., et al., In *Molecular Cloning: A Laboratory Manual,* Cold Spring Harbor Laboratory Press, Vol. 2 (1989).
Scharf, S. J., et al., Science 233:1076 (1986).
Seto, B., et al., Lancet, 11:941 (1984).
Smith, D. B., et al., Gene 67:31 (1988).
Sreenivasan, M. A., et al., J. Gen. Virol.,65:1005 (1984).
Tabor, E., et al., J. Infect. Dis., 140:789 (1979).
Tam, A., et al., Virology 185:120 (1991).
Wang, A. M., et al. in *PCR Protocols: A Guide to Methods and Applications* (M. A. Innis, et al., eds.) Academic Press (1990).
Valenzuela, P., et al., Nature 298:344 (1982).
Valenzuela, P., et al., in *Hepatitis B,* eds. I. Millman, et al., Plenum Press, pages 225–236 (1984).
Yarbrough, et al., J. Virol. 65:5790 (1991).
Young, R. A. and R. W. Davis, Proc. Natl. Acad. Sci. USA 80, 1194–1198 (1983).
Yoshio, T., et al., U.S. Pat. No. 4,849,350, issued Jul. 18, 1989.

BACKGROUND OF THE INVENTION

Viral hepatitis resulting from a virus other than hepatitis A virus (HAV) and hepatitis B virus (HBV) has been referred to as non-A, non-B hepatitis (NANBH). One of these, known as enterically transmitted NANBH or ET-NANBH, is contracted predominantly in poor-sanitation areas where food and drinking water have been contaminated by fecal matter. The molecular cloning of the causative agent, referred to as the hepatitis E virus (HEV), has recently been described (Reyes et al. (1990); Tam et al.).

A second NANB virus type, known as parenterally transmitted NANBH, or PT-NANBH, is transmitted by parenteral routes, typically by exposure to blood or blood products. Although the rate varies by locale, approximately 10% of transfusions cause PT-NANBH infection, and about half of these go on to a chronic disease state (Dienstag). After anti-HCV testing, HCV seroconversion per unit transfused was decreased to less than 1% among heart surgery patients.

Human sera documented as having produced post-transfusion NANBH in human recipients have been used successfully to produce PT-NANBH infection in chimpanzees (Bradley). RNA isolated from infected chimpanzee sera has been used to construct cDNA libraries in an expression vector for immunoscreening with chronic-state human PT-NANBH serum. This procedure identified a PT-NANBH specific cDNA clone and the viral sequence was then used as a probe to identify a set of overlapping fragments making up 7,300 contiguous basepairs of a PT-NANBH viral agent. The sequenced viral agent has been named the hepatitis C virus (HCV) (for example, the sequence of HCV is presented in EPO patent application 88310922.5, filed Nov. 18, 1988). The full-length sequence (~9,500 nt) of HCV is now available.

Primate transmission studies conducted at the Centers for Disease Control (CDC; Phoenix, Ariz., 1973–1975; 1978–1983) originally provided substantial evidence for the existence of multiple agents of non-A, non-B (NANBH): the primary agents of NANB are now recognized as being associated with infection by HCV and HEV (see above). Later epidemiologic studies conducted at the CDC (Atlanta, Ga., 1989-present) using both research (prototype) and commercial tests for anti-HCV antibody showed that approximately 20% of all community-acquired non-A, non-B hepatitis was also non-C. Further testing of these samples for the presence of HEV (co-owned, co-pending U.S. application Ser. No. 07/372,711, filed 28 Jun. 1989, herein incorporated by reference) have indicated that these cases of community-acquired non-A, non-B, non-C hepatitis were also non-E.

Liver biopsy specimens of Sentinel County patients obtained during the last five years (study of Drs. Miriam Alter and Kris Krawcynski) also showed that many bona fide cases of NANBH were also non-C hepatitis (serologically and RT-PCR (Kawasaki, et al.; Wang, et al.) negative for all markers of HCV infection) developed subsequently into chronic hepatitis with presentation of chronic persistent hepatitis (CPH) or chronic active hepatitis (CAH) consistent with a viral infection.

SUMMARY OF THE INVENTION

The present invention includes the isolation of polypeptide antigens that are immunoreactive with sera infected with a non-A, non-B, non-C, non-D, non-E hepatitis agent. Exemplary embodiments of the present invention include polypeptide antigens where an immunoreactive portion of the antigen is homologous to a polypeptide encoded by a sequence selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106. In addition, a number of other antigenic peptides, useful in the practice of the present invention, are disclosed herein.

Selected antigens of the present are encoded by the nucleic acid sequences presented as SEQ ID NO:11 through SEQ ID NO:16, SEQ ID NO:39 through SEQ ID NO:43, SEQ ID NO:74 through SEQ ID NO:104, and SEQ ID NO:106. These antigens may include heterologous protein sequences (i.e., they may be fused polypeptides), such as sequences encoding β-galactosidase or glutathione-S-transferase.

The present invention also includes an expression system for expressing an antigenic polypeptide having an immunoreactive portion that is immunoreactive with sera infected with non-A, non-B, non-C, non-D, non-E hepatitis agent. The expression system typically includes a host capable of supporting expression of an open reading frame in a selected expression vector, where the selected expression vector includes an open reading frame of sequences encoding an immunoreactive portion of the polypeptide antigens described above. One useful expression vector is lambda gt11: other useful expression vectors are known in the art.

Further, the present invention discloses a method of producing a polypeptide that is immunoreactive with N-(ABCDE) hepatitis sera. Typically, the polypeptide is produced by introducing a selected expression vector containing an open reading frame having sequences encoding the polypeptide antigen into a host capable of supporting expression of an open reading frame in the selected expression vector. The host cell is then cultured under conditions resulting in the expression of the open reading frame sequence. One useful expression vector is lambda gt11 phage vector and the host is *Escherichia coli*.

A further embodiment of the present invention, is a cloning vector capable of expressing under suitable conditions an antigenic polypeptide having an immunoreactive portion that is immunoreactive with sera infected with non-A, non-B, non-C, non-D, non-E hepatitis agent. The antigen is homologous to one of the polypeptides identified by the methods of the present invention and includes those polypeptides encoded by a sequence selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106.

One embodiment of the present invention includes a recombinantly produced N-(ABCDE) hepatitis agent polynucleotide that encodes a polypeptide which is immunoreactive with N-(ABCDE) hepatitis infected sera, where said polynucleotide is selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106. Alternatively, the polynucleotide can correspond to other sequences obtained by the method of the present invention.

Another embodiment of the present invention includes a recombinantly produced N-(ABCDE) hepatitis agent polypeptide which is homologous to a polypeptide encoded by a sequence selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106. Alternately, the recombinant polypeptide can be homologous to other polypeptides antigens obtained by the method of the present invention.

Also included in the invention is a diagnostic kit for use in screening serum containing antibodies specific against N-(ABCDE) hepatitis infection. The kit includes a recombinant N-(ABCDE) hepatitis polypeptide antigen. Exemplary of such polypeptide antigens are polypeptides where an immunoreactive portion of said antigen is homologous to a polypeptide encoded by a sequence selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106. The kit also includes means for detecting the binding of said antibodies to the antigen. One means for detecting the binding of antibodies to the antigen includes a solid support to which the N-(ABCDE) hepatitis polypeptide antigen is attached and a reporter-labelled anti-human antibody, where binding of serum antibodies to the antigen can be detected by binding of the reporter-labelled antibody to said serum antibodies. The can be used in a method of detecting N-(ABCDE) hepatitis agent infection in a primate. In this method the serum from a N-(ABCDE) hepatitis test primate is reacted with a recombinant N-(ABCDE) hepatitis polypeptide antigen and the antigen is examined for the presence of bound antibody.

The present invention also includes a diagnostic kit for use in screening samples containing N-(ABCDE) hepatitis agent nucleic acids. This kit contains primers having sequences specific to N-(ABCDE) hepatitis agents. For example, such sequences can be selected from the group consisting of: SEQ ID NO:11 through SEQ ID NO:16, SEQ ID NO:39 through SEQ ID NO:43, SEQ ID NO:74 through SEQ ID NO:104, and SEQ ID NO:106. The primer may contain reporter moieties for hybridization detection. These primers may be used in a method of detecting N-(ABCDE) hepatitis agent nucleic acid in a primate. In the method a nucleic acid sample is obtained from the primate subject. The sample is combined with at least one primer containing sequences specific to N-(ABCDE) hepatitis agents. The presence of N-(ABCDE) hepatitis agent nucleic acid/primer complexes, formed by hybridization of the N-(ABCDE) hepatitis nucleic acid with primer, is then detected. In addition to hybridization detection using labelled primers, sets of primers can be used to identify target N-(ABCDE) hepatitis agent nucleic acid in a sample by use of polymerase chain reaction amplification. Further, a capture moiety may be included in a primer to allow capture of target sequences to which it binds (e.g., biotin incorporated, avidin capture).

These and other objects and features of the invention will be more fully appreciated when the following detailed description of the invention is read in conjunction with the accompanying drawings.

DETAILED DESCRIPTION OF THE INVENTION

I. Definitions

Figure 1:
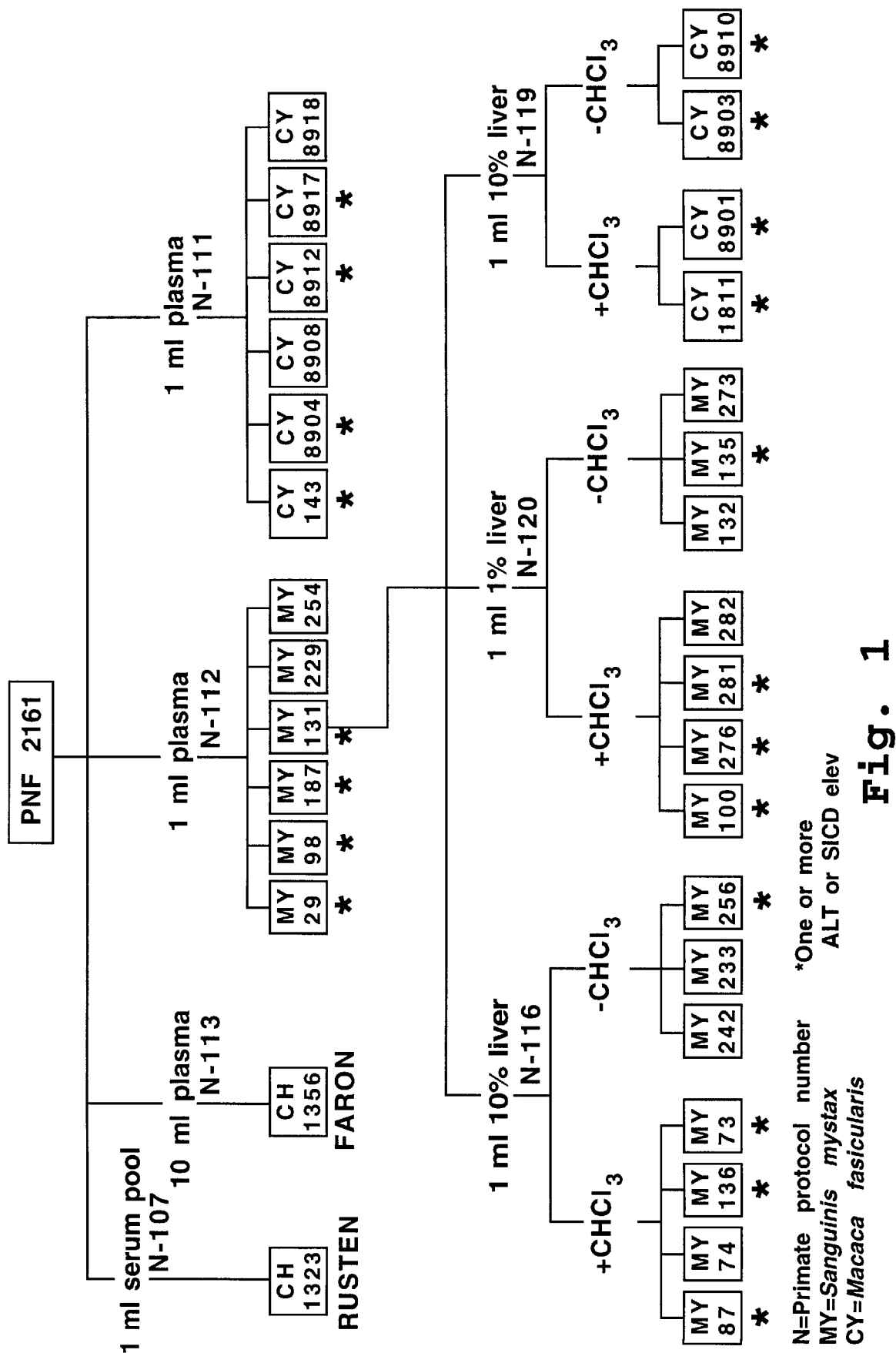
FIG. 1: the use of PNF 2161 plasma in primate transmission studies is diagrammed.

The terms defined below have the following meaning herein:

1. "nonA/nonB/nonC/nonD/nonE hepatitis viral agent N-(ABCDE)" means a virus, virus type, or virus class which (i) is transmissible in primates (e.g., mystax, cynomolgus and marmoset monkeys, chimpanzees, humans), (ii) is serologically distinct from hepatitis A virus (HAV), hepatitis B virus (HBV), hepatitis C virus (HCV), hepatitis D virus, and hepatitis E (HEV) and is characterized by (iii) elevated serum alanine aminotransferase (ALT) levels in an infected primate, and (iv) a viral genome comprising a polynucleotide region that is hybridizable with SEQ ID NO:106 under hybridization conditions that allow at most about 25–30% base pair mismatches.

2. Two nucleic acid fragments are considered to have "homologous" sequences if they are capable of hybridizing to one another (i) under typical hybridization and wash conditions, as described, for example, in Maniatis, et al., pages 320–328, and 382–389, or (ii) using reduced stringency wash conditions that allow at most about 25–30% basepair mismatches, for example: 2×SSC, 0.1% SDS, room temperature twice, 30 minutes each; then 2×SSC, 0.1% SDS, 37° C. once, 30 minutes; then 2×SSC, room temperature twice, 10 minutes each. Preferably, homologous nucleic acid strands contain 15–25% basepair mismatches, even more preferably 5–15% basepair mismatches. These degrees of homology can be selected by using wash conditions of appropriate stringency for identification of clones from gene libraries (or other sources of genetic material), as is well known in the art.

3. Two amino acid sequences or two nucleotide sequences (in an alternative definition for homology between two nucleotide sequences) are considered homologous (as this term is preferably used in this specification) if they have an alignment score of >5 (in standard deviation units) using the program ALIGN with the mutation gap matrix and a gap penalty of 6 or greater (Dayhoff). The two sequences (or parts thereof, preferably at least 35 amino acids in length) are more preferably homologous if their amino acids are greater than or equal to 40% using the ALIGN program mentioned above.

4. A DNA or cDNA fragment is "derived from" N-(ABCDE) viral agents if it has the same or substantially the same basepair sequence as a cloned region of a N-(ABCDE) viral agent genome.

5. A protein is "derived from" N-(ABCDE) viral agents if it is encoded by an open reading frame of a DNA or RNA fragment derived from a N-(ABCDE) viral agent or displays homology as noted under Example 3 above.

6. In the context of-the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

7. In two or more known peptide sequences which are more than about 70% homologous in amino acid sequence, a third amino acid sequence will be internally consistent with the known sequences if each amino acid in the third sequence is identical to at least one of amino acids in the known sequences.

II. N-(ABCDE) Sera.

Originally, infectivity studies of a putative viral agent of human origin, termed "GB," relied on the use of serum derived from acutely infected tamarins (several species) and marmosets (*Callithrix jacchus*) (Deinhardt, et al., 1967).

Studies at the Centers for Disease Control (CDC; Phoenix, Ariz.) involved the use of eleventh passage (P11) "GB" serum which was inoculated intravenously into naive tamarins. All tamarins inoculated with the material developed relatively severe, short-incubation-period hepatitis suggestive of passage or adaptation of this putative human agent to the genus of tamarins or that the agent itself was of non-human (primate) origin.

The eleventh passage "GB" agent is available from the American Type Culture Collection, 12301 Parklawn Dr., Rockville, Md. 20852, as VR-806. This is P11 of the original acute-phase human serum stored in liquid nitrogen.

Two other passages of the GB agent, obtained from Dr. Purcell, National Institutes of Health (NIH), Bethesda, Md. were also used. *S. mystax* (MY 620, MY 661, MY 663, and MY 670) were inoculated intravenously with GB sera by Dr. Purcell. *S. labiatus* (539B, 500, and 41B; Karayinnis, et al., 1989) were inoculated intravenously with GB sera by Professor Thomas and Dr. Karayinnis. All animals developed symptoms of non *C hepatitis.*

The arrival of a serologic test for anti-HCV and the development of an RT-PCR (Kawasaki, et al.; Wang, et al.) for HCV-RNA allowed the identification of several cases of both post-transfusion and sporadic non-HCV hepatitis. Human hepatitis case, PNF-2161, had been followed for at least 60 months, with blood collection every three months during the period following the acute-phase of disease.

Although initially diagnosed as having chronic non-C hepatitis, this individual (PNF 2161) was subsequently discovered to be co-infected with HCV: (i) RT-PCR for the 5' UTR of HCV-RNA showed that HCV was indeed present in this plasma; (ii) further antibody testing showed the presence of anti-HCV antibodies (see Example 1, Table 1). Inoculation of sera and plasma from case PNF-2161 into two chimpanzees, however, showed no evidence of disease due to HCV, except for the development of anti-capsid (C22) antibody in one animal. The other animal showed no ALT elevation or serologic evidence of infection with HCV. The results of inoculations in these two animals indicate that the HCV-variant present in the PNF 2161 serum was highly atypical, in that, in numerous animal studies even low titer inocula containing HCV elicited reproducible hepatitis infection in chimpanzees. These findings indicated the presence of another etiologic agent of PT-NANBH, other than HCV, in the chronic-phase plasma of case PNF-2161.

In view of the inability of the PNF 2161 plasma to transmit HCV infection to chimpanzees and the possible susceptibility of *Sanguinis mystax* (mystax) and cynomologus macaques (cynos) to infection with the GB hepatitis agent, mystax and cynos monkeys were challenged with PNF 2161 plasma. Intravenous inoculation of cynos and mystax with PNF 2161 resulted in obvious elevations of liver enzymes, including serum ALT activity, and histologic correlates of a viral infection (FIG. 1). The latter findings were most obvious in the liver of MY 131, whose liver was then obtained at or near the peak of ALT activity.

Previous studies have indicated that HCV will not infect mystax monkeys. Furthermore, selected animals from these studies showed no serologically markers of HCV infection. To strengthen the argument that PNF 2161 contains an infectious and transmissible agent of presumed viral origin, subpassage studies were performed in both mystax and cynos.

FIG. 1 illustrates serial passage of non-HCV hepatitis in both species of primate and further illustrates that the etiologic agent is chloroform-resistant. In FIG. 1, PNF 2161 is the original non-C serum that was used to inoculate two chimpanzees (CH1323, with 1 ml. of pooled sera, and CH1356, with 10 ml. of plasma), tamarins (*Sanguinis mystax;* MY, with 1 ml. of plasma) and cynos (*Cynomolgus macaques;* CY, with 1 ml. of plasma). These animals were then monitored for elevated ALT or SICD values (Bradley, et al., 1987, op. cit.): elevated values in the animal are indicated by an asterisk. As noted above, MY 131 had very significant elevated ALT values. The liver of MY131 was obtained at or near the peak of ALT activity. A liver homogenate was prepared and diluted. Ten percent and 1% liver solutions were inoculated into *S. mystax* primates. A 1% liver solution was inoculated into cynos primates. For each inoculation the liver was either treated or not treated with chloroform prior to injection. As above, ALT and SICD values were determined for each animal.

Chronic-phase plasma from two other bona fide cases of non-HCV hepatitis were obtained from Sentinel County Study patients JFA-2179 and DEN-2492 (arranged in consultation/collaboration with Dr. Miriam Alter, P.I. of this Sentinel County Study). Ten-ml aliquots of each of these plasma were intravenously inoculated into two separate chimpanzees. As of approximately 100 days post-inoculation (Apr. 13, 1992) neither chimpanzee had shown biochemical (ALT) evidence of liver disease or serologic evidence of infection with HCV. Aliquots of these same plasma were used in transmission studies with *S. mystax.*

In view of the fact that the GB hepatitis agents and the chloroform-resistant agent recovered from the plasma of case PNF-2161 could infect S. mystax, a cross-challenge study was conducted. In FIG. 2, the GB sera had been passed in marmosets (*Callithrix jacchus*); the P11 sera was inoculated intravenously into naive *S. mystax* (MY 88 and MY 190). The P11 sera was also injected into 3 selected animals, MY 73, MY 136, and MY 242. These *S. Mystax* had been infected first with the PNF-2161 derived agent, they were then intravenously inoculated with serum from a marmoset (passage #11; 1.0 ml aliquots of ATCC VR-806 diluted 1:10 in PBS). All three tamarins MY 73, MY 136, and MY 242 developed a clear second bout of non-HCV hepatitis, indicating that either the etiologic agents were different, or that immunoprotection against reinfection by the same agent was absent (that is, no neutralizing antibodies were present in the convalescent sera of tamarins infected with the PNF-2161 agent). Tamarins MY 88 and MY 190 also developed non-C hepatitis.

In addition to the above described sera a number of human N-(ABCDE) sera have also been identified including SCH (Example 1).

Animal transmission and cross-challenge studies of this type indicate the basic methodology used in the identification of new blood-born pathogenic viruses.

III. Isolation of N-(ABCDE) Hepatitis Agent Sequences.

As one approach toward identifying clones containing N-(ABCDE) hepatitis sequences, cDNA and DNA libraries were prepared from infected sera in the expression vector lambda gt11 (Examples 2, 3 and 16). cDNA and DNA sequences were then selected for the expression of peptides which are immunoreactive with N-(ABCDE) hepatitis infected sera. First round screening was typically performed using the same sera that was used to generate the phage library, or, alternatively, a closely related sera. It is also possible to screen with other suspected N-(ABCDE) sera.

Recombinant proteins identified by this approach provide candidates for peptides which can serve as substrates in diagnostic tests. Further, the nucleic acid coding sequences identified by this approach serve as useful hybridization probes for the identification of further N-(ABCDE) hepatitis coding sequences.

The sera described above were used to generate cDNA and DNA libraries in lambda gt11 (Examples 2, 3 and 16). In the method illustrated in Example 2, infected serum was precipitated in 8% PEG without dilution, and the libraries were generated from the resulting pelleted virus. Sera from infected human sources were treated in the same fashion.

As an advantageous alternative to PEG precipitation, ultracentrifugation can be used to pellet particulate agents from infected sera or other biological specimens. To isolate viral particles from which nucleic acids could be extracted, serum, ranging up to 2 ml, was diluted to approximately 10 ml with PBS and was centrifuged for a minimum of 2 hours at 40,000 rpm (approximately 110,000×g) in the Ti70.1 rotor (Beckman Instruments, Fullerton, Calif.) at 4° C. The supernatant was the aspirated and the pellet extracted by standard nucleic acid extraction techniques.

cDNA libraries were generated using random primers in reverse transcription reactions with RNA extracted from pelleted sera as starting material. DNA libraries were generated by proteinase K treatment and SDS lysis of pelleted sera, followed by the addition of Klenow fragment of DNA polymerase and random primers to the nucleic acid. The resulting molecules, cDNA or DNA, were ligated to SISPA (Reyes, et al., (1991)) linker primers and expanded in a non-selective manner, and then cloned into a suitable vector, for example, lambda gt11, for expression and screening of peptide antigens, and the lambda gt10 vector, for hybridization screening.

Lambda gt11 is a particularly useful expression vector which contains a unique EcoRI insertion site 53 base pairs upstream of the translation termination codon of the β-galactosidase gene. Thus, an inserted sequence is expressed as a β-galactosidase fusion protein which contains the N-terminal portion of the β-galactosidase gene product, the heterologous peptide, and optionally the C-terminal region of the β-galacto-sidase peptide (the C-terminal portion being expressed when the heterologous peptide coding sequence does not contain a translation termination codon). This vector also produces a temperature-sensitive repressor (cI857) which causes viral lysogeny at permissive temperatures, e.g., 32° C., and leads to viral lysis at elevated temperatures, e.g., 42° C. Advantages of this vector include: (1) highly efficient recombinant clone generation, (2) ability to select lysogenized host cells on the basis of host-cell growth at permissive, but not non-permissive, temperatures, and (3) high levels of recombinant fusion protein production. Further, since phage containing a heterologous insert produces an inactive β-galactosidase enzyme, phage with inserts are typically identified using a β-galactosidase colored-substrate reaction.

Examples 2, 3 and 16 describe the preparation of a cDNA and DNA library for each of the following N-(ABCDE) hepatitis sera: MY 131, MY 190, MY 620, MY 670, PNF 2161, JFA, SCH and DEN. These libraries were immunoscreened using N-(ABCDE) hepatitis positive human or mystax sera (Examples 4, and 7–11).

A number of lambda gt11 clones were identified which were immunoreactive with at least one of the sera. Immunopositive clones were plaque-purified and their immunoreactivity retested. Also, the immunoreactivity of the clones with pre-inoculum mystax and/or normal human sera was also tested.

These clones were also examined for the "exogenous" nature of the cloned insert sequence. This basic test establishes that the cloned fragment does not represent a portion of the human or other known (e.g. bacterial) genomes. The clone inserts were isolated by EcoRI digestion following polymerase chain reaction amplification. The inserts were purified then radiolabelled and used as hybridization probes against membrane bound normal human DNA, normal mystax DNA and bacterial DNA (control DNAs) (Example 6).

Described below are a number of clones that were (i) immunoreactive with the N-(ABCDE) hepatitis test sera, (ii) exogenous to human, normal, and bacterial genomes, (iii) not immunologically reactive with pre-immune mystax and/ or normal human sera, and (iv) had unique nucleic acid sequences when compared with one another. The latter may indicate the isolation of multiple viruses or the isolation of different immunogenic regions from the same genome. The sequences of these clones are presented in the Sequence Listing. Furthermore, the sequences of the cloned inserts, when searched against the "GENBANK" sequence library, were not found to have significant homology to any known sequences, including those from known hepatitis virus sequences. Other characteristics of a number of the sequenced clones follow here.

The D19 clone (MY 190 DNA source library) also was shown to be exogenous to normal human, tamarin and bacterial DNA. The clone has a large open reading frame (104 bp), in frame with the β-galactosidase gene of the lambda gt11 vector (SEQ ID NO:17). The antigen encoded by D19 was shown to be immunoreactive with 2/9 infected mystax sera.

Clone 17A (JFA DNA source) was shown to be exogenous to normal human and bacterial DNA. The clone has a large open reading frame (590 bp), in frame with the β-galactosidase gene of the lambda gt11 vector (SEQ ID NO:36). The 17A antigen has been expressed as a GST fusion protein and tested immunopositive with JFA serum.

Clone 1A (JFA DNA source) was shown to be exogenous to normal human and bacterial DNA. The clone has a large open reading frame (467 bp), in frame with the β-galactosidase gene of the lambda gt11 vector (SEQ ID NO:37). The antigen encoded by clone 1A has been expressed as a GST fusion protein and tested immunopositive with JFA serum and negative with normal human sera by Western blot analysis.

Some clones have multiple insert sequences as indicated by internal SISPA primers (Example 2): for example, JFA clone 4B11 (SEQ ID NO:38), D12-3 (SEQ ID NO:46), D31-2 (SEQ ID NO:48) and D76 (SEQ ID NO:50) have 3 inserts; and R27 has four inserts (SEQ ID NO:33). In such cases the insert can be (i) fractionated into discrete sequences by restriction enzyme digestion with EcoRI or NotI, or (ii) portions of the insert separately PCR amplified by sequence specific primers. Each resulting individual region of the cloned sequence can be subcloned into, for example, lambda gt11 or pGEX-GLI and immunoscreened as described above. This allows identification of specific regions responsible for the immunoreactivity (see Epitope Mapping, below).

Clone 470-20-1 (PNF2161 cDNA source) was isolated by immunoscreening with the same cloning source. The clone was not reactive with normal human sera. The clone has a large open reading frame (203 base pairs; SEQ ID NO:106), in-frame with the β-galactosidase gene of the lamdba gt11 vector. The clone is exogenous by genomic DNA hybridization analysis and genomic PCR analysis, using human, yeast and $E. coli$ genomic DNAs. The sequence was present in PNF2161 serum as determined by RT-PCR. The sequence was also detected in sucrose density gradient fractions at densities consistent with the sequence banding in association with a virus-like particle.

Further sequences (PNF2161-470-20-1 EXT1; SEQ ID NO:104) adjacent to clone 470-20-1 were obtained by anchor polymerase chain reaction using primers from clone 470-20-1 (Example 7).

IV. Further Characterization of N-(ABCDE) Hepatitis Recombinant Antigens.

A. Screening Recombinant Libraries.

Further candidate N-(ABCDE) hepatitis antigens can be obtained from the libraries of the present invention using the screening methods described above. The libraries described above have been deposited with the American Type Culture Collection, 12301 Parklawn Dr., Rockville, Md. 20852 and have been assigned the following designations: MY 131 cDNA source, ATCC 75273; MY 131 DNA source, ATCC 75270; MY 190 DNA source, ATCC 75284; MY 190 cDNA source; JFA cDNA source, ATCC 75272; JFA DNA source, ATCC 75271; SCH cDNA source, ATCC 75283; SCH DNA source, ATCC 75282; PNF 2161 cDNA source, ATCC 75268; PNF 2161 DNA source, ATCC 75269; DEN cDNA source, ATCC 75417; and DEN DNA source, ATCC 75418. Libraries assigned the following ATCC designations: ATCC 75268, ATCC 75269, ATCC 75270, ATCC 75271, ATCC 75272 and ATCC 75273, were received and accepted by the American Type Culture Collection on Jul. 16, 1992. SK DNA (ATCC 75282) and SK cDNA libraries (ATCC 75283) were received and accepted for deposit by the American Type Culture Collection on Jul. 23, 1992. My 190 DNA source, ATCC No. 75284, was received and accepted by the American Type Culture Collection on Jul. 30, 1992. DEN cDNA (ATCC No. 75417) and DEN DNA (ATCC 75418) libraries were received and accepted for deposit by the American Type Culture Collection on Feb. 24, 1993. The MY 620 cDNA source, MY 620 DNA source, MY 670 cDNA source, MY 670 DNA source and subtracted SCH DNA source libraries are deposited at Genelabs Technologies, Incorporated, 505 Penobscot Drive, Redwood City, Calif. 94063.

In addition to the recombinant libraries generated above, other recombinant libraries from N-(ABCDE) hepatitis sera can likewise be generated and screened as described herein.

B. Epitope Mapping, Cross Hybridization and Isolation of Genomic Sequences.

The antigen-encoding DNA fragment can be subcloned. The subcloned insert can then be fragmented by partial DNase I digestion to generate random fragments or by specific restriction endonuclease digestion to produce specific subfragments. The resulting DNA fragments can be inserted into the lambda gt11 vector and subjected to immunoscreening in order to provide an epitope map of the cloned insert.

In addition, the DNA fragments can be employed as probes in hybridization experiments to identify overlapping N-(ABCDE) hepatitis sequences, and these in turn can be further used as probes to identify a set of contiguous clones. The generation of sets of contiguous clones allows the elucidation of the sequence of a given N-(ABCDE) hepatitis agent's genome.

The following illustrates several approaches for the use of cloned insert-derived DNA to identify clones carrying other N-(ABCDE) hepatitis sequences. The insert of clone JFA-17A was isolated and used as a hybridization probe against the individual cDNA or DNA libraries established in a lambda vector (Example 10, Sections 10D and 10E). Using the clone JFA-17A probe an overlapping clone has been isolated from a library synthesized from the JFA SISPA DNA source: this clone was designated WT54.

The insert of the overlapping clone can be isolated by restriction enzyme digestion of the clone WT54, followed by electrophoretic fractionation and electroelution. The isolated insert is then treated with DNase I to generate random fragments and the resulting digested fragments are inserted into lambda gt11 phage vectors for immunoscreening to yield other immunoreactive regions.

Any of the above-described clone inserts can be used in a similar manner to probe the cDNA and DNA libraries generated in a vector, such as lambda gt10 or "LAMBDA ZAP II". Entire inserts of specific subfragments of any clone may be isolated by polymerase chain reaction or after cleavage with restriction endonucleases. These fragments can be used as radiolabelled probes against any selected library. In particular, the 5' and 3' terminal sequences of the clone inserts are useful as probes to identify additional clones. In addition, the clone inserts can be used to screen other libraries, for example, the D19 clone insert can be used to screen libraries generated from other human N-(ABCDE) hepatitis sera (such as SCH source libraries).

Further, the sequences provided by the 5' end of cloned inserts are useful as sequence specific primers in first-strand cDNA or DNA synthesis reactions (Maniatis et al.; Scharf et al.). For example, specifically primed MY 190 cDNA and DNA libraries can be prepared by using a D19 specific primer on My 190 nucleic acids as a template. The second-strand of the new cDNA is synthesized using RNase H and DNA polymerase I. The above procedures identify or produce DNA/cDNA molecules corresponding to nucleic acid regions that are 5' adjacent to the known clone insert sequences. These newly isolated sequences can in turn be used to identify further flanking sequences, and so on, to identify the sequences composing the entire genome for a given N-(ABCDE) hepatitis agent. As described above, after new N-(ABCDE) hepatitis sequences are isolated, the polynucleotides can be cloned and immunoscreened to identify specific sequences encoding N-(ABCDE) hepatitis antigens.

Such extension clones, containing further sequences of interest, have been obtained for clone PNF 470-20-1 (SEQ ID NO:106): for example, extension clone (PNF2161-470-20-1 EXT1, SEQ ID NO:104; Example 7).

C. Preparation of Antigenic Polypeptides and Antibodies.

The recombinant peptides of the present invention can be purified by standard protein purification procedures which may include differential precipitation, molecular sieve chromatography, ion-exchange chromatography, isoelectric focusing, gel electrophoresis and affinity chromatography. In the case of a fusion protein, such as the β-galactosidase fusion proteins described above, the fused protein can be isolated readily by affinity chromatography, by passing cell lysis material over a solid support having surface-bound anti-β-galactosidase antibody. For example, purification of a β-galactosidase/fusion protein, derived from D19 coding sequences, by affinity chromatography is described in Example 12.

Fusion proteins containing the polypeptide antigens of the present invention fused with the glutathione-S-transferase (Sj26) protein have also been expressed using the pGEX-GLI vector system in *E. coli* JM101 cells (Examples 9D, 9E, and 12). The fused Sj26 protein can be isolated readily by glutathione substrate affinity chromatography (Smith, et al.). Expression and partial purification of the D6, and D19 as GST (sj26) fusion proteins is described in Examples 9C, 9D and 12, and is applicable to any of the other soluble, induced antigens coded by sequences described by the present invention. Insoluble GST (sj26) fusion proteins (such as, the GST fusions containing the JFA-1A and JFA-17A antigens) have been purified by preparative gel electrophoresis.

Also included in the invention is an expression vector, such as the lambda gt11 or pGEX vectors described above, containing N-(ABCDE) antigen coding sequences and expression control elements which allow expression of the coding regions in a suitable host. The control elements generally include a promoter, translation initiation codon, and translation and transcription termination sequences, and an insertion site for introducing the insert into the vector.

The DNA encoding the desired antigenic polypeptide can be cloned into any number of commercially available vectors to generate expression of the polypeptide in the appropriate host system. These systems include: baculovirus expression (Reilly, et al.; Beames, et al.; Pharmigen; Clontech), expression in bacteria (Ausubel, et al.; Clontech), expression in yeast (Goeddel; Guthrie and Fink), expression in mammalian cells (Clontech; Gibco-BRL). These recombinant polypeptide antigens can be expressed as fusion proteins or as native proteins. A number of features can be engineered into the expression vectors, such as leader sequences which promote the secretion of the expressed sequences into culture medium. The recombinantly produced N-(ABCDE) hepatitis polypeptide antigens are typically isolated from lysed cells or culture media. Purification can be carried out by methods known in the art including salt fractionation, ion exchange chromatography, and affinity chromatography. Immunoaffinity chromatography can be employed using antibodies generated based on the N-(ABCDE) hepatitis antigens identified by the methods of the present invention.

The N-(ABCDE) hepatitis polypeptide antigens may also be isolated from N-(ABCDE) hepatitis agent particles (see below).

Antigenic regions of polypeptides are generally relatively small, typically 7 to 10 amino acids in length. Smaller fragments-have been identified as antigenic regions. N-(ABCDE) hepatitis polypeptide antigens are identified as described above. The resulting DNA coding regions can be expressed recombinantly either as fusion proteins or isolated polypeptides. In addition, some amino acid sequences can be conveniently chemically synthesized (Applied Biosystems, Foster City, Calif.). Antigens obtained by any of these methods may be directly used for the generation of antibodies or they may be coupled to appropriate carrier molecules. Many such carriers are known in the art and are commercially available (e.g., Pierce, Rockford, Ill.).

In another aspect, the invention includes specific antibodies directed against the polypeptide antigens of the present invention. Typically, to prepare antibodies, a host animal, such as a rabbit, is immunized with the purified antigen or fused protein antigen. Hybrid, or fused, proteins may be generated using a variety of coding sequence derived from other proteins, such as β-galactosidase or glutathione-S-transferase. The host serum or plasma is collected following an appropriate time interval, and this serum is tested for antibodies specific against the antigen. Example 13 describes the production of rabbit serum antibodies which are specific against the D19 antigens in the Sj26/D19 hybrid protein. These techniques are equally applicable to the other antigens of the present invention.

The gamma globulin fraction or the IgG antibodies of immunized animals can be obtained, for example, by use of saturated ammonium sulfate precipitation or DEAE Sephadex chromatography, or other techniques known to those skilled in the art for producing polyclonal antibodies.

Alternatively, purified antigen or fused antigen protein may be used for producing monoclonal antibodies. Here the spleen or lymphocytes from an immunized animal are removed and immortalized or used to prepare hybridomas by methods known to those skilled in the art. To produce a human-human hybridoma, a human lymphocyte donor is selected. A donor known to be infected with a N-(ABCDE) hepatitis agent may serve as a suitable lymphocyte donor. Lymphocytes can be isolated from a peripheral blood sample. Epstein-Barr virus (EBV) can be used to immortalize human lymphocytes or a human fusion partner can be used to produce human-human hybridomas. Primary in vitro sensitization with viral specific polypeptides can also be used in the generation of human monoclonal antibodies.

Antibodies secreted by the immortalized cells are screened to determine the clones that secrete antibodies of the desired specificity, for example, by using the ELISA or Western blot method (Ausubel et al.).

D. ELISA and Protein Blot Screening.

When N-(ABCDE) antigens are identified, typically through plaque immunoscreening as described above, the antigens can be expressed and purified. The antigens can then be screened rapidly against a large number of suspected N-(ABCDE) hepatitis sera using alternative immunoassays, such as, ELISAs or Protein Blot Assays (i.e., Westerns) employing the isolated antigen peptide. The antigen polypeptides fusion can be isolated as described above, usually by affinity chromatography to the fusion partner such as β-galactosidase or glutathione-S-transferase. Alternatively, the antigen itself can be purified using antibodies generated against it (see below).

A general ELISA assay format is presented in the Materials and Methods section below. Harlow, et al., describe a number of useful techniques for immunoassays and antibody/antigen screening.

The purified antigen polypeptide or fusion polypeptide containing the antigen of interest, is attached to a solid support, for example, a multiwell polystyrene plate. Sera to be tested are diluted and added to the wells. After a period of time sufficient for the binding of antibodies to the bound antigens, the sera are washed out of the wells. A labelled reporter antibody is added to each well along with an appropriate substrate: wells containing antibodies bound to the purified antigen polypeptide or fusion polypeptide containing the antigen are detected by a positive signal.

A typical format for protein blot analysis using the polypeptide antigens of the present invention is presented in Example 15. General protein blotting methods are described by Ausubel, et al. In Example 15, fusion proteins containing the antigens JFA-1A, JFA-17A, D6 and D19 were used to screen a number of sera samples. The results presented in Example 15 demonstrate that several different source N(ABCDE) Hepatitis sera are immunoreactive with these polypeptide antigens.

These results demonstrate that the polypeptide antigens of the present invention can, by these methods, be rapidly screened against panels of N-(ABCDE) hepatitis serum samples.

E. Cell Culture Systems, Animal Models and Isolation of N-(ABCDE) Hepatitis Agents.

N-(ABCDE) hepatitis agents may be propagated in the animal model systems described above. The N-(ABCDE) hepatitis agents described in the present specification have the advantage of being capable of infecting marmoset and cynos monkeys. This provides a convenient and accessible animal model as well as an animal model that discriminates against the propagation of HCV.

Alternatively, primary hepatocytes obtained from infected animals (chimpanzees, baboons, monkeys, or humans) can be cultured in vitro. A serum-free medium, supplemented with growth factors and hormones, has been described which permits the long-term maintenance of differentiated primate hepatocytes (Lanford, et al.; Jacob, et al., 1989, 1990, 1991). In addition to primary hepatocyte cultures, immortalized cultures of infected cells may also be generated. For example, primary liver cultures may be fused to a variety of cells (like HepG2) to provide stable immortalized cell lines. Primary hepatocyte cell cultures may also be immortalized by introduction of oncogenes or genes causing a transformed phenotype. Such oncogenes or genes can be derived from a number of sources known in the art including SV40, human cellular oncogenes and Epstein Barr Virus.

Further, the un-infected primary hepatocytes may be infected by exposing the cells in culture to the N-(ABCDE) hepatitis agents either as partially purified particle preparations (prepared, for example, from infected sera by differential centrifugation and/or molecular sieving) or in infectious sera. These infected cells can then be propagated and the virus passaged by methods known in the art.

In addition to expression of the N-(ABCDE) hepatitis infectious agents, regions of the N-(ABCDE) hepatitis agent genomic information can be introduced by recombinant means into the hepatocyte cells. Such recombinant manipulations allow the individual expression of individual components of the N-(ABCDE) hepatitis agent genomes.

RNA samples can be prepared from infected tissue or, in particular, from infected cell cultures. The RNA samples can be fractionated on gels and transferred to membranes for hybridization analysis using probes derived from the cloned N-(ABCDE) hepatitis sequences.

N-(ABCDE) hepatitis particles may be isolated from infected sera, infected tissue, the above-described cell culture media, or the cultured infected cells by methods known in the art. Such methods include techniques based on size fractionation (i.e., density centrifugation, precipitation, ultracentrifugation), using anionic and/or cationic exchange materials, separation on the basis of hydrophilic properties, and affinity chromatography. During the isolation procedure the N-(ABCDE) hepatitis agents can be identified using the anti-N-(ABCDE) hepatitis antibodies of the present invention or by using hybridization probes based on identified N-(ABCDE) hepatitis agent nucleic acid sequences.

Antibodies directed against the N-(ABCDE) hepatitis agents can be used in purification of N-(ABCDE) hepatitis particles through immunoaffinity chromatography (Harlow, et al.; Pierce). Antibodies directed against N-(ABCDE) hepatitis polypeptides or fusion polypeptides (such as D19) are fixed to solid supports in such a manner that the antibodies maintain their immunoselectivity. To accomplish such attachment of antibodies to solid support bifunctional coupling agents (Pierce; Pharmacia) containing spacer groups are frequently used to retain accessibility of the antigen binding site of the antibody.

N-(ABCDE) hepatitis particles can be further characterized by standard procedures including immunofluorescence microscopy, electron microscopy, Western blot analysis of proteins composing the particles, infection studies in animal and/or cell systems utilizing the partially purified particles, and sedimentation characteristics.

The N-(ABCDE) hepatitis particles can be disrupted to obtain N-(ABCDE) hepatitis genomes. Disruption of the particles can be achieved by, for example, treatment with detergents in the presence of chelating agents. The genomic nucleic acid can then be further characterized. Characterization may include analysis of DNase and RNase sensitivity. The strandedness and conformation (i.e., circular) of the genome can be determined by techniques known in the art, including visualization by electron microscopy and sedimentation characteristics.

Based on hybridization studies to cloned cDNA molecules derived from the N-(ABCDE) hepatitis agents by the method of the present invention, the nature of the genome can be further evaluated. If, for example, a N-(ABCDE) hepatitis genome is RNA, it can be determined from hybridization of the genomic RNA to the cDNA probes whether the genomic RNA is the positive or negative strand.

The isolated genomes also make it possible to sequence the entire genome whether it is segmented or not, and whether it is an RNA or DNA genome (using, for example RT-PCR, chromosome walking techniques, or PCR which utilizes primers from adjacent cloned sequences). Determination of the entire sequence of a N-(ABCDE) hepatitis agent allows genomic organization studies and the comparison of the N-(ABCDE) hepatitis sequences to the coding and regulatory sequences of known viral agents.

F. Screening for Agents Having Anti-N-(ABCDE) Hepatitis Activity.

The use of cell culture and animal model systems for propagation of N-(ABCDE) hepatitis agents provides the ability to screen for anti-hepatitis agents which inhibit the production of infectious N-(ABCDE) hepatitis agents: in particular, drugs that inhibit the replication of N-(ABCDE) hepatitis agents. Cell culture and animal models allow the evaluation of the effect of such anti-hepatitis drugs on normal cellular functions and viability. Potential anti-viral agents (including, for example, small molecules, complex mixtures such as fungal extracts, and anti-sense oligonucleotides) are typically screened for anti-viral activity over a range of anti-viral agent concentrations. The effect on N-(ABCDE) hepatitis agent replication and/or antigen production is then evaluated relative to the effect of the anti-viral agent on normal cellular function (DNA replication, RNA transcription, general protein translation, etc.).

The detection of the N-(ABCDE) hepatitis agent can be accomplished by the methods described in the present specification. For example, antibodies can be generated against the antigens of the present invention and these antibodies used in antibody-based assays (Harlow, et al.) to identify and quantitate N-(ABCDE) hepatitis antigens in cell culture. N-(ABCDE) hepatitis antigens can be quantitated in culture using competition assays: polypeptides encoded by the cloned N-(ABCDE) hepatitis agent sequences can be used in such assays. Typically, a recombinantly produced N-(ABCDE) hepatitis antigenic polypeptide is produced and used to generate a monoclonal or polyclonal antibody. The recombinant N-(ABCDE) hepatitis polypeptide is labelled using a reporter molecule. The inhibition of binding of this labelled polypeptide to its cognate antibody is then evaluated in the presence of samples (e.g., cell culture media or sera) that contain N-(ABCDE) hepatitis antigens. The level of N-(ABCDE) hepatitis antigens in the sample is determined by comparison of levels of inhibition to a standard curve generated using unlabelled recombinant proteins at known concentrations.

The N-(ABCDE) hepatitis sequences of the present invention are particularly useful for the generation of polynucleotide probes/primers that may be used to quantitate the amount of N-(ABCDE) hepatitis nucleic acid sequences produced in a cell culture system. Such quantification can be accomplished in a number of ways. For example, probes labelled with reporter molecules can be used in standard dot-blot hybridizations or competition assays of labelled probes with infected cell nucleic acids. Further, there are a number of methods using the polymerase chain reaction to quantitate target nucleic acid levels in a sample (Osikowicz, et al.).

Neutralizing antibodies can also be identified using the cell culture and animal model systems described above. For example, polyclonal or monoclonal antibodies are generated against the antigens of the present invention. These antibodies are then used to pre-treat sera before infection of cell cultures or animals. The ability of a single antibody or mixtures of antibodies to protect the cell culture or animal from infection is evaluated. For example, in cell culture and animals the absence of viral antigen and/or nucleic acid production serves as a screen. Further in animals, the absence of N-(ABCDE) hepatitis disease symptoms, e.g., elevated ALT values, is also indicative of the presence of neutralizing antibodies.

Alternatively, convalescent sera can be screened for the presence of neutralizing antibodies and then these sera used to identify N-(ABCDE) hepatitis agent antigens that bind with the antibodies. The identified N-(ABCDE) hepatitis antigen is then recombinantly or synthetically produced. The ability of the antigen to generate neutralizing antibodies is tested as above.

After initial screening, the antigen or antigens identified as capable of generating neutralizing antibodies, either singly or in combination, can be used as a vaccine to inoculate test animals. The animals are then challenged with infectious N-(ABCDE) hepatitis agents. Protection from infection indicates the ability of the animals to generate neutralizing antibodies that protect them from infection.

G. Vaccines and Neutralizing Antibodies.

Vaccines can be prepared from one or more of the immunogenic polypeptides identified by the method of the present invention. Homologies between the isolated sequences from N-(ABCDE) hepatitis agents and other known viral proteins may provide information concerning the polypeptides that are likely to be candidates for effective vaccines. In addition, a number of computer programs can be used for to identify likely regions of isolated sequences that encode protein antigenic determinant regions (for example, Hopp, et al.; "ANTIGEN," Intelligenetics, Mountain View, Calif.).

Vaccines containing immunogenic polypeptides as active ingredients are typically prepared as injectables either as solutions or suspensions. Further, the immunogenic polypeptides may be prepared in a solid or lyophilized state that is suitable for resuspension, prior to injection, in an aqueous form. The immunogenic polypeptides may also be emulsified or encapsulated in liposomes. The polypeptides are frequently mixed with pharmaceutically acceptable excipients that are compatible with the polypeptides. Such excipients include, but are not limited to, the following and combinations of the following: saline, water, sugars (such as dextrose and sorbitol), glycerol, alcohols (such as ethanol [EtOH]), and others known in the art. Further, vaccine preparations may contain minor amounts of other auxiliary substances such as wetting agents, emulsifying agents (e.g., detergents), and pH buffering agents. In addition, a number of adjuvants are available which may enhance the effectiveness of vaccine preparations. Examples of such adjuvants include, but are not limited to, the following: the group of related compounds including N-acetyl-muranyl-L-threonyl-D-isoglutamine and N-acetyl-nor-muranyl-L-alanyl-D-isoglutamine and aluminum hydroxide.

The immunogenic polypeptides used in the vaccines of the present invention may be recombinant, synthetic or isolated from, for example, attenuated N-(ABCDE) hepatitis agent particles. The polypeptides are commonly formulated into vaccines in neutral or salt forms. Pharmaceutically acceptable organic and inorganic salts are well known in the art.

N-(ABCDE) hepatitis vaccines are parenterally administered, typically by subcutaneous or intramuscular injection. Other possible formulations include oral and suppository formulations. Oral formulations commonly employ excipients (e.g., pharmaceutical grade sugars, saccharine, cellulose, and the like) and usually contain within 10–98% immunogenic polypeptide. Oral compositions take the form of pills, capsules, tablets, solutions, suspensions, powders, etc., and may be formulated to allow sustained or longterm release. Suppository formulations use traditional binders and carriers and typically contain between 0.1% and 10% of the immunogenic polypeptide.

In view of the above information, multivalent vaccines against N-(ABCDE) hepatitis agents can be generated which are composed of one or more structural or non-structural viral-agent protein(s). These vaccines can contain recombinantly prepared N-(ABCDE) hepatitis agent polypeptides and/or polypeptides isolated from N-(ABCDE) hepatitis agent virions. In addition, it may be possible to prepare vaccines, which confer protection against N-(ABCDE) hepatitis infection through the use of inactivated N-(ABCDE) hepatitis agents. Such inactivation might be achieved by preparation of viral lysates followed by treatment of the lysates with appropriate organic solvents, detergents or formalin.

Vaccines may also be prepared from attenuated N-(ABCDE) hepatitis agent strains. Such attenuated N-(ABCDE) hepatitis agents may be obtained utilizing the above described cell culture and/or animal model systems. Typically, attenuated strains are isolated after multiple passages in vitro or in vivo. Detection of attenuated strains is accomplished by methods known in the art. One method for detecting attenuated N-(ABCDE) hepatitis agents is the use of antibody probes against N-(ABCDE) hepatitis antigens, sequence-specific hybridization probes, or amplification with sequence-specific primers to screening in vivo or in vitro cultures.

Alternatively, or in addition to the above methods, attenuated N-(ABCDE) hepatitis strains may be constructed based on the genomic information that can be obtained from the information presented in the present specification. Typically, a region of the infectious agent genome that encodes, for example, a polypeptide that is related to viral pathogenesis can be deleted. The deletion should not interfere with viral replication. Further, the recombinant attenuated N-(ABCDE) hepatitis agent construct allows the expression of an epitope or epitopes that are capable of giving rise to neutralizing antibodies against the N-(ABCDE) hepatitis agent. The genome of the attenuated N-(ABCDE) hepatitis agent is then used to transform cells and the cells grown under conditions that allow viral replication. Such attenuated strains are useful not only as vaccines, but also as production sources of viral antigens and/or N-(ABCDE) hepatitis particles.

Hybrid particle immunogens that contain N-(ABCDE) hepatitis epitopes can also be generated. The immunogenicity of N-(ABCDE) hepatitis epitopes may be enhanced by expressing the epitope in a eucaryotic systems (e.g., mammalian or yeast systems) where the epitope is fused or assembled with known particle forming proteins. One such protein is the hepatitis B surface antigen. Recombinant constructs where the N-(ABCDE) hepatitis epitope is directly linked to coding sequence for the particle forming protein will produce hybrid proteins that are immunogenic with respect to the N-(ABCDE) hepatitis epitope and the particle forming protein. Alternatively, selected portions of the particle-forming protein coding sequence, which are not involved in particle formation, may be replaced with coding sequences corresponding to N-(ABCDE) hepatitis epitopes. For example, regions of specific immunoreactivity to the particle-forming protein can be replaced by N-(ABCDE) hepatitis epitope sequences.

The hepatitis B surface antigen has been shown to be expressed and assembled into particles in the yeast *Saccharomyces cerevisiea* and in mammalian cells (Valenzuela, et al., 1982 and 1984; Michelle, et al.). These particles have been shown to have enhanced immunoreactivity. Formation of these particles using hybrid proteins, i.e., recombinant constructs with heterologous viral sequences, has been previously disclosed (EPO 175,261, published Mar. 26, 1986). Such hybrid particles containing N-(ABCDE) hepatitis epitopes may also be useful in vaccine applications.

The vaccines of the present invention are administered in dosages compatible with the method of formulation, and in such amounts that will be pharmacologically effective for prophylactic or therapeutic treatments. The quantity of immunogen administered depends on the subject being treated, the capacity of the treatment subject's immune system for antibody synthesis, and the desired level of protection. The amounts to be administered are usually determined by the administering health care professional.

The N-(ABCDE) hepatitis vaccines of the present invention can be administered in single or multiple doses. Dosage regimens are also determined relative to the treatment subject's needs and tolerances. In addition to the N-(ABCDE) hepatitis immunogenic polypeptides, vaccine formulations may be administered in conjunction with other immuno-regulatory agents, such as immunoglobins.

H. Synthetic Peptides.

When the coding sequences of N-(ABCDE) hepatitis polypeptide antigens are determined synthetic peptides can be generated which correspond to these polypeptides. Synthetic peptides can be commercially synthesized or prepared using standard methods and apparatus in the art (Applied Biosystems, Foster City, Calif.).

Alternatively, oligonucleotide sequences encoding peptides can be either synthesized directly by standard methods of oligonucleotide synthesis, or, in the case of large coding sequences, synthesized by a series of cloning steps involving a tandem array of multiple oligonucleotide fragments corresponding to the coding sequence (Crea; Yoshio et al.; Eaton et al.). Oligonucleotide coding sequences can be expressed by standard recombinant procedures (Maniatis et al.; Ausubel et al.).

V. Utility

A. Immunoassays for N-(ABCDE) Hepatitis Agents.

One utility for the antigens obtained by the methods of the present invention is their use as diagnostic agents for hepatitis antibodies present in N-(ABCDE) sera, thereby indicating current or past infections in the individual; in particular, D19, Clone 17A, Clone 1A. The antigens of the present invention can be used singly, or in combination with each other, in order to detect single or multiple N-(ABCDE) hepatitis agents.

In one diagnostic configuration, test serum is reacted with a solid phase reagent having a surface-bound antigen obtained by the methods of the present invention, e.g., the D19 antigen. After binding anti-N-(ABCDE) hepatitis antibody to the reagent and removing unbound serum components by washing, the reagent is reacted with reporter-labelled anti-human antibody to bind reporter to the reagent in proportion to the amount of bound anti-N-(ABCDE) hepatitis antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group.

In a second diagnostic configuration, known as a homogeneous assay, antibody binding to a solid support produces some change in the reaction medium which can be directly detected in the medium. Known general types of homogeneous assays proposed heretofore include (a) spin-labelled reporters, where antibody binding to the antigen is detected by a change in reported mobility (broadening of the spin splitting peaks), (b) fluorescent reporters, where binding is detected by a change in fluorescence efficiency, (c) enzyme reporters, where antibody binding effects enzyme/substrate interactions, and (d) liposome-bound reporters, where binding leads to liposome lysis and release of encapsulated reporter. The adaptation of these methods to the protein antigen of the present invention follows conventional methods for preparing homogeneous assay reagents.

In each of the assays described above, the assay method involves reacting the serum from a test individual with the protein antigen and examining the antigen for the presence of bound antibody. The examining may involve attaching a labelled anti-human antibody to the antibody being examined (for example from acute, chronic or convalescent phase) and measuring the amount of reporter bound to the solid support, as in the first method, or may involve observing the effect of antibody binding on a homogeneous assay reagent, as in the second method.

Also forming part of the invention is an assay system or kit for carrying out the assay method just described. The kit generally includes a support with surface-bound recombinant N-(ABCDE) hepatitis antigen (e.g., the D19 antigen, as above), and a reporter-labelled anti-human antibody for detecting surface-bound anti-N-(ABCDE) antigen antibody.

A third diagnostic configuration involves use of the anti-N-(ABCDE) hepatitis antibodies capable of detecting N-(ABCDE) hepatitis specific antigens. The N-(ABCDE) hepatitis antigens may be detected, for example, using an antigen capture assay where N-(ABCDE) hepatitis antigens present in candidate serum samples are reacted with a N-(ABCDE) hepatitis specific monoclonal or polyclonal antibody. The antibody is bound to a solid substrate and the antigen is then detected by a second, different labelled anti-N-(ABCDE) hepatitis antibody. Antibodies can be prepared, utilizing the peptides of the present invention, by standard methods. Antibodies that are substantially free of serum proteins which may affect reactivity can be generated (e.g., affinity purification (Harlow et al.)).

B. Hybridization Assays for N-(ABCDE) Hepatitis Agents.

One utility for the nucleic acid sequences obtained by the methods of the present invention is their use as diagnostic agents for hepatitis agent sequences present in N-(ABCDE) sera, thereby indicating infection in the individual. Primers and/or probes derived from the coding sequences of the present invention, in particular, D19, Clone 17A, Clone 1A, and Clone 470-20-1 can be used singly, or in combination with each other, in order to detect single or multiple N-(ABCDE) hepatitis agents.

In one diagnostic configuration, test serum is reacted under PCR or RT-PCR conditions using primers derived from, for example, 470-20-1 sequences. The presence of a N-(ABCDE) hepatitis agent, in the serum used in the amplification reaction, can be detected by specific amplification of the sequences targeted by the primers. Example 14 describes the use of polymerase chain amplification reactions, employing primers derived from the clones of the present invention, to screen different source material. The results of these amplification reactions demonstrate the ability of primers derived from the clones of the present invention (for example, 470-20-1), to detect homologous sequences by amplification reactions employing a variety of different source templates. The amplification reactions in Example 14 included use of nucleic acids obtained directly from sera samples as template material.

Alternatively, probes can be derived from the N-(ABCDE) sequences of the present invention. These probes can then be labelled and used as hybridization probes against nucleic acids obtained from test serum or tissue samples. The probes can be labelled using a variety of reporter molecules and detected accordingly: for example, radioactive isotopic labelling and chemiluminescent detection reporter systems (Tropix, Bedford, Mass.).

Also forming part of the invention is assay systems or kits for carrying out the amplification/-hybridization assay methods just described. Such kits generally include either specific primers for use in amplification reactions or hybridization probes.

C. Therapeutic Uses.

As discussed above, the N-(ABCDE) hepatitis antigens of the present invention can be used in vaccine preparation.

Further, antibodies generated against the polypeptide antigens of the present invention can be used for passive immunotherapy. The anti-N-(ABCDE) hepatitis antibodies of the invention can be used as a means of enhancing an anti-N-(ABCDE) hepatitis immune response since antibody-virus complexes are recognized by macrophages. The antibodies can be administered in amounts similar to those used for other therapeutic administrations of antibody. For example, pooled gamma globulin is administered at 0.02–0.1 ml/lb body weight during the early incubation of other viral diseases such as rabies, measles and hepatitis B to interfere with viral entry into cells. Thus, antibodies reactive with the N-(ABCDE) hepatitis antigens can be passively administered alone or in conjunction with another anti-viral agent to a host infected with a N-(ABCDE) hepatitis agent to enhance the immune response and/or the effectiveness of an antiviral drug.

The following examples illustrate, but in no way are intended to limit the present invention.

Materials and Methods

*E. coli* DNA polymerase I (Klenow fragment) was obtained from Boehringer Mannheim Biochemicals (Indianapolis, Ind.). T4 DNA ligase and T4 DNA polymerase were obtained from New England Biolabs (Beverly, Mass.); Nitrocellulose filters were obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased from commercial suppliers. cDNA synthesis kit and random priming labeling kits were obtained from Boehringer-Mannheim Biochemical (BMB, Indianapolis, Ind.) or GIBCO/BRL (Gaithersburg, Md.).

Standard molecular biology and cloning techniques were performed essentially as previously described in Ausubel, et al., Sambrook, et al., and Maniatis, et al.

Common manipulations involved in polyclonal and monoclonal antibody work, including antibody purification from sera, were performed by standard procedures (Harlow, et al.). Pierce or Promega (Madison, Wis.) were sources of many antibody reagents.

General ELISA Protocol for Detection of Antibodies.

Polystyrene 96 well plates Immulon II (PGC) were coated with 5 μg/mL (100 μL per well) antigen in 0.1M carb/bicarbonate buffer, pH 9.5. Plates are sealed with parafilm and stored at 4° C. overnight.

Plates are aspirated and blocked with 300 uL 10% NGS and incubated at 37° C. for 1 hr.

Plates were washed 5 times with PBS 0.5% "TWEEN-20".

Antisera were diluted in 0.1M PBS, pH 7.2. The desired dilution(s) of antisera (0.1 mL) were added to each well and the plate incubated 1 hours at 37° C. The plates was then washed 5 times with PBS 0.5% "TWEEN-20".

Horseradish peroxidase (HRP) conjugated goat anti-human antiserum (Cappel) was diluted 1/5,000 in PBS. 0.1 mL of this solution was added to each well. The plate was incubated 30 min at 37° C., then washed 5 times with PBS.

Sigma ABTS (substrate) was prepared just prior to addition to the plate.

The reagent consists of 50 mL 0.05M citric acid, pH 4.2, 0.078 mL 30% hydrogen peroxide solution and 15 mg ABTS. 0.1 mL of the substrate was added to each well, then incubated for 30 min at room temperature. The reaction was stopped with the addition of 0.050 mL 5% SDS (w/v). The relative absorbance is determined at 410 nm.

EXAMPLE 1

CHARACTERIZATION OF N-(ABCDE) SERA

The sera samples in the Table 1 were tested in standard ELISA assays using a number of known hepatitis antigens including the C100 Abbott test kit antigen (Abbott Laboratories, N. Chicago, Ill.) and HCV and HEV individual antigens. The 409-1-1 and the 33u antigens are from HCV NS3, antigen 36 from HCV NS5. All HCV epitopes, except antigen 36, were expressed as a fusion protein of glutathione-S-transferase (Smith, et al.). The original PNF 2161 inoculum was positive with HCV antigens. However, the My131 inoculated with PNF2161 tested negative for the presence of HCV by the RT-PCR assay, PCR using non-coding region HCV primers, and by ELISA with HCV antigens.

The presence of HCV nucleic acid was also tested using a reverse transcription polymerase chain reaction (Kawasaki, et al.; Wang, et al.).

The sera PNF 2161, My 131, My 190, JFA, SCH, DEN and STA all test negative for the presence of antigens to HAV and HBV virus.

TABLE 1

| Serum/Plasma | Source | Source of Infection* | HCV:RT-PCR | | Anti-HCV | | | | |
|---|---|---|---|---|---|---|---|---|---|
| | | | NC | NS3 | Capsid | C33/C33u | C100 | 409-1-1 | 36 |
| PNF2161** | CDC | C, TX | + | – | + | + | + | + | + |
| My131 (PNF2161) | CDC | A | – | ND | – | – | – | – | – |
| JFA⁻ | CDC | C, UK | – | – | – | – | – | – | – |
| DEN⁻ | CDC | C, UK | – | – | – | – | – | – | – |
| My190 (GB) | CDC | A | – | ND | – | – | – | – | – |
| SCH⁻ | NIH | A/R, TX | – | ND | – | – | – | – | – |
| STA | NIH | A/C, TX | – | ND | – | – | – | – | – |

ND = not determined
* = Hepatitis Source: C: chronic hepatitis A: acute hepatitis R: resolved TX: transfusion UK: unknown
** = ANTI-HEV negative in ELISA assays using 3-2 (M) 4-2 (M), 6-1-4 antigens, and 4-2 (B) (Yarbrough, et al.).

The HCV epitopes have been disclosed in Houghten, et al., (C-100) and in co-owned, co-pending, U.S. application Ser. No. 07/594,854, filed 9 Oct. 1990, herein incorporated by reference.

EXAMPLE 2

CONSTRUCTION OF cDNA LIBRARIES

One milliliter of each undiluted serum (JFA, PNF 2161, SCH, My 131, My 190, and DEN) was precipitated by the addition of PEG (MW 6,000) to 8% and centrifugation at 12K, for 15 minutes in a microfuge, at 4° C.

Alternatively, one milliliter of each undiluted serum (My 620 and My 670) was pelleted by centrifugation at 40,000 rpm in a type 70.1 rotor for 2 hours at 4° C.

Each resulting pellet (by either of the above methods) was extracted for RNA and DNA. Half of the nucleic acids were converted to cDNA with random primer and reverse transcriptase after denaturation. The other half of each was converted to DNA with random primer and Klenow.

A. Isolation of RNA from Sera.

RNA was extracted from each resulting serum pellet essentially as described by Chomozynski. The pellet was treated with a solution containing 4M guanidine isothiocyanate, 0.18% 2- mercaptoethanol, and 0.5% sarcosyl. The treated pellet was extracted several times with acidic phenol-chloroform alcohol, and the RNA was precipitated with ethanol. This solution was held at –70° C. for approximately 10 minutes and then spun in a microfuge at 4° C. for 10 minutes. The resulting pellet was resuspended in 100 $\mu$l of DEPC-treated (diethyl pyrocarbonate) water, and 10 $\mu$l of NaOAc, pH=5.2, two volumes of 100% ethanol and one volume of 100% isopropanol were added to the solution. The solution was held at –70° C. for at least 10 minutes. The RNA pellet was recovered by centrifugation in a microfuge at 12,000×g for 15 minutes at 5° C. The pellet was washed in 70% ethanol and dried under vacuum.

B. Synthesis of cDNA (i) First Strand Synthesis

The synthesis of cDNA-molecules was accomplished as follows. The above described RNA preparations were transcribed into cDNA, according to the method of Gubler et al. using random nucleotide hexamer primers (cDNA Synthesis Kit, BMB, Indianapolis, Ind. or GIBCO/BRL, Gaithersburg, Md.).

For nucleic acid samples derived from sera JFA, PNF 2161 and SCH, the nucleic acid pellet was treated with RNase-free DNase I (Ausubel, et al.) prior to first strand synthesis; My 131 and My 190 sera were not treated with DNase.

After the second-strand cDNA synthesis, T4 DNA polymerase was added to the mixture to maximize the number of blunt-ends of cDNA molecules. The reaction mixture was incubated at room temperature for 10 minutes. The reaction mixture was extracted with phenol/chloroform and chloroform isoamyl alcohol.

The cDNA was precipitated by the addition of two volumes of 100% ethanol and chilling at –70° C. for 15 minutes. The cDNA was collected by centrifugation, the pellet washed with 70% ethanol and dried under vacuum.

C. Amplification of the Double Stranded cDNA Molecules.

The cDNA pellet was resuspended in 12 $\mu$l distilled water. To the resuspended cDNA molecules the following components were added: 5 $\mu$l phosphorylated linkers (Linker AB, a double strand linker comprised of SEQ ID NO:44 and SEQ ID NO:45, where SEQ ID NO:45 is in a 3' to 5' orientation relative to SEQ ID NO:44—as a partially complementary sequence to SEQ ID NO:44), 2 $\mu$l 10×ligation buffer (0.66M Tris.Cl pH=7.6, 50 mM MgCl$_2$, 50 mM DTT, 10 mM ATP) and 1 $\mu$l T4 DNA ligase. Typically, the cDNA and linker were mixed at a 1:100 molar ratio in the presence of 0.3 to 0.6 Weiss units of T4 DNA ligase. The reaction was incubated at 14° C. overnight. The following morning the reaction was incubated at 70° C. for three minutes to inactivate the ligase.

To 100 $\mu$l of 10 mM Tris-Cl buffer, pH 8.3, containing 1.5 mM MgCl$_2$ and 50 mM KCl (Buffer A) was added about 1×10–3 $\mu$g of the linker-ligated cDNA, 2 $\mu$M of a primer having the sequence shown as SEQ ID NO:44, 200 $\mu$M each of dATP, dCTP, dGTP, and dTTP, and 2.5 units of Thermus aquaticus DNA polymerase (Taq polymerase). The reaction mixture was heated to 94° C. for 30 sec for denaturation, allowed to cool to 50° C. for 30 sec for primer annealing, and then heated to 72° C. for 0.5–3 minutes to allow for primer extension by Taq polymerase. The amplification reaction, involving successive heating, cooling, and polymerase reaction, was repeated an additional 25–40 times with the aid of a Perkin-Elmer Cetus DNA thermal cycler (Mullis; Mullis, et al.; Reyes, et al., 1991).

After the amplification reactions, the solution was then phenol/chloroform, chloroform/isoamyl alcohol extracted and precipitated with two volumes of ethanol. The resulting amplified cDNA pellets were resuspended in 20 $\mu$l TE (pH=7.5).

D. Cloning of the cDNA into Lambda Vectors.

The linkers used in the construction of the cDNAs contained an EcoRI site which allowed for direct insertion of the amplified cDNAs into lambda gt11 vectors (Promega, Madison, Wis. or Stratagene, La Jolla, Calif.). Lambda vectors were purchased from the manufacturer (Promega) which were already digested with EcoRI and treated with bacterial alkaline phosphatase, to remove the 5' phosphate and prevent self-ligation of the vector.

The EcoRI-digested cDNA preparations were ligated into lambda gt11 (Promega). The conditions of the ligation reactions were as follows: 1 µl vector DNA (Promega, 0.5 mg/ml); 0.5 or 3 µl of insert cDNA; 0.5 µl 10×ligation buffer (0.5M Tris-HCl, pH=7.8; 0.1M $MgCl_2$; 0.2M DTT; 10 mM ATP; 0.5 g/ml bovine serum albumin (BSA)), 0.5 µl T4 DNA ligase (New England Biolabs) and distilled water to a final reaction volume of 5 µl.

The ligation reaction tubes were placed at 14° C. overnight (12–18 hours). The ligated cDNA was packaged the following morning by standard procedures using a lambda DNA packaging system (GIGAPAK, Stratagene, LaJolla, Calif.), and then plated at various dilutions to determine the titer. A standard X-gal blue/white assay was used to determine recombinant frequency of the libraries (Miller; Maniatis et al.).

Percent recombination in each library was also determined as follows. A number of random clones were selected and corresponding phage DNA isolated. Polymerase chain reaction (Mullis; Mullis, et al.) was then performed using isolated phage DNA as template and lambda DNA sequences, derived from lambda sequences flanking the EcoRI insert site for the cDNA molecules, as primers. The presence or absence of insert was evident from gel analysis of the polymerase chain reaction products.

E. cDNA Libraries Generated cDNA-insert phage libraries were generated from sera samples My 131, My 190, My 620, My 670, DEN, SCH, JFA and PNF 2161.

F. Deposit of cDNA Libraries.

The cDNA-insert phage libraries generated from sera samples My 131, My 190, DEN, SCH, JFA and PNF 2161 have been deposited with the American Type Culture Collection, 12301 Parklawn Dr., Rockville, Md. 20852, and have been assigned the following deposit designations: MY 131 cDNA source, ATCC 75273; PNF 2161 cDNA source, ATCC 75268; JFA cDNA source 75272; SCH cDNA source, ATCC 75283; DEN cDNA source, ATCC 75417; and MY 190, cDNA source, to be assigned. The cDNA-insert phage libraries generated from sera samples My 620 and My 670 can be obtained from Genelabs Technologies, Inc., 505 Penobscot Dr., Redwood City, Calif. 94063.

EXAMPLE 3

CONSTRUCTION OF DNA LIBRARIES

A. My 131 and My 190 Libraries.

(i) Isolation of Nucleic Acids.

Each sera, My 131 and My 190, was pelleted as described above. The resulting pellet was resuspended in 0.1M NaCl, 50 mM Tris, pH 8, 1 mM EDTA, 0.5% SDS and treated with Proteinase K at a final concentration of 1 mg/ml. Nucleic acids were precipitated, after phenol/chloroform and chloroform/isoamyl alcohol extractions, by the addition of two volumes of ice-cold ethanol. This solution was held at −70° C. for approximately 10 minutes and then spun in a microfuge at 4° C. for 10 minutes.

The resulting pellet was resuspended in 100 µl of sterile TE (Maniatis, et al.). To this solution 10 µl of NaOAc, pH=5.2, and two volumes of 100% ethanol were added. The solution was held at −70° C. for at least 10 minutes. The nucleic acid pellet was recovered by centrifugation in a microfuge at 12,000×g for 15 minutes at 5° C. The pellet was washed in 70% ethanol, dried under vacuum, and resuspended in a minimum volume of TE.

(ii) Random Primer Synthesis From DNA Templates.

The isolated nucleic acid was used as template for random primed DNA synthesis reactions. 2 µl of 10×Klenow buffer (500 mM Tris-HCl, pH 7.5, 100 mM $MgCl_2$, 10 mM DTT), 2 µl of (0.5 mg/ml) hexanucleotide primer mixture (Boehringer Mannheim). 2 µl of a 1.25 mM dNTP mixture and distilled water were added to the TE-resuspended nucleic acid to a final volume of 9 ul. The reaction mixture was heated to 95° C. for 5 minutes to denature the DNA, and 1 µl of Klenow (1.5 u) was added to start the reaction upon cooling of the mixture. The reaction was placed at 37° C. and typically carried out for 30 minutes. The reacted was stopped by the heat-inactivation of the Klenow enzyme at 65° C. for 10 minutes. Blunt ends for the DNA molecules were generated by the treatment with the DNA polymerase as described previously.

Nucleic acids were precipitated and resuspended as described above.

(iii) Amplification and Cloning.

The random primed DNA mixture was ligated to linkers, PCR amplified and cloned in lambda gt11 vectors as described in Example 2.

B. JFA, PNF 2161, SCH, DEN, My 620 and My 670 Libraries.

DNA libraries from sera JFA, PNF 2161, SCH, DEN, My 620 and My 670 were prepared essentially as described for the My 131 and My 190 libraries, except that, prior to random primer DNA synthesis, the nucleic acid samples were treated with DNase-free RNase (Boehringer Mannheim) (Ausubel, et al.; Maniatis, et al.) for JFA and PNF2161 libraries.

Further, for the preparation of DNA libraries from My 620 and My 670, initial pelleting of the sera was carried out as described in Example 2, i.e., pelleting by centrifugation instead of PEG precipitation.

C. Subtracted SCH DNA Libraries.

(i) Isolation of Nucleic Acids.

One ml of SCH human serum was pelleted by ultracentrifugation at 210,000 g for 4 hours at 4° C. The resulting pellet was resuspended, treated, extracted and precipitated as described above.

(ii) Random Primer Synthesis From DNA Templates.

The isolated nucleic acid was used as template for random primed DNA synthesis reactions, as described above. The samples were precipitated and resuspended as described above.

(iii) Amplification.

Normal human serum DNA was extracted from a healthy donor from Stanford blood bank, subjected to random priming and then ligated to C/D primer linker (nucleotide sequences of oligonucleotide C: SEQ ID NO:8 and of oligonucleotide D: SEQ ID NO:19). The resulting normal human DNA was 5' end-labelled with biotin using a biotinylated primer (at 1 µM) in a polymerase chain reaction. The reaction was performed as described in Example 2C except that the mixture was heated to 94° C. for one minute, allowed to cool to 50° C. for two minutes, and then heated to 72° C. for 3 minutes and that the cycle was repeated 30 times.

In the presence of mineral oil, 0.1 μg of SISPA-amplified SCH DNA was incubated with 5 μg of the biotinylated normal human DNA in 50 μl of 0.12M sodium phosphate buffer (pH 7.0) at 95° C. for 5 minutes. The tube was then placed in a water bath heated to 55° C. for 4 days. Streptavidin-conjugated paramagnetic particles ("DYNABEADS"; Dynal Inc., Lake Success, N.Y.) suspended in 50 μl of 2×binding solution (2M NaCl, 1 mM EDTA, 10 mM Tris-HCl, pH 7.5) were added to the solution containing the DNA, and the mixture was incubated at room temperature for 15 minutes.

The "DYNABEADS" were confined to one side of the reaction tube with a magnet, and the nearly particle-free solution ("supernatant") was decanted. The supernatant contained SISPA amplified DNA that had not hybridized with normal human DNA.

(iv) Cloning.

The DNA in the supernatant from the above step was precipitated, resuspended in 20 μl TE, and cloned in lambda gt11 vectors as described in Example 2.

D. DNA Libraries Generated

DNA-insert phage libraries were generated from sera samples My 131, My 190, My 620, My 670, DEN, SCH, JFA and PNF 2161.

E. Deposit of DNA Libraries.

The DNA-insert phage libraries generated from sera samples My 131, My 190, DEN, SCH, JFA and PNF 2161 have been deposited with the American Type Culture Collection, 12301 Parklawn Dr., Rockville, Md. 20852, and have been assigned the following deposit designations: MY 131 DNA source, ATCC 75270; PNF 2161 DNA source, ATCC 75269; JFA DNA source, ATCC 75271; SCH DNA source, ATCC 75282; DEN DNA source, ATCC 75418, and MY 190, DNA source, ATCC 75284. The DNA-insert phage libraries generated from sera samples DEN, My 620 and My 670, as well as subtracted SCH DNA libraries can be obtained from Genelabs Technologies, Inc. 505 Penobscot Dr., Redwood City, Calif. 94063.

EXAMPLE 4

IMMUNOSCREENING OF RECOMBINANT LIBRARIES

The lambda gt11 libraries generated in Examples 1 and 2 were immunoscreened for the production of antigens recognizable by the five sera, or corresponding sera, from which the libraries were generated. The phage were plated for plaque formation using the *Escherichia coli* bacterial plating strain *E. coli* KM392 (Kevin Moore, DNAX, Palo Alto, Calif.). Alternatively, *E. coli* Y1090R- may be used.

The fusion proteins expressed by the lambda gt11 clones were screened with serum antibodies essentially as described by Ausubel, et al.

Each library was plated at approximately $2 \times 10^4$ phages per 150 mm plate. Plates were overlaid with nitrocellulose filters overnight. Filters were washed with TBS (10 mM, Tris pH 7.5; 150 mM NaCl), blocked with AIB (TBS buffer, 10 mM Tris, pH 8.0, 150 mM NaCl; with 1% gelatin) and incubated with a primary antibody diluted 100 times in AIB.

After washing with TBS, filters were incubated with a second antibody, goat-anti-human IgG conjugated to alkaline phosphatase (Promega, Madison, Wis.). Reactive plaques were developed with a substrate (for example, BCIP, 5-bromo-4-chloro-3-indolyl-phosphate), with NBT (nitro blue tetrazolium) salt (Sigma). Positive areas from the primary screening were replated and immunoscreened until pure plaques were obtained.

EXAMPLE 5

SEQUENCING OF THE cDNA INSERTS OF IMMUNOREACTIVE CLONES

The cDNA inserts of immunoreactive lambda clones were subcloned into the "BLUESCRIPT SK+" vector (Stratagene, LaJolla, Calif.), pT7 Blue T vector (Novagen, Madison, Wis.) or TA cloning vector (Invitrogen, San Diego, Calif.). The sequences for the cDNA inserts were determined as per the manufacturer's instructions using the dideoxy chain termination technique (Sanger, 1979).

Sequence data is presented in the Sequence Listing. The sequences are typically presented with cloning linkers on each end. Sequences were compared with "GEN-BANK", EMBL database and dbEST (National Library of Medicine) sequences at both nucleic acid and amino acid levels. Search programs FASTA, BLASTP, BLASTN and BLASTX indicated that these sequences are unique as both nucleic acid and amino acid sequences. In particular, none of the sequences presented in the Sequence Listing showed homology to any hepatitis virus for which sequence information is known.

EXAMPLE 6

SOUTHERN BLOT ANALYSIS OF IMMUNOREACTIVE CLONES

The inserts of immunoreactive clones were screened for their ability to hybridize to the following control DNA sources: normal human peripheral blood lymphocyte DNA (purchased from Stanford Blood Bank), normal mystax liver DNA (Centers for Disease Control), and *Escherichia coli* KM392 genomic DNA (Ausubel, et al.; Maniatis, et al.; Sambrook, et al.). Ten micrograms each of human lymphocyte DNA and normal mystax DNA, and 2 micrograms of *E. coli* DNA were digested with EcoRI and HindIII. The restriction digestion products were electrophoretically fractionated on an agarose gel (Ausubel, et al.) and transferred to nylon or nitrocellulose membranes (Schleicher and Schuell, Keene, N.H.) as per the manufacturer's instructions.

Probes from the immunoreactive clones were prepared as follows. Each clone was amplified using primers corresponding to lambda gt11 sequences that flank the EcoRI cloning site of the gt11 vector. Amplification was carried out by polymerase chain reactions utilizing each immunoreactive clones as template. The resulting amplification products were digested with EcoRI, the amplified fragments gel purified and eluted from the gel (Ausubel, et al.). The resulting amplified fragments, derived from the immunoreactive clones, were then random prime labelled (Boehringer Mannheim) using $^{32}$P-dNTPs.

The random primed probes were then hybridized to the above-prepared nylon membrane to test for hybridization of the insert sequences to the control DNAs. Typically, inserts that hybridized with any of the control DNAs were removed from consideration.

As positive hybridization controls, a probe derivative from a human C-kappa gene fragment (Hieter) was used as single gene copy control for human DNA and a *E. coli* polymerase gene fragment was similarly used for *E. coli* DNA.

EXAMPLE 7

SCREENING OF THE PNF 2161 LIBRARY

A. Immunoscreening.

The cDNA and DNA libraries of PNF 2161 in lambda gt11 were screened, as described in Example 4, with JFA, My 187 (FIG. 1) and PNF 2161 sera. The results of the screening are presented in Table 2.

TABLE 2

PNF2161 Libraries

| Library[1] | % Recomb.[2] | Antibody[3] | # Screened | # Clones Plaque-Purified | Neg w/ Norm Human[4] |
|---|---|---|---|---|---|
| PNF/RNA | 90 | JFA | 1.2 × 10⁵ | 0 | — |
| PNF/RNA | 90 | PNF | 8 × 104 | 7 | 7 |
| PNF/RNA | 90 | My187 | 4 × 104 | 18 | 13 |
| PNF/RNA | 90 | JFA | 1.6 × 105 | 61 | 46 |
| TOTALS: | | | | 86 | 66 |

1. Library constructed from the indicated human/mystax source, using either DNA or RNA as starting material.
2. Percent recombinant clones in the indicated λgt11 library as determined by blue/white plaque assay and confirmed by PCR amplification of randomly selected clones.
3. Antisera source used for the immunoscreening of each indicated library.
4. Number of clones determined to have no immunoreactivity with pre-inoculum mystax and/or normal human sera.

One of the clones isolated by the above screen (PNF 2161 clone 470-20-1, SEQ ID NO:106), was used to generate extension clones, as described in Example 7C.

B. Sucrose Density Gradient Separation of PNF2161.

A continuous gradient of 10–60% sucrose ("ULTRAPURE", Gibco/BRL, Gaithersburg, Md.) in TNE (50 mM Tris-Cl, pH 7.5, 100 mM NaCl, 1 mM EDTA) was prepared using a gradient maker from Hoefer Scientific (San Francisco, Calif.). Approximately 12.5 ml of the gradient was overlaid with 0.4 ml of PNF serum which had been stored at −70° C., rapidly thawed at 37° C., then diluted in TNE. The gradient was then centrifuged in the SW40 rotor (Beckman) at 40,000 rpm (approximately 200,000×g at $r_{av}$) at 4° C. for approximately 18 hours. Fractions of volume approximately 0.6 ml were collected from the bottom of the tube, and 0.5 ml was weighed directly into the ultracentrifuge tube, for calculation of density.

TABLE 3

MEASURED DENSITIES OF PNF FRACTIONS AND PRESENCE OF 470-20-1

| Fraction | Density | 470-20-1 Detected* |
|---|---|---|
| 1 | 1.274 | − |
| 2 | 1.274 | − |
| 3 | 1.266 | − |
| 4 | 1.266 | − |
| 5 | 1.260 | − |
| 6 | 1.254 | − |
| 7 | 1.248 | + |
| 8 | 1.206 | + |
| 9 | 1.146 | + |
| 10 | 1.126 | +++ |
| 11 | 1.098 | ++++ |
| 12 | 1.068 | +++ |
| 13 | 1.050 | + |
| 14 | 1.034 | + |
| 15 | 1.036 | + |
| 16 | 1.018 | − |
| 17 | 1.008 | + |
| 18 | 1.020 | + |

*"+" and "−" scores were initially based on 40-cycle PCR. In order to distinguish "+", "++", "+++", and "++++", fractions giving initial positive scores (7–18) were amplified with 30 cycles of PCR.

The putative viral particles were then pelleted by centrifugation at 40,000 rpm in the Ti70.1 rotor (approximately 110,000×g) at 4° C. for 2 hours, and RNA was extracted using the acid guanidinium phenol technique ("TRI REAGENT", Molecular Research Center, Cincinnati, Ohio), and alcohol-precipitated using glycogen as a carrier to improve recovery. The purified nucleic acid was dissolved in an RNase-free buffer containing 2 mM DTT and 1 U/ml recombinant RNasin.

Analysis of the gradient fractions by RNA PCR showed a distinct peak in the 470-20-1 specific signal, localized in fractions of density ranging from 1.126 to 1.068 g/ml (Table 3). The 470-20-1 signal is thus shown, under these conditions, to form a discrete band, consistent with the expected behavior of a viral particle in a sucrose gradient.

C. Generation of 470-20-1 Extension Clones.

The extracted RNA was passed through a "CHROMA SPIN" 100 gel filtration column (Clontech, Palo Alto, Calif.) to remove small molecular weight impurities. cDNA was synthesized using a Boehringer-Mannheim cDNA synthesis kit (Boehringer-Mannheim, Indianapolis, Ind.). After cDNA synthesis the PNF cDNA was ligated to a 50 to 100 fold excess of KL-1/KL-2 SISPA linkers (SEQ ID NO:64, SEQ ID NO:65, respectively) and amplified for 35 cycles using the primer KL-1.

The 470 extension clones were generated by anchored PCR of a 1 μl aliquot from a 10 μl ligation reaction containing EcoRI digested (dephosphorylated) lambda gt11 arms (1 μg) and EcoRI digested PNF cDNA (0.2 μg). PCR amplification (40 cycles) of the ligation reaction was carried out using the lambda gt11 reverse primer in combination with either 470-20-77F (SEQ ID NO:25) or 470-20-1-211R (SEQ ID NO:26). All primer concentrations for PCR were 0.2 μM. The amplification products (9 μl/100 μl) were separated on a 1.5% agarose gel, blotted to "NYTRAN" (Schleicher and Schuell, Keene, N.H.), and probed with a digoxygenin labelled oligonucleotide probe specific for 470-20-1. The digoxygenin labeling was performed according to the manufacturer's recommendations using terminal transferase (Boehringer-Mannheim). Bands that hybridized were gel-purified, cloned into the "TA CLONING VECTOR pCR II" (Invitrogen, San Diego, Calif.), and sequenced. Clones having both 5' and 3' extensions were identified (designated 470F-16 and 470R-1, respectively). All sequences reported here were confirmed by the sequencing of at least two independent isolates. The 5' extension obtained was 159 nucleotides and the 3' extension was 68 nucleotides (SEQ ID NO:104).

EXAMPLE 8

IMMUNOSCREENING OF THE MY 131 AND MY 190 LIBRARIES

A. Immunoscreening

The cDNA and DNA libraries of My 131 in lambda gt11 were screened, as described in Example 4, with My 136 (FIG. 1) and PNF 2161 sera. The results of the screening are presented in Table 4.

TABLE 4

My131 Libraries

| Library[1] | % Recomb.[2] | Antibody[3] | # Screened | # Clones Plaque-Purified | # Pre/Norm & SB Neg[4] |
|---|---|---|---|---|---|
| My131/RNA | 85 | PNF | $1.6 \times 10^5$ | 17 | 1 |
| My131/DNA | 91 | PNF | $1.2 \times 10^5$ | 34 | 7 |
| My131/RNA | 93 | My136 | $6.0 \times 10^4$ | 11 | 1 |
| My131/DNA | 85 | My136 | $6.0 \times 10^4$ | 44 | 8 |
| TOTALS: | | | | 106 | 17 |

1. Library constructed from the indicated mystax source, using either DNA or RNA as starting material.
2. Percent recombinant clones in the indicated λgt11 library as determined by blue/white plaque assay and confirmed by PCR amplification of randomly selected clones.
3. Antisera source used for the immunoscreening of each indicated library.
4. Number of clones determined to have no immunoreactivity with pre-inoculum mystax and/or normal human sera as well as an absence of hybridization to human mystax, and *E. coli* genomic DNA in Southern blotting (S.B.) assays.

The cDNA and DNA libraries of My 190 in lambda gt11 were screened, as described in Example 4, with My 88 sera. The results of the screening are presented in Table 5.

TABLE 5

MyGB Libraries

| Library[1] | % Recomb.[2] | Antibody[3] | # Screened | # Clones Plaque-Purified | # Pre/Norm & SB Neg[4] |
|---|---|---|---|---|---|
| MyGB/RNA | 85 | My88 | $1.5 \times 10^5$ | 19 | 6 |
| MyGB/DNA | 84 | My88 | $1.1 \times 10^5$ | 78 | 40 |
| TOTALS: | | | | 97 | 46 |

1. Library constructed from the indicated human/mystax source, using either DNA or RNA as starting material.
2. Percent recombinant clones in the indicated λgt11 library as determined by blue/white plaque assay and confirmed by PCR amplification of randomly selected clones.
3. Antisera source used for the immunoscreening of each indicated library.
4. Number of clones determined to have no immunoreactivity with pre-inoculum mystax and/or normal human sera as well as an absence of hybridization to human, mystax, and *E. coli* genomic DNA in Southern blotting (S.B.) assays.

B. Characterization of My 131 Clones

All clones that (i) tested positive for immunoreactivity in the plaque screening assays using PNF 2161 and My 136 sera, (ii) were determined to be exogenous to human, mystax, and *E. coli* genomic DNA, and (iii) were non-immunoreactive with pre-inoculum and/or normal human sera, were subcloned, sequenced and further analyzed.

Seven candidate clones were found to have open reading frames in phase with the β-galactosidase—427-7-1, 428-2-3, 428-7-3, 428-3-1, 430-4-8, 430-2-1 and 430-3-4.

C. Characterization of My 190 Immunoreactive Clones

All clones that (i) tested positive for immunoreactivity in the plaque screening assay using My 88 sera, (ii) were determined to be exogenous to human, mystax, and *E. coli* genomic DNA, and (iii) were non-immunoreactive with pre-inoculum and/or normal sera, were subcloned, sequenced and further analyzed.

Seven primary candidate clones were found having open reading frames continuous with the β-galactosidase—D5, D6, D12, D13, D19, D44, and D76.

Eleven additional clones contained open reading frames greater than 15 amino acids in length. The are: D20, D24, R27, D30, D31-2, D48, and D64.

Two of the My 190 immunoreactive clones were rescreened by the plaque screening assay against the sera shown in Table 6.

TABLE 6

| Sera | D19 | D30 |
|---|---|---|
| My73 pre-GB | – | – |
| My73 post-GB | | |
| IgM | + | – |
| IgG | + | – |
| My136 pre-GB | – | – |
| My136 post-GB | – | – |
| My242 pre-GB | – | – |
| My242 post-GB | – | – |
| My88 | + | + |

One of the clones, D19, showed cross-reactivity with other mystax hepatitis N(ABCDE) sera.

Figure 2:
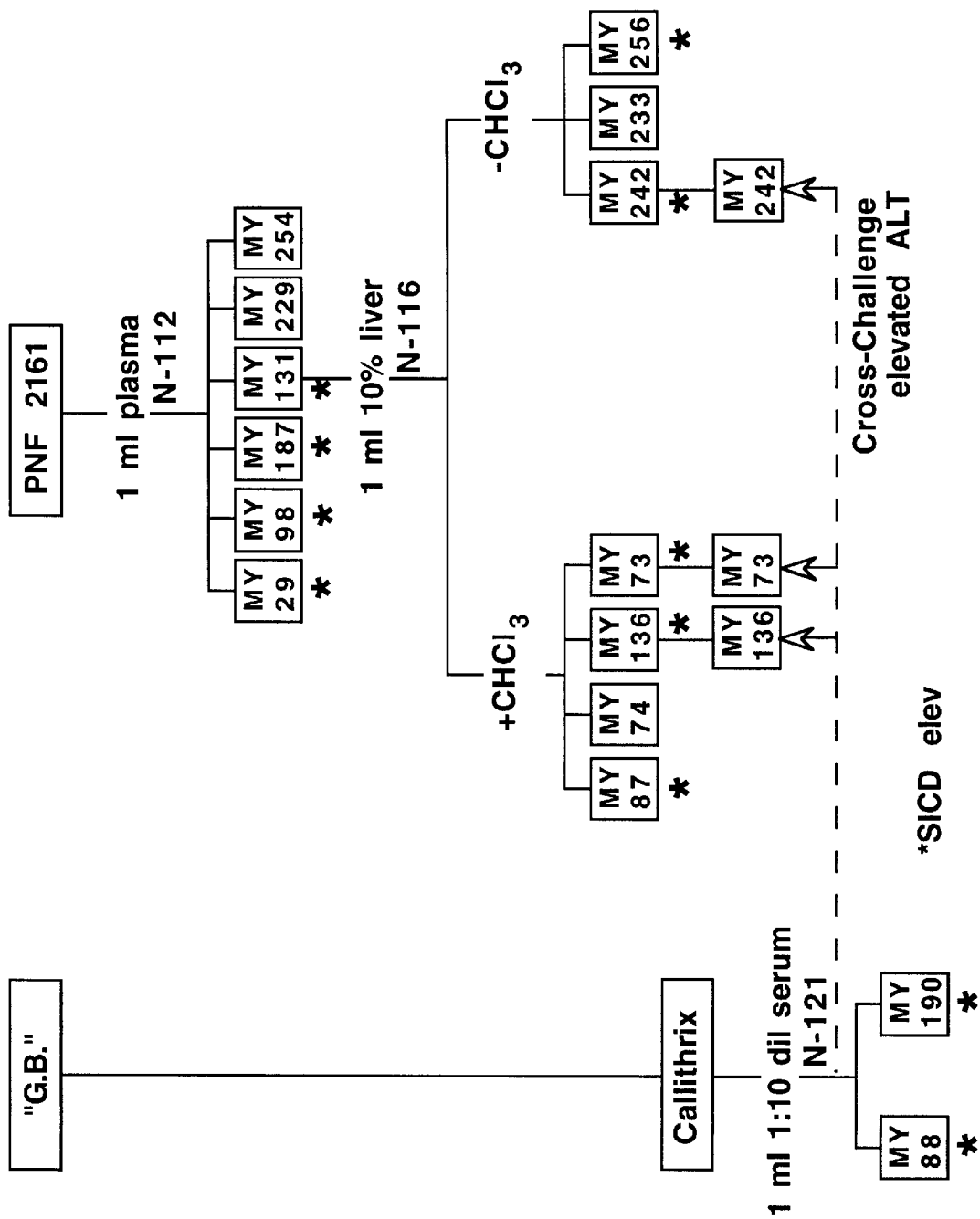
FIG. 2: the GB sera use in cross challenge to mystax infected with passaged sera derived from PNF 2161 is diagrammed.

The sera used in Table 6 were characterized as follows (refer to FIGS. 1 and 2): MY 73 and MY 136, were initially infected with 1 ml of 10% liver homogenate of MY 131 treated with $CHCl_3$. 100 days after infection, MY 73 and MY 136 were cross challenged with GB agent; MY 242, infected with 10% liver homogenate of MY 131 (not treated with $CHCl_3$), was cross challenged with GB agent after 100 days; MY 190 and MY 88 are, respectively, the acute phase and convalescent phase sera for GB agent; MY 162 is a normal mystax serum; MY 131 is the acute phase mystax serum for PNF2161; and PNF2161 is a chronic human hepatitis serum. "Pre-GB" means 100 days after inoculation with MY 131 liver homogenate, that is, convalescent phase sera that corresponds to the MY 131 inoculum.

EXAMPLE 9

FURTHER CHARACTERIZATION OF CLONES D6 and D19

A. Amplification Reactions with Genomic DNA using D19 Primers

Primers were derived from the insert of clone D19 (D19-NF, SEQ ID NO:68; D19-BR, SEQ ID NO:69). These primers were used in polymerase chain reaction amplifications (Mullis; Mullis, et al.) with the following substrate DNAs: normal human (peripheral lymphocyte DNA, Stanford Blood Bank), normal mystax liver DNA (Mystax 753, Centers for Disease Control), and *E. coli* (KM392). Two controls were also run, (i) a no substrate DNA control and (ii) a positive control corresponding to the plasmid containing the cloned DNA from which the primer set was derived (i.e., plasmid D19). The results of the amplification reactions are presented in Table 7.

TABLE 7

| DNA | D19 |
| --- | --- |
| Normal Human | − |
| Normal Mystax | − |
| E. coli | − |
| H$_2$O | − |
| Positive control | + |

The results presented in Table 7 further demonstrate that cloned sequence D19 is not derived from normal human, mystax, or bacterial genomes, i.e., D19 represents sequences exogenous to these test genomic DNAs.

B. Further Immunoscreening using D19

The D19 clone encoded antigen was immunoscreened against nine additional mystax serum samples. The clone was immunoreactive with 2/9 of the sera.

C. Expression and Partial Purification of D6 and D19 as GST Fusion Proteins

1. Expression of D6 and D19 Fusion Proteins.

The D6 and D19 sequences were subcloned into the bacterial expression vector, pGEX-GLI. The pGEX-GLI is a modification of the pGEX-1 vector of Smith, et al., which involved the insertion of a thrombin cleavage sequence in-frame with the glutathione-S-transferase protein (GST: sj26 coding sequence) and addition of NcoI and BamHI restriction sites. The NcoI primers in the amplified fragment allow in-frame fusion of D6 or D19 coding sequence to the sj26-thrombin coding sequences.

The D19 coding sequence insert was generated by the polymerase chain reaction using PCR primers specific for each insert. Typically, the 5' primer contains a NcoI restriction site and the 3' primer contains stop-codons followed by a BamHI restriction site. The D19-5' primer was D19-NF (SEQ ID NO:68). The D19-3' primer was D19-RF (SEQ ID NO:69). The generated PCR product was digested with NcoI and BamHI and gel purified.

D6 coding sequence insert was prepared in a similar fashion. The D6-5' primer was D6-NF (SEQ ID NO:66) and the D6-3' primer was D6-BR (SEQ ID NO:67). The pGEX-GLI vector was digested with NcoI and BamHI and the linear vector isolated.

Manipulations were carried out for both coding sequence inserts essentially as described below for the D19 insert sequence. The NcoI/BamHI D19 fragment was ligated to the linear PGEX-GLI vector. The ligation mixture was transformed into E. coli and ampicillin resistant colonies were selected. Plasmids were isolated from the ampicillin resistant colonies and analyzed by restriction enzyme digestion. One of the candidate clones was designated pGEX-GLI-D19.

E. coli strain JM101 was transformed with pGEX-GLI-D19 and was grown at 37° C. overnight. DNA was prepared from randomly-picked colonies. The presence of the insert coding sequence was confirmed by (i) restriction digest mapping and (ii) hybridization screening using labelled D19 inserts (i.e., Southern analysis).

2. Partial Purification of D6 and D19.

Partial purification of the D19 encoded protein is described below: D19 protein was purified using the same methodology.

A D19 clone was identified, see above, and grown overnight. The overnight culture was diluted 1:10 with LB medium containing ampicillin and grown for one hour at 37° C. Alternatively, the overnight culture was diluted 1:100 and grown to CD of 0.5–1.0 before addition of IPTG (isopropylthio-β-galactoside). IPTG (GIBCO-BRL) was added to a final concentration of 0.2–0.5 mM for the induction of protein expression and the incubation was continued for 2–5 hours, preferably 3.5 hours.

Bacterial cells were harvested by centrifugation and resuspended in 1/100 culture volume of MTPBS (150 mM NaCl, 16 mM Na$_2$HPO$_4$, 4 mM NaH$_2$PO$_4$). Cells were lysed by lysozyme, sonication or French press, and lysates cleared of cellular debris by centrifugation.

Sometimes, an aliquot of the supernatant obtained from IPTG-induced cultures of pGEX-GLI-D19-containing cells and an aliquot of the supernatant obtained from IPTG-induced cultures of pGEX-GLI-vector alone were analyzed by SDS-polyacrylamide gel electrophoresis followed by Western blotting, as described below.

If necessary, the extracts can be concentrated by ultrafiltration using, for example, a "CENTRICON 10" filter.

Alternatively, the fusion proteins were partially purified over a glutathione agarose affinity column as described in detail by Smith, et al. In this method, 100 ml cultures were grown overnight. The cultures are diluted to 1 liter, and the cells grown another hour at 37° C. Expression of the fusion proteins was induced using IPTG. The induced cultures were grown at 37° C. for 3.5 hours. Cells were harvested and a sonicator was used to lyse the cells. Cellular debris was pelleted and the clear lysate was loaded onto a glutathione "SEPHAROSE" column. The column was washed with several column volumes. The fusion protein was eluted from the affinity column with reduced glutathione and dialyzed.

D. Western Blot Analysis

Six milliliters of the above culture media were concentrated to 50 μl using a "CENTRICON-10" microconcentrator (Amicon). The concentrated media was brought to a total volume of 400 μl by addition of SDS-ME disruption buffer and 10 μl was loaded into each of four lanes of a 12% reducing acrylamide gel (Ausubel et al.). Protein was transferred using standard procedures (Ausubel et al.) from the gel to nitrocellulose membrane (Schleicher & Schuell).

The membranes were incubated with the test serum (for example, Mystax 88 or Ruf serum) and washed. The membranes were then incubated with a labelled antibody suitable for detection of binding of antibodies from the test sera: for example, alkaline phosphatase-conjugated goat anti-human antibody (Mystax 88). Excess goat anti-human IgG antibody was removed from the membranes (Ausubel et al.; Harlow et al.) and the membranes calorimetrically developed.

Figure 3:
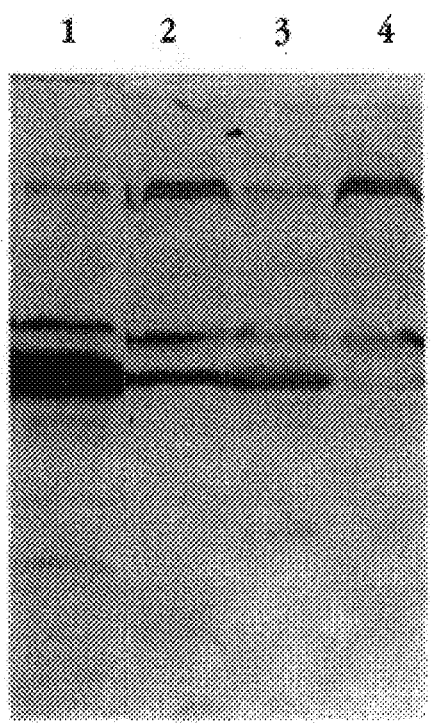
FIG. 3: illustrates the results of a Western blot analysis of the membrane containing crude lysates containing the pGEX-GLI-D6 and pGEX-GLI-D19 encoded antigens of the present invention.

FIG. 3 illustrates the results of a Western blot analysis of the membrane containing crude lysates of the following samples: induced (FIG. 3, lane 1) and un-induced (FIG. 3, lane 2) pGEX-GLI-D6; induced (FIG. 3, lane 3) and un-induced (FIG. 3, lane 4) pGEX-GLI-D19. For the blot, the test serum was a 1:100 dilution of N-(ABCDE) mystax (My 88) serum.

Figure 4A:
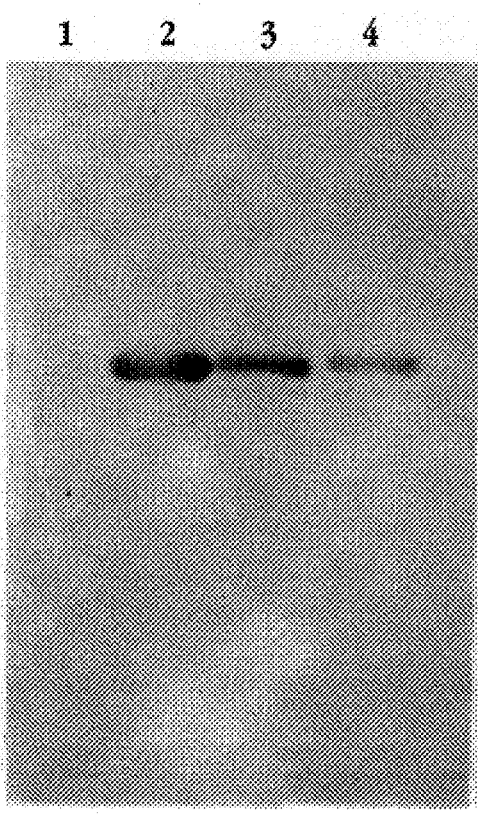
FIGS. 4A and 4B: illustrate the results of Western blots of the partially purified D1, D6 and D19 fusion proteins using mystax (My 88) serum (FIG. 4A) and N-(ABCDE) human (Ruf) serum (FIG. 4B).
Figure 4B:
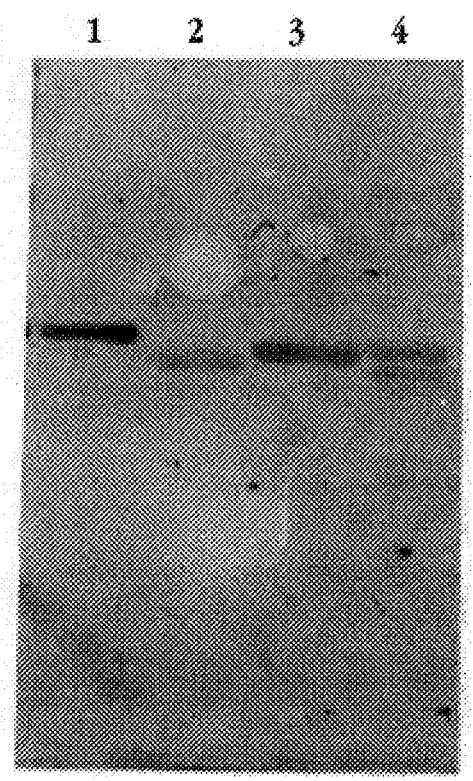

FIGS. 4A and 4B illustrates Western blots of the partially purified proteins using mystax (My 88) serum (FIG. 4A) and N-(ABCDE) human (Ruf) serum (FIG. 4B). The partially purified proteins include D6 and D19 fusion proteins. The sj26 antigen was used as a control.

As shown in the FIGS. 3 and 4, the membranes treated with infected sera (My88 and human (Ruf)) showed specific immunoreactivity with the N-(ABCDE) fusion proteins and Ruf serum reacted weakly to Sj26. The pGEX-GLI-D19 is considered negative with the human serum.

EXAMPLE 10

IMMUNOSCREENING OF THE JFA LIBRARY

A. Immunoscreening

The cDNA and DNA libraries of JFA in lambda gt11 were constructed and screened, as described in Example 2, 3 and 4, with JFA sera. The results of the screening are presented in Table 8.

TABLE 8

| Library[1] | % Recomb.[2] | Antibody[3] | # Screened | # Clones Plaque-Purified | # Norm & SB Neg.[4] |
|---|---|---|---|---|---|
| JFA/RNA (<500 bp) | 95 | JFA | $1.5 \times 10^5$ | 0 | 0 |
| JFA/DNA (<500 bp) | 95 | JFA | $1.0 \times 10^5$ | 4 | 2 |
| JFA/DNA (>500 bp) | 91 | JFA | $1.0 \times 10^5$ | 7 | 5 |
| TOTALS: | | | | 11 | 7 |

1. Library constructed from the indicated human source, using either DNA or RNA as starting material.
2. Percent recombinant clones in the indicated λgt11 library as determined by blue/white plaque assay and confirmed by PCR amplification of randomly selected clones.
3. Antisera source used for the immunoscreening of each indicated library.
4. Number of clones determined to have no immunoreactivity with normal human sera as well as an absence of hybridization to human genomic DNA in Southern blotting (S.B.) assays.

B. Characterization of JFA Clones

All clones that (i) tested positive for immunoreactivity in the plaque screening assays using JFA, (ii) were determined to be exogenous to human DNA, and (iii) were non-immunoreactive with normal sera, were subcloned, sequenced and further analyzed. In addition, one clone containing sequences that hybridized with human sequences but that also had broad cross reactivity with N-(ABCDE) infected sera was sequenced (clone 8A).

Three candidate clones (1A, 4B(a,b,c), and 17A) were found having large open reading frame continuous with the β-galactosidase. 4B(a,b,c) is a co-ligated DNA clone consisting of three inserts separated by cloning linkers.

The characterization of the JFA clones is summarized in Table 9.

TABLE 9

| Clone | Size (bp) | ORF (aa) | Novel Sequence | Exogenous Southern Blots |
|---|---|---|---|---|
| 1A (6A)* | 467 | Y (155) | Y | Y |
| 4Ba | 180 | Y (59) | Y | Y |
| 4Bb | 176 | Y (58) | N | Y |
| 4Bc | 168 | Y (56) | Y | Y |
| 11A (13A) | 592 | N (7) | N | Y |
| 17A (18A)* | 590 | Y (196) | Y | Y |

Y =
1) Presence of ORF
2) Absence of known homology to known sequence
3) Exogenous clone
N =
1) Absence of continuous ORF
2) Homology to known sequences in data base
3) Human genomic sequence
N.D. = Not determined
*1A, 17A expressed in pGEX-GLI in *E. coli*. Insoluble proteins.

C. Further Characterization of Clones 17A and 1A

Clones 17A and 1A have both been shown to have exogenous, non-human insert sequences. Both clones contain a single coding sequence continuous with the open reading frame of β-galactosidase in the lambda gt11 vector.

The insert-coding sequences of both clones 17A and 1A have been cloned into the pGEX-GLI vector and expressed as fusion proteins, as described above for clones D6 and D19. For the expression of JFA 17A the following primers were used: 17A-NF, 5' (SEQ ID NO:70) and 17A-BR, 3' (SEQ ID NO:71). For the expression of JFA 1A the following primers were used: 1A-NF, 5' (SEQ ID NO:72) and 1A-BR, 3' (SEQ ID NO:73).

The following samples were electrophoretically separated on a polyacrylamide gel: Sj26 (lanes 2, 3, 10 and 11); the induced crude lysates from clones 17A and 1A —lanes 4–8 and 12–15, respectively, where (i) lanes 4 and 12 are from zero time points, (ii) lanes 5–8 are from a 3.5 hour induced sample, with increasing protein concentration per lane, and (iii) lanes 13–15 are from a 2 hour induced sample, with increasing protein concentration per lane; and a pool of purified clone 1A protein before (lane 16) and after (lane 17) concentration using a stirred-gel micro-concentrator (Amicon). Sj26 as a control. Lanes 1 and 9 contained molecular weight standards. The gel was coomassie blue stained.

In a Western blot analysis of the above polyacrylamide gel transferred to a membrane and probed with JFA serum; both the Sj26-17A and Sj26-1A fusion proteins are immunoreactive with JFA serum; however, equivalent amounts of Sj26 protein are not immunoreactive. A Western blot analysis of the polyacrylamide gel transferred to a membrane and probed with normal human serum indicated that. 1A and 17A proteins are not immunoreactive to normal serum.

D. Isolation of Overlapping Clones to Clones 17A and 1A

A JFA DNA library was generated in "LAMBDA ZAPII" (Stratagene, LaJolla, Calif.) using JFA random-primed SISPA DNA, prepared essentially as described in Example 3, except that the amplified DNA was digested with NotI instead of EcoRI.

Undigested "LAMBDA ZAPII" DNA was cut with NotI and then treated with calf intestinal phosphatase (CIP) to prevent re-ligation of phage DNA ends.

A ligation reaction to insert JFA SISPA DNA fragments into phage DNA at the NotI site was performed essentially as described in Example 2D. The ligated cDNA was packaged the following morning by standard procedures using a lambda DNA packaging system (Stratagene). The packaged phage were used to infect *E. coli* strain PLK-A'. A titer for the recombinant DNA phage library was determined by standard methods.

E. Screening of Overlapping Clones to Clone 17A

About $4 \times 10^5$ "LAMBDA ZAP II" recombinants were screened using radioactively-labelled insert of clone 17A. Specifically, EcoRI DNA inserts of clone 17A were labelled by random-priming (Boehringer Mannheim) and employed as a probe in hybridization experiments to identify overlapping DNA sequences. Sequences identified by this method can, in turn, be used as probes to identify further contiguous clones.

In a primary screening of the random-primed JFA library using the clone 17A insert (screening was performed essentially as described in Example 6), 8 hybridization-positive clones were identified.

The hybridization-positive clones were screened with oligonucleotides located at 5'- or 3'-ends of clone 17A. To screen clone 17A positives the 5'-end oligonucleotide was 17A-57F, 5' (SEQ ID NO:56) and the 3'-end oligonucleotide was 17A-602R, 3' (SEQ ID NO:57). The oligonucleotides were end-labelled with T4 polynucleotide kinase and γ-$^{32}$P-ATP (Maniatis, et al.)

Figure 5:
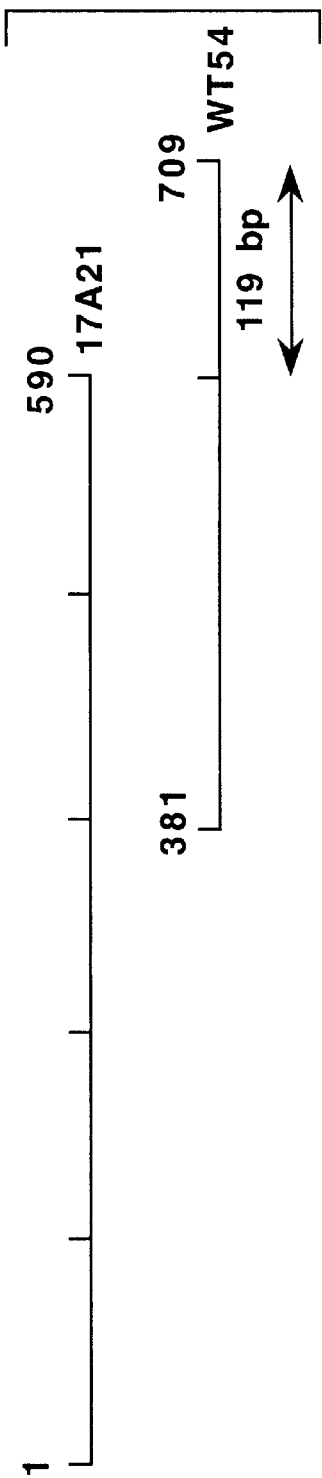
FIG. 5: schematically illustrates the overlap between clone 17A and WT54.

The screening procedure using oligonucleotides complementary to clone 17A resulted in 1 positive and 7 negatives. The clone that showed a positive hybridization to the 3'-end primer contained an insert of about 400 base pairs as estimated by gel electrophoresis. This clone was designated clone WT54. The insert of WT54 was sequenced and contained a 210 base pair overlap with 17A which extends 119 base pairs from the 3'-end of 17A. The sequence of this insert is presented as SEQ ID NO:58. FIG. 5 schematically illustrates the overlap between clone 17A and WT54.

The 17A clones that gave a negative hybridization result with the oligonucleotide primers were rescreened. The probe used for rescreening was a PCR-generated clone 17A insert generated from 5'-and 3'-end oligonucleotide primers (SEQ ID NO:70 and SEQ ID NO:71), and digested with NcoI and BamHI prior to labelling. This procedure resulted in 6 positives and 1 negative. All 6 positive clone inserts were sequenced and corresponded to internal 17A sequences.

F. Characterization of WT54 Clone

The WT54 clone was characterized for its ability to hybridize to the following control DNA sources: normal human peripheral blood lymphocyte DNA (purchased from Stanford Blood Bank), normal mystax liver DNA (Centers for Disease Control), and *Escherichia coli* KM392 genomic DNA (Ausubel, et al.; Maniatis, et al.; Sambrook, et al.). Ten micrograms each of human lymphocyte DNA and normal mystax DNA, and 2 micrograms of *E. coli* DNA were digested with EcoRI and HindIII. The restriction digestion products were electrophoretically fractionated on an agarose gel (Ausubel, et al.) and transferred to nylon membranes (Schleicher and Schuell, Keene, N.H.) as per the manufacturer's instructions.

Radiolabelled clone WT54 was prepared as follows. oligonucleotide 5'- and 3'- primers were synthesized in the region of clone WT54 that does not overlap with clone 17A. The 5'-primer is WT54-590F (SEQ ID NO:59) and the 3'-primer is WT54-684R (SEQ ID NO:60). The primers were used to amplify the region between base pairs 590 and 684 by PCR. The resulting amplified fragment was then labelled by the random-priming method (Boehringer Mannheim) using $^{32}$P-dNTPs and then used as a probe.

The labelled probe was then hybridized to the above-prepared nylon membrane to test for hybridization of the insert sequences to the control DNAS. The probe did not hybridize to human, *E.coli* or mystax genomic DNA.

Figure 6:
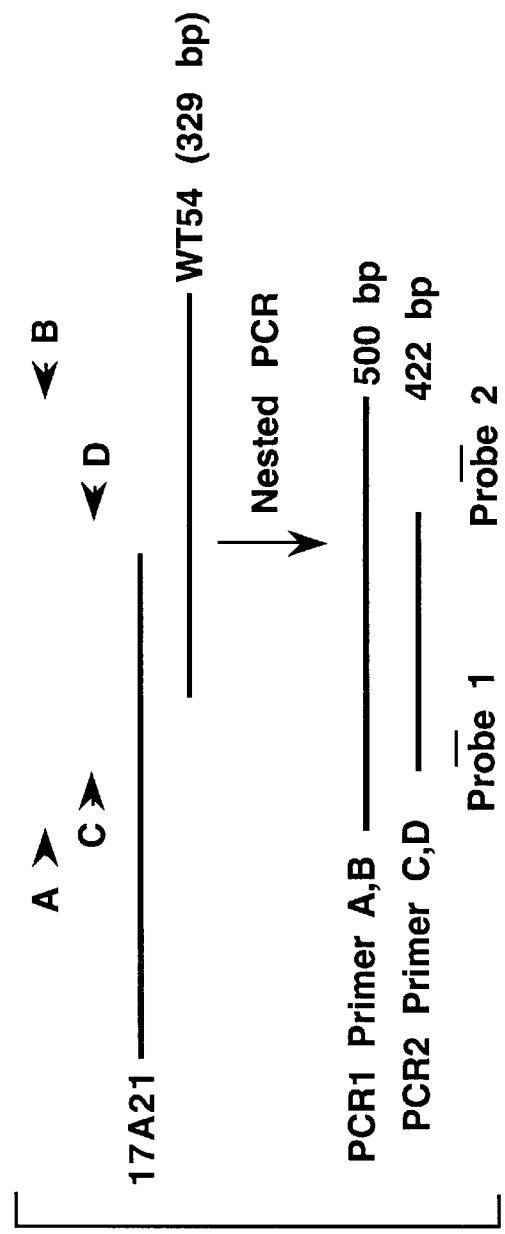
FIG. 6: schematically represents the steps taken in the polymerase chain reaction linking experiments for clones JFA-17A and WT54.

To determine that the 17A-WT54 linked sequence is present in JFA SISPA DNA and is not an artifact due to cloning manipulations, the following primers were selected, prepared and used in amplification reactions: a 5'-primer unique to clone 17A sequences, i.e., 17A sequences that do not overlap WT54 sequences; and a 3'-primer unique to clone WT54 sequences, i.e., WT54 sequences that do not overlap 17A sequences. The 5'-primer is 17A-215F (FIG. 6, A—SEQ ID NO:61) and the 3'-primer is WT54-684R (FIG. 6, B—SEQ ID NO:60). The primers were used to amplify the putative linked region between base pairs 215 and 684 by PCR using JFA SISPA DNA and serum DNA as template.

The resulting amplified product was then amplified using internal nested primers, 17A-258F (FIG. 6, C—SEQ ID NO:62) and WT54 647R (FIG. 6, D—SEQ ID NO:63). The final PCR product was probed with a labelled-oligonucleotide specific for a non-overlapping 17A insert sequence, 17A-312F (FIG. 6, Probe 1—SEQ ID NO:52), and a labelled-oligonucleotide specific to a non-overlapping WT54 sequence, WT54-592F (FIG. 6, Probe 2—SEQ ID NO:53).

Hybridization screening of the nested amplification products, using JFA SISPA DNA as template, with Probes 1 and 2 gave a positive result. This result indicates that JFA 17A and WT54 sequences are contiguous in the JFA SISPA DNA.

EXAMPLE 11

IMMUNOSCREENING OF THE SCH LIBRARIES

A. Immunoscreening

The unsubtracted and subtracted SCH DNA libraries, generated from SCH serum in lambda gt11, were screened with convalescent SCH serum as described in Example 4. The DNA clones obtained from the unsubtracted library were designated "SU". The DNA clones from the subtracted DNA library of SCH were designated "SC". The results of the screening are presented in Table 10.

TABLE 10

| Library | % Recomb[1] | Antibody[2] | # Screened | # Clones Plaque-Purified | Exogenous Clones[3] |
|---------|-------------|-------------|------------|--------------------------|----------------------|
| SU      | 83          | SCH (conval) | $1.6 \times 10^5$ | 32 | 17 |
| SC      | 94          | SCH (conval) | $2 \times 10^5$ | 27 | 2 |

1. Percent recombinant clones in the indicated λgt11 library as determined by blue/white plaque assay and confirmed by PCR amplification of randomly selected clones.
2. Antisera source used for the immunoscreening of each indicated library.
3. Number of clones determined to have no immunoreactivity with normal human sera as well as an absence of hybridization to human mystax, and *E. coli* genomic DNA in Southern blotting (S.B.) and genomic PCR assays.

B. Characterization of SCH Clones

Nineteen clones (i) tested positive for immunoreactivity in the plaque screening assays using SCH, (ii) were determined to be exogenous to human, *E. coli* and yeast genomic DNA by genomic PCR (Example 14), and (iii) were non-immunoreactive with normal sera. Further, the insert sequences were determined to be novel (i.e., they did not have sequence homology to any GENBANK sequences) and each contained an open reading frame continuous with the β-galactosidase coding sequence of the lambda gt11 vector.

These clones are identified by SEQ ID NO:84 to SEQ ID NO:102.

EXAMPLE 12

Isolation of D19 Fusion Protein

Sepharose 4B beads conjugated with anti-β-galactosidase is purchased from Promega. The beads are packed in 2 ml column and washed successively with phosphate-buffered saline with 0.02% sodium azide and 10 ml TX buffer (10 mM Tris buffer, pH 7.4, 1% aprotinin).

Lysogens infected with gt11/D19 are used to inoculate 500 ml of NZYDT broth. The culture is incubated at 32° C. with aeration to an O.D. of about 0.2 to 0.4, then brought to 43° C. quickly in a 43° C. water bath for 15 minutes to induce gt11 peptide synthesis, and incubated further at 37° C. for 1 hour. The cells are pelleted by centrifugation, suspended in 10 ml of lysis buffer (10 mM Tris, pH 7.4 containing 2% "TRITON X-100" and 1% aprotinin added just before use.

The resuspended cells are frozen in liquid nitrogen, then thawed, resulting in substantially complete cell lysis. The lysate is treated with DNase I to digest bacterial and phage DNA, as evidenced by a gradual loss of viscosity in the lysate. Non-solubilized material is removed by centrifugation.

The clarified lysate material is loaded on the Sepharose column, the ends of the column closed, and the column placed on a rotary shaker for 2 hrs. at room temperature and 16 hours at 4° C. After the column settles, it is washed with 10 ml of TX buffer. The fused protein is eluted with 0.1M carbonate/bicarbonate buffer, pH 10. Typically, 14 ml of the elution buffer is passed through the column, and the fusion protein is eluted in the first 4–6 ml of eluate.

The eluate containing the fusion protein is concentrated in "CENTRICON-30" cartridges (Amicon, Danvers, Mass.). The final protein concentrate is resuspended in, for example, 400 µl PBS buffer. Protein purity is analyzed by SDS-PAGE.

EXAMPLE 13

Preparation of Anti-D19 Antibody

Expression of a glutathione S-transferase fused protein (Sj26 fused protein) containing the D19 peptide antigen was achieved in *E. coli* strain JM101 (above). The fusion protein is isolated from lysed bacteria, and isolated by affinity chromatography on a column packed with glutathione-conjugated beads, according to published methods (Smith, et al.).

The purified Sj26/D19 fused protein is injected subcutaneously in Freund's adjuvant in a rabbit. Approximately 1 mg of fused protein is injected at days 0 and 21, and rabbit serum is typically collected at 6 and 8 weeks. A second rabbit is similarly immunized with purified Sj26 protein obtained from control bacterial lysate.

Minilysates from the following bacterial cultures are prepared: (1) KM392 cells infected with pGEX and pGEX containing the D19 insert; and (2) cells infected with lambda gt11 containing the D19 insert. The minilysates and a commercial source β-galactosidase are fractionated by SDS-PAGE, and the bands transferred to nitrocellulose filters for Western blotting.

Summarizing the expected results, serum from control (Sj26) rabbits is immunoreactive with each of the Sj26 and Sj26 fused protein antigens. Serum from the animal immunized with Sj26/D19 fused protein is reactive with all Sj-26 and β-gal fusion proteins containing D19 coding sequences, indicating the presence of specific immunoreaction with the D19 antigen. None of the sera are expected to be immunoreactive with β-galactosidase.

Anti-D19 antibody present in the sera from the animal immunized with the Sj26/D19 is purified by affinity chromatography (using the D19 ligand, essentially as described above in Example 12 for the anti-β-galactosidase antibody.

EXAMPLE 14

PCR DETECTION OF N(ABCDE) HEPATITIS SEQUENCES

A polymerase chain reaction testing algorithm was devised first to verify exogenicity with respect to several genomic DNAs which could have been inadvertently cloned during library construction, then to test for the presence of the cloned sequence in the cloning source and related specimen materials. Several different types of specimens, including SISPA-amplified nucleic acids and nucleic acids extracted from the primary source, and nucleic acids extracted from related source materials (e.g., from animal passage studies), were tested.

A. Amplification from SISPA Uncloned Nucleic Acids

SISPA (Sequence-Independent Single Primer Amplification) amplified cDNA and DNA were used as templates (Example 2). Sequence-specific primers designed from selected cloned sequences were used to amplify DNA fragments of interest from the templates. Typically, the templates were the SISPA-amplified samples used in the cloning manipulations. For example, amplification primers 470-20-1-77F (SEQ ID NO:25) and 470-20-1-211R (SEQ ID NO:26) were selected from the clone 470-20-1 sequence (SEQ ID NO:106). These primers were used in amplification reactions with the SISPA-amplified PNF2161 cDNA as a template.

The identity of the amplified DNA fragments were confirmed by (i) size and (ii) hybridization with the specific oligonucleotide probe 470-20-1-152R (SEQ ID NO:27), designed based on the 470-20-1 sequence (SEQ ID NO:106). The probe was labelled with $^{32}P$ using T4 polynucleotide kinase and standard methods for 5'-end labelling. Hybridization to the amplified DNA was then performed using either Southern blot or liquid hybridization (Kumar, et al., 1989) analyses.

Positive control DNA used in the amplification reactions was previously amplified PCR product whose concentration was estimated by the Hoechst 33258 fluorescence assay, or, alternatively, purified plasmid DNA containing the cloned inserts of interest.

The 470-20-1 specific signal was detected in cDNA amplified by PCR from SISPA-amplified PNF2161. Negative control reactions were nonreactive, and positive control DNA templates were detected.

B. Genomic PCR

The term "genomic PCR" refers to testing for the presence of specific sequences in genomic DNA from relevant organisms. For example, a genomic PCR for a Mystax-derived clone would include genomic DNAs as follows:

1. human DNA (1 µg/rxn.)
2. Mystax DNA (0.1–1 µg/rxn.)
3. *E. coli* (10–100 ng/rxn.)
4. yeast (10–100 ng/rxn.)

Human and Mystax DNAs are tested, as the immediate and ultimate source for the agent. *E. coli* genomic DNA, as a frequent contaminant of commercial enzyme preparations, is tested. Yeast is also tested, as a ubiquitous organism, whose DNA can contaminate reagents and thus, be cloned.

In addition, a negative control (i.e., buffer or water only), and positive controls to include approximately $10^5$c/rxn., are also amplified.

Amplification conditions vary, as may be determined for individual sequences, but follow closely the following standard PCR protocol: PCR was performed in reactions containing 10 mM Tris, pH 8.3, 50 mM KCl, 1.75 mM $MgCl_2$, 1.0 uM each primer, 200 uM each DATP, dCTP, and dGTP, and 300 um dUTP, 2.5 units Taq DNA polymerase, and 0.2 units uracil-N-glycosylase per 100 ul reaction. Cycling was for at least 1 minute at 94° C., followed by 30 to 40 repetitions of denaturation (92°–94° C. for 15 seconds), annealing (55°–56° C. for 30 seconds), and extension (72° C. for 30 seconds). PCR reagents were assembled, and amplification reactions were constituted, in a specially-designated laboratory maintained free of amplified DNA. As a further barrier to contamination by amplified sequences and thus compromise of the test by "false positives," the PCR was performed with dUTP replacing TTP, in order to render the amplified sequences biochemically distinguishable from native DNA. To enzymatically render unamplifiable any contaminating PCR product, the enzyme uracil-N-glycosylase was included in all genomic PCR reactions. Upon conclusion of thermal cycling, the reactions were held at 72° C. to prevent renaturation of uracil-N-glycosylase and possible degradation of amplified U-containing sequences. A Hot Start PCR was performed, using standard techniques ("AMPLIWAX", Perkin-Elmer Biotechnology, Norwalk, Conn.; alternatively, manual techniques were used), in order to make the above general protocol more robust for amplification of diverse sequences, which ideally require different amplification conditions for maximal sensitivity and specificity.

Detection of amplified DNA was performed by hybridization to specific oligonucleotide probes located internal to the two PCR primer sequences and having no or minimal overlap with the primers. In some cases, direct visualization of electrophoresed PCR products was performed, using ethidium bromide fluorescence, but probe hybridization was in each case also performed, to help ensure discrimination between specific and non-specific amplification products. Hybridization to radiolabelled probes in solution was followed by electrophoresis in 8–15% polyacrylamide gels (as appropriate to the size of the amplified sequence) and autoradiography.

Clone 470-20-1 was tested by genomic PCR, against human, $E.$ $coli,$ and yeast DNAs. No specific sequence was detected in negative control reactions, nor in any genomic DNA which was tested, and $10^5$ copies of DNA/reaction resulted in a readily-detectable signal. This sensitivity (i.e., $10^5$/reaction) is adequate for detection of single-copy human sequences in reactions containing 1 ug total DNA, representing the DNA from approximately $1.5\times10^5$ cells.

All clones discussed herein have tested negative for human DNA, Mystax DNA (mystax derived clones only), $E.$ $coli,$ and yeast DNA using genomic PCR.

C. Direct Serum PCR

Serum or other cloning source or related source materials were directly tested by PCR using primers from selected cloned sequences. In these experiments, putative N(ABCDE) viral particles (DNA or RNA) were directly precipitated from sera with polyethylene glycol (PEG), or, in the case of PNF and certain other sera, were pelleted by ultracentrifugation. For DNA isolation, the pelleted materials were digested with proteinase k, followed by phenol/chloroform extraction and ethanol precipitation (Ausubel, et al.). For purification of RNA, the pelleted materials were dissolved in guanidinium thiocyanate and extracted by the acid guanidinium phenol technique (chomczynski, et al.). Alternatively, total nucleic acids were prepared by proteinase k/sodium dodecyl sulfate (SDS) digestion and phenol/chloroform extraction, followed by alcohol precipitation.

Isolated DNA was used directly as a template for the PCR. RNA was reverse transcribed using revere transcriptase (Gibco/BRL, Gaithersburg, Md.), and the cDNA product was then used as a template for subsequent PCR amplification.

In the case of 470-20-1, nucleic acid from the equivalent of 50 ul of PNF serum was used as the input template into each RT/PCR or PCR reaction. Primers were designed based on the 470-20-1 sequence, as follows: 470-20-1-77F (SEQ ID NO:25) and 470-20-1-211R (SEQ ID NO:26). Reverse transcription was performed using MMLV-RT (Gibco/BRL) and random hexamers (Promega, Madison, Wis.) by incubation at room temperature for approximately 10 minutes, 42° C. for 15 minutes, and 99° C. for 5 minutes, with rapid cooling to 4° C. The synthesized cDNA was amplified directly, without purification, by PCR, in reactions containing 1.75 mM $MgCl_2$, 1 uM each primer, 200 uM each dATP, dCTP, dGTP, and TTP, and 2.5 units Taq DNA polymerase ("AMPLITAQ", Perkin-Elmer, Norwalk, Conn.) per 100 ul reaction. Cycling was for at least one minute at 94° C., followed by 40–45 repetitions of denaturation (94° C. for 15 seconds for 10 cycles; 92° C. for 15 seconds for the succeeding cycles), annealing (55° C. for 30 seconds), and extension (72° C. for 30 seconds), in the "GENEAMP SYSTEM 9600" thermal cycler (Perkin-Elmer) or comparable cycling conditions in other thermal cyclers (Perkin-Elmer; MJ Research, Watertown, Mass.).

Positive controls consisted of previously amplified PCR product whose concentration was estimated using the Hoechst 33258 fluorescence assay, or purified plasmid DNA containing the DNA sequence of interest. In addition, an aliquot of positive control DNA corresponding to approximately 10–100 copies/rxn. was spiked into reactions containing nucleic acids extracted from the cloning source specimen, as a control for the presence of inhibitors of DNA amplification reactions. Each separate extract was tested at least once in this manner.

Specific products were detected by hybridization to a specific oligonucleotide probe 470-20-1-152R (SEQ ID NO:27), for confirmation of specificity. Hybridization of 10 ul of PCR product was performed in solution in 20 ul reactions containing approximately $1\times10^6$ cpm of $^{32}$P-labelled 470-20-1-152R. Specific hybrids were detected following electrophoretic separation from unhybridized oligo in polyacrylamide gels, and autoradiography.

In addition to PNF, extracted nucleic acids from several cloning source specimens were reverse transcribed and amplified, using the "serum PCR" protocol sequence. No signal was detected in GB (Mys3721), Mys29 (Post), Mys 131 (Post), Mys131 (Liver DNA from AT), Mys131 (Liver RNA from AT), Fulm. Hep. DNA (from JL), NMS, NHS, JS, SCH, MWT or Bonino. The specific signal in PNF serum was reproducibly detected in multiple extracts, with the 470-20-1 specific primers.

EXAMPLE 15

WESTERN BLOT ANALYSIS OF SERA PANELS

The antigens D6, and D19 were screened using panels of sera derived Mystax both prior and subsequent to innoculation with the GB agent and/or PNF. The antigens D6, D19, 1A and 17A were screened using panels of human sera derived both from individuals suffering from hepatitis and uninfected controls.

The antigen sj26-pGEX-GLI-1 was used as a control. This sample was determined to be at a concentration of 5 mg/ml using multiple assays, and was used as a standard for estimating the concentration of all other antigens tested.

Protein concentrations for all antigens were determined by a combination of determining the OD 280 nm of the protein fractions and by comparison to the protein standard described above. For all antigens 3 protein concentrations in the range of 0.5–3 ug/cm were fractionated using a 12.5% polyacrylimide gel and transferred onto nitrocellulose membrane. Typically 3–7 cm of membrane containing each protein concentration would be produced. The membrane was then blocked in a solution of "BLOTTO" (150 mM NaCl, 20 mM tris-HCl pH 7.5, 1% normal goat serum, 1% Bovine serum albumin, 1% non-fat dry milk (w/v) and 0.02% sodium azide) at least 1 hour. The membrane was then dried and cut into 1–2 mm strips. The strips containing different levels of blotted antigen were first rehydrated in TBS (150 mM NaCl; 20 mM Tris HCl, pH 7.5) then incubated overnight with test sera diluted in "BLOTTO" to which was added whole cell lysate of bacteria expressing non-recombinant pGEX-GLI at a dilution of 1/20 (v/v). Along with the strips containing test antigen, one strip containing 3 ug/cm of nonrecombinant pGEX-GLI was also incubated with test sera. Typical sera employed included Mystax 88 for clones D6, and D19 or JFA for 1A and 17A, rabbit anti-sj26 sera (diluted 1/1000), and two control sera derived from blood donors. After overnight incubation at 25° C. with gentle rocking, the strips were washed four times with TTBS (TBS plus 0.2–1.5% "TWEEN 20") and were then incubated with goatn anti-Human IgG (Promega, Madison, Wis.) conjugated to alkaline phosphatase diluted between 1/2000–1/7500 in "BLOTTO" for 1–2 hours at 25° C. with agitation, at which point the strips were washed 4 times with TBS. Bound antibody was detected by incubating the strips in a substrate solution containing BCIP and NBT in pH 9.8 phosphate buffer. Color development was allowed to proceed for ~15 minutes at which point color development was halted by 3 washed in distilled $H_2O$. The concentration of antigen that gave the strongest signal with the least amount of background or non-specific reactivity was determined and employed for all subsequent assays.

Prior to testing with human or Mystax sera 18×13 cm nitrocellulose membranes were prepared using the optimum antigen concentrations determined as described above. The antigens were fractionated, and transferred to nitrocellulose as described above. The antigens were fractionated, and transferred to nitrocellulose as described above. Prior to large scale testing, four strips from each of the membranes to be employed were pre-tested by incubation with positive and control data as described above. All membranes used in large-scale testing had to demonstrate immunoreactivity to positive control sera prior to use.

Assays with test sera were performed as is described above, with each sera to be tested being incubated with antigen containing pGEX-GLI strips up to 80 sera were tested in any one assay. Test sera were derived from the following groups of individuals and/or experimental animals.

(i) Serial bleeds from Mystax innoculated with the GB and PNF agents, (ii) sera from control Mystax not innoculated, (iii) sera from individuals who are infected with Hepatitis B virus by virtue of being positive for the presence of Hepatitis B surface antigen, (iv) sera from individuals infected with Hepatitis C virus by virtue of being reactive in a second-generation HCV ELISA assay, (v) sera from blood donors with an above-normal alanine aminotransferase (ALT) measurement, (vi) sera from normal blood donors and (vii) sera from individuals suffering from Non-A-E hepatitis.

The antigens D6 and D19 were strongly reactive only with the screening serum Mystax 88. Neither antigen was reactive with pre-inoculate sera from any of the four mystax that were inoculated with GB agent.

Table 11 presents the results obtained from testing the antigens D6, D19, 17A and 1A with human sera.

All human sera considered reactive with a particular antigen were tested at least twice against this antigen.

TABLE 11

REACTIVITY OF D6, D19, 1A AND 17A WITH HUMAN SERA

| Sera Type | D6 | D19 | 1A | 17A |
|---|---|---|---|---|
| HBV | 1/48 | 0/20 | 5/77 | 3/32 |
| HCV | 6/67 | 5/29 | 2/56 | 2/51 |
| ELV ALT/ | 1/24 | 0/20 | 1/54 | 0/20 |
| Non A–E Hepatitis | 7/112 | 0/23 | 19/155 | 1/47 |
| Random Donors | 2/54 | 1/40 | 1/78 | 4/36 |

EXAMPLE 16

IMMUNOSCREENING OF A DEN cDNA LIBRARY

A. Construction of DEN cDNA and DNA Libraries

A cDNA library was constructed, essentially as described in Example 2, using RNA isolated from DEN serum (Example 1).

A DNA library was constructed, essentially as described in Example 3, using DNA isolated from DEN serum.

The DEN cDNA source (ATCC 75417) and DNA source (ATCC 75418) libraries were deposited at the American Type Culture Collection, 12301 Parklawn Dr., Rockville, Md. 20852.

B. Immunoscreening and Characterization

The cDNA library of DEN in lambda gt11 was screened, as described in Example 4, with DEN serum. Two of the exogenous immunoreactive clones were selected and designated DR25-1 and 2DR8. The clones were sequenced. The sequences are presented as SEQ ID NO:51 and SEQ ID NO:103, respectively.

Clones DR25-1 and 2DR8 (i) tested positive for immunoreactivity in secondary plaque screening assays using DEN serum, (ii) was determined to be exogenous to human, mystax, and *E. coli* genomic DNA, (iii) was non-immunoreactive with normal human sera, and (iv) contained an open reading frame in frame with β-galactosidase.

The sequences of clones DR25-1 and 2DR8 were compared with "GENBANK" and EMBL database sequences at both nucleic acid and amino acid levels. The "GENBANK" search indicated that the sequences are unique as both nucleic acid and amino acid sequences.

EXAMPLE 17

IMMUNOSCREENING OF GB cDNA AND DNA LIBRARIES

A. Construction of GB cDNA and DNA Libraries

Two cDNA libraries were constructed, essentially as described in Example 2, using RNA isolated from My 620 and My 670 sera (Example 2) and adding E/A' linkers (SEQ ID NO:22 and SEQ ID NO:49) to both ends of the molecules.

Two DNA libraries were constructed, essentially as described in Example 3, using DNA isolated from My 620 and My 670 sera.

The cDNA and DNA source libraries were deposited at Genelabs Technologies, Incorporated, 505 Penobscot Drive, Redwood City, Calif. 94063.

B. Immunoscreening and Characterization

Twenty one clones (i) tested positive for immunoreactivity in the plaque screening assays using the mixture of convalescent sera from animals inoculated with GB agent, (ii) were determined to be exogenous to human, mystax, and *E. coli* genomic DNA, and (iii) were non-immunoreactive with pre-inoculum and/or normal sera. Further, the insert sequences were determined to be novel (i.e., they did not have significant sequence homology to any GENBANK sequences) and each contained an open reading frame continuous with the β-galactosidase coding sequence of the lambda gt11 vector.

Clones whose designations begin with "468" and "472" were isolated from cDNA libraries made from My 670 serum. Clones whose names begin with "474" or "486" were isolated from cDNA and DNA libraries, respectively, made from My 620 serum. Clones whose names begin with "475" were isolated from DNA libraries made from My 670 serum.

These clones are identified by SEQ ID NO:11 through SEQ ID NO:16, SEQ ID NO:39 through SEQ ID NO:43, and SEQ ID NO:74 through SEQ ID NO:83.

While the invention has been described with reference to specific methods and embodiments, it will be appreciated that various modifications and changes may be made without departing from the invention.

It is claimed:

1. A DNA composition containing Non-A Non-B Non-C Non-D Non-E Hepatitis Virus (N-ABCDE)-specific sequences useful for PCR detection of human N- (ABCDE) hepatitis agent nucleic acids, where N-(ABCDE) hepatitis agent is characterized by: (i) production of elevated serum alanine aminotransferase (ALT) levels in an infected primate, (ii) its serological distinction from hepatitis A virus (HAV), hepatitis B virus (HBV), hepatitis C virus (HCV), hepatitis D virus, and hepatitis E virus (HEV), and (iii) a viral genome comprising a polynucleotide region that is hybridizable with SEQ ID NO:106 under hybridization conditions that allow at most about 25–30% base pair mismatches.

* * * * *

SEQUENCE LISTING ( 1 ) GENERAL INFORMATION:

( i i i ) NUMBER OF SEQUENCES: 106

( 2 ) INFORMATION FOR SEQ ID NO:1:

( i ) SEQUENCE CHARACTERISTICS:
        ( A ) LENGTH: 234 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 427-7-1

( x i ) SEQUENCE DESCRIPTION: SEQ ID NO:1:

```
GAATTCGCGG  CCGCTCGACA  CAGGAGACAG  AGGGATACAC  ACAGGGGCAC  GGAAATAAAT     60
ACTGGACAGA  AAAGGATACA  CACAGGAGAG  TGGAGGAAAC  ACAAAGAAGA  AGAAGCATA     120
CACGGAGGAG  AAAAAAATAC  ACACAAAAGA  GGAAGATACA  CACAGAAAGG  AAAAGGATAC    180
ATAGAGGAAA  TGGAAATACA  CACAGGCGAC  ATGGGCCCGA  GCGGCCGCGA  ATTC          234
```

( 2 ) INFORMATION FOR SEQ ID NO:2:

( i ) SEQUENCE CHARACTERISTICS:
        ( A ) LENGTH: 133 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 430-2-14

( x i ) SEQUENCE DESCRIPTION: SEQ ID NO:2:

```
GAATTCCGGG  CCCTGCCACG  ACAGCTGCCT  TCCTGCACAA  AATGTCAAAG  CTCTTGATGG     60
CCTTAGCTTT  GCCTTTCTGG  AGAATGTTCT  AGACTGGCAT  GCTCCCGGTT  GTATAGCGAG    120
CGGCCGCGAA  TTC                                                            133
```

( 2 ) INFORMATION FOR SEQ ID NO:3:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 430-3-4

( x i ) SEQUENCE DESCRIPTION: SEQ ID NO:3:

```
GAATTCGCGG  CCGCTCGAAA  TACACACAGG  AGCGAGGGTG  ATGCACACAG  GAGTAAAAAA      60

AATACACAAA  GGAAAGACGA  GAATACACAC  AGGAGAGAGA  AAAATACACA  GAGGAGAGGG     120

GCGTACACAC  AGTAGAGAAA  AGGATACACG  AGCGGCCGCG  AATTC                     165
```

( 2 ) INFORMATION FOR SEQ ID NO:4:

( i ) SEQUENCE CHARACTERISTICS:
        ( A ) LENGTH: 216 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 430-4-8

( x i ) SEQUENCE DESCRIPTION: SEQ ID NO:4:

```
GAATTCGCGG  CCGCTCGGAT  CGGCAAGACA  GTGGAGGCAT  ACATAGACGA  TGTGGTCATT      60

AAAACCAGAC  ACGTCGACTC  CTTAATAGAC  GACTTGAGGC  TCACGGTCGA  CAATATCCGA     120

ACATACGACA  TTAAGCTCAA  TCCGGAAATA  TGCGTTTTCG  GCGTACCCGC  CGAAAAGCTC     180

CTGGGCTTCA  TCGTCTCCAC  GAGCGGCCGC  GAATTC                                 216
```

( 2 ) INFORMATION FOR SEQ ID NO:5:

( i ) SEQUENCE CHARACTERISTICS:
        ( A ) LENGTH: 204 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 428-2-3

( x i ) SEQUENCE DESCRIPTION: SEQ ID NO:5:

```
GAATTCGCGG  CCGCTCGTGC  AGCTATTCTT  ACTGGAGAAG  CAGCAGCGAG  TGTGAACATT      60

TCCGCAGGGG  ATGGGAAGAA  GGAAAAGCAG  TCACGGGGAC  ATTCCTCACC  CCAGGGGACC     120

AGTGATGCTC  CATTTAACGG  CACTAGCAGA  TCGAGTCCCA  TTTCTGCTTT  GAACAGAATG     180

TTCGAGCCGA  GCGGCCGCGA  ATTC                                               204
```

( 2 ) INFORMATION FOR SEQ ID NO:6:

( i ) SEQUENCE CHARACTERISTICS:
        ( A ) LENGTH: 150 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 428-3-1

(x i) SEQUENCE DESCRIPTION: SEQ ID NO:6:

| | | | | | |
|---|---|---|---|---|---|
| GAATTCGCGG | CCGCTCGGGG | GGAAGGGAAC | CACCAAGGTT | CTGCTGACTC | TCCTCTAAAT | 60
| GAATTTTTAT | TGTTTTGTTT | TTTGGTCAGT | TATGAGGAGT | CAAATCCAAA | GGATCCAGCG | 120
| GCAGTGACAG | AATCGAGCGG | CCGCGAATTC | | | | 150

( 2 ) INFORMATION FOR SEQ ID NO:7:

( i ) SEQUENCE CHARACTERISTICS:
        ( A ) LENGTH: 135 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 428-7-3

( x i ) SEQUENCE DESCRIPTION: SEQ ID NO:7:

| | | | | | |
|---|---|---|---|---|---|
| GAATTCGCGG | CCGCTCGGGC | AAGGCAATGT | AAGGCAAATC | CAGTGGAGGC | AAATCCAAAC | 60
| AAAACAATTC | CAGGAAAGGT | AAGGCAAGAC | AATGCAGGCA | AAGGCAATTC | CAGGCAAGAC | 120
| GAGCGCCGCG | AATTC | | | | | 135

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Sispa C linker ( x i ) SEQUENCE DESCRIPTION: SEQ ID NO:8:

CGAATTCGGC CAAGTCGGCC 20

( 2 ) INFORMATION FOR SEQ ID NO:9:

( i ) SEQUENCE CHARACTERISTICS:
        ( A ) LENGTH: 267 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: My 131 Clone 430-2-1

( x i ) SEQUENCE DESCRIPTION: SEQ ID NO:9:

| | | | | | |
|---|---|---|---|---|---|
| GAATTCGCGG | CCGCTCGGGA | GAGAAGGGGA | AAGCACACAG | GAGAGTGGAA | AGATACACAC | 60
| AGAAGAGAGA | AGGATACACA | CAAAAGAGAG | GAGGATACGC | ACAAGAAGAA | AAGTATACAC | 120

| | | | | | |
|---|---|---|---|---|---|
|ACAGGAAAGT|GTGATACACA|CATGAGAGAA|GGGTGTAAAT|ACAGGAGAGA|GGAGGATACA|180|
|CACAAAAGAG|TGGTGGGATA|CACAAGAAAA|GGAGAAGGAT|ACACACAGTA|GAGAGTAGAA|240|
|TACATAAAGG|CGAGCGGCCG|CGAATTC| | | |267|

(2) INFORMATION FOR SEQ ID NO:10:

(i) SEQUENCE CHARACTERISTICS:
        (A) LENGTH: 351 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (v) ORIGINAL SOURCE:
        (C) INDIVIDUAL ISOLATE: My 131 Clone 430-4-1

(xi) SEQUENCE DESCRIPTION: SEQ ID NO:10:

| | | | | | |
|---|---|---|---|---|---|
|GAATTCGCGG|CCGCTCGCAA|CAGCCAACAT|TCAAAGCAAC|TGATTTTCCA|AAAGTCCAGC|60|
|AAACAGTTGA|TGAATTTAGC|AAATTCATAC|TTTTTTTTCT|GCGTGCCCCT|ACCTATTACC|120|
|CTGCCTCTGC|CTCTACCTCT|TGAATATTCA|TCTCCAAATT|TCTATCAAAA|TGACCAATGG|180|
|AATTGAACAC|TAGTCAATGA|ATGGAGAATT|TACCAATGTC|ACTAACTTTA|TTCAGATCCC|240|
|CGCAGTAGTT|ATGGTAAAGT|GGGTGGGTTA|AGTGTTCTAA|CGGAATATTT|TAATTACTTA|300|
|TTTCATCCAA|TAGCACCCTG|ATATCTTATA|AACCCGAGCG|GCCGCGAATT|C|351|

(2) INFORMATION FOR SEQ ID NO:11:

(i) SEQUENCE CHARACTERISTICS:
        (A) LENGTH: 80 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (v) ORIGINAL SOURCE:
        (C) INDIVIDUAL ISOLATE: GB Clone 472-2-1

(xi) SEQUENCE DESCRIPTION: SEQ ID NO:11:

| | | | | | | | | | | | | | | | |
|---|---|---|---|---|---|---|---|---|---|---|---|---|---|---|---|
|GAA|TTC|GTT|ACA|CAG|GAA|AGA|GAA|GGT|ATA|CTC|ACG|GGA|GAA|AAG|AAA|48|
|ATA|CAC|AAA|GAA|GGG|CCA|CGC|CTA|GGG|AAT|TC| | | | | |80|

(2) INFORMATION FOR SEQ ID NO:12:

(i) SEQUENCE CHARACTERISTICS:
        (A) LENGTH: 153 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (v) ORIGINAL SOURCE:
        (C) INDIVIDUAL ISOLATE: GB Clone 474-19-3

( x i ) SEQUENCE DESCRIPTION: SEQ ID NO:12:

GAATTCCCTA GGCGTGGCAC ACAGGAGAGA GGAGGATACA CACAGGATAA GGGGATACAC 60

ACAGGAAAGA GGGATACACA AAGGAGAAAA GATACACACA GGAGAGAGCG GCATACGCAC 120

ATTAAAGGAT GATAAACAAA GGAGAACGAA TTC 153

( 2 ) INFORMATION FOR SEQ ID NO:13:

( i ) SEQUENCE CHARACTERISTICS:
        ( A ) LENGTH: 202 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 474- 6-3

( x i ) SEQUENCE DESCRIPTION: SEQ ID NO:13:

GAA TTC GTT ATA GGG GAA ACA GAA GGC CAA CAA GTT GGA GGA AAT CTT 48

GGA GAG GAA GAA AGT GTT AGG GAA GGA GAG AGG GGC TTC TTG TCA AGC 96

TCT AAT GTG AGG GAG TCG TAA GGA GGC TGA GAA TTG ACC ATT TAG TTG 144

ACA AGA CAG TTT GCT GGT GAC CGT GTT TCC CCT ATA AAT CCC CAC GCC 192

TAG GGA ATT C 202

( 2 ) INFORMATION FOR SEQ ID NO:14:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 475- 12-3

( x i ) SEQUENCE DESCRIPTION: SEQ ID NO:14:

GAA TTC GTT CGC ACC GAA GGT CAC GAC ACC CTT GAT ATC GAC CAG CTT 48

GCC CTG GGC GCT CAG CAC GGC CGA GGA ACT CAG CGT GCT CAC GCC GCC 96

CTG GTA GGA CGG ACG CAG GTA GCC CTC GCC GGA TGC GCC GTT GTC GGT 144

GAT GCC CGC CAG CAG GAC GTA GGG CGC CGA CAG CGA CAC GCT GTG GAT 192

CGG ATC CAT GCC GGC CGC GAC CCC ACG CCT AGG GAA TTC 231

( 2 ) INFORMATION FOR SEQ ID NO:15:

( i ) SEQUENCE CHARACTERISTICS:
        ( A ) LENGTH: 216 base pairs
        ( B ) TYPE: nucleic acid
        ( C ) STRANDEDNESS: double
        ( D ) TOPOLOGY: linear ( i i ) MOLECULE TYPE: DNA (iii) HYPOTHETICAL: NO (iv) ANTI-SENSE: NO (vi) ORIGINAL SOURCE:
    (C) INDIVIDUAL ISOLATE: GB Clone 475- 16-4

(xi) SEQUENCE DESCRIPTION: SEQ ID NO:15:

```
GAA TTC GTT AGA GAA AAG ACA TCC CTC TCC ATT TTT GGA GCA AAA CAT       48
CCT CAA AGC AGT GAA GTT AGA CCC ATT CAG AGG CTC CTG GAG GGA TTC       96
CCA AGG AAA CTG TCA GTG GGA ATG TGT GGA GCA AAA CAT CCT CAA AGC      144
AGT GAA GTT AGA CCC ATT CAG AGG CTC CTG GAG GGA TTC CCA AGG AAA      192
CTG TCA GCC ACG CCT AGG GAA TTC                                       216
```

(2) INFORMATION FOR SEQ ID NO:16:

(i) SEQUENCE CHARACTERISTICS:
        (A) LENGTH: 123 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: GB Clone 475- 3-3

(xi) SEQUENCE DESCRIPTION: SEQ ID NO:16:

```
GAA TTC TCT AAG TAC TAC TAC AAT CAA GAA ATT GAT CTA ACC AGT CTA       48
CTA GAC CTA GAT GAT CAA GAT GGT GAA AAT GCA TAC TGT AAG TAT CCA       96
AAA AGA TTT GAC AAC ATC AAT GAA TTC                                   123
```

(2) INFORMATION FOR SEQ ID NO:17:

(i) SEQUENCE CHARACTERISTICS:
        (A) LENGTH: 138 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: My 190 Clone D19

(xi) SEQUENCE DESCRIPTION: SEQ ID NO:17:

```
GAATTCGCGG CCGCTCGGGC ATTATTTTCA TTCGAGGACG TGCCTTCCTC TTTGCCTCCT      60
GCTGTCACTA ACATTTTGCA GGAGTTCGCT GACGTTTTTC CACAAGACGT GCCACCGGGA     120
TCGAGCGGCC GCGAATTC                                                   138
```

(2) INFORMATION FOR SEQ ID NO:18:

(i) SEQUENCE CHARACTERISTICS:
        (A) LENGTH: 181 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: My 190 Clone D20

(x i) SEQUENCE DESCRIPTION: SEQ ID NO:18:

| | | | | | | |
|---|---|---|---|---|---|---|
| GAATTCGCGG | CCGCTCGCAA | GCAAGATTCC | ACCAGCAAAA | AGAATCCATC | AGGACCTAGT | 60 |
| AAACATTGAG | GGGCCAGTAG | AAGCACTCTC | CTACCAGGCT | CATCCTGAAA | CCCCACTCCC | 120 |
| ACATCTAGGA | ATATCCAGGT | AGCTGTGTGC | CAGCCAGCAA | GGGGGCGAGC | GGCGCGAATT | 180 |
| C | | | | | | 181 |

(2) INFORMATION FOR SEQ ID NO:19:

(i) SEQUENCE CHARACTERISTICS:
(A) LENGTH: 22 base pairs
(B) TYPE: nucleic acid
(C) STRANDEDNESS: single
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: Sispa D linker (x i) SEQUENCE DESCRIPTION: SEQ ID NO:19:

GGCCGACTTG GCCGAATTCG TT                      22

(2) INFORMATION FOR SEQ ID NO:20:

(i) SEQUENCE CHARACTERISTICS:
(A) LENGTH: 304 base pairs
(B) TYPE: nucleic acid
(C) STRANDEDNESS: double
(D) TOPOLOGY: linear (i i) MOLECULE TYPE: DNA (i i i) HYPOTHETICAL: NO (i v) ANTI-SENSE: NO (v i) ORIGINAL SOURCE:
(C) INDIVIDUAL ISOLATE: My 190 Clone D30

(x i) SEQUENCE DESCRIPTION: SEQ ID NO:20:

| | | | | | | |
|---|---|---|---|---|---|---|
| GAATTCGCGG | CCGCTCGCGG | CGAAGCACCG | CCGGACGGAG | GATCCTCGTC | GCCGCCGTGT | 60 |
| GGAGGGAAGC | CACCATCCTC | GGAGCCCTGT | GAACGAGCAC | GAATCAGTCG | CCCAAGACTG | 120 |
| GAAAAATCAA | ACCGGGATGG | AACCTAACTT | GCGGGTCGGA | ACTACTGCAG | AAGTGGTGGC | 180 |
| TCTGGTGTCA | GCAACTGGCA | CGGCAGACGA | CCTCGGACCT | CGTGGCACTC | TGGCAAAGGC | 240 |
| ATGAGTGGTA | GTCCTGCCTC | TCCTCTCCTG | CATATCATCC | TGGAGCTCGA | GCGGCCGCGA | 300 |
| ATTC | | | | | | 304 |

(2) INFORMATION FOR SEQ ID NO:21:

(i) SEQUENCE CHARACTERISTICS:
(A) LENGTH: 135 base pairs
(B) TYPE: nucleic acid
(C) STRANDEDNESS: double (D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: My 190 Clone D44-2

(xi) SEQUENCE DESCRIPTION: SEQ ID NO:21:

| | | | | | |
|---|---|---|---|---|---|
| GAATTCGCGG | CCGCTCGGAT | CTTTCGGGCA | GGCCCGGTTG | ATGTGCTTGA | AATCAATGCA | 60 |
| CATTCGGAGC | GACTTGTCCT | TCTTAGGAAC | CATGACGACA | TTAGCGAGCC | ACTCGGAGCG | 120 |
| AGCGGCCGCG | AATTC | | | | | 135 |

(2) INFORMATION FOR SEQ ID NO:22:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Sispa E linker (xi) SEQUENCE DESCRIPTION: SEQ ID NO:22:

CGAATTCCCT AGGCGTGG                                                                 18

(2) INFORMATION FOR SEQ ID NO:23:

(i) SEQUENCE CHARACTERISTICS:
(A) LENGTH: 311 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: My 190 Clone D48

(xi) SEQUENCE DESCRIPTION: SEQ ID NO:23:

| | | | | | |
|---|---|---|---|---|---|
| GAATTCGCGG | CCGCTCGCTC | GCAGGCGGCG | GCAGGGGAGG | GGAGAAGGGG | AGGAGGAGGG | 60 |
| GTCCCGGCGG | CGGTGGCGCT | AGGGTTTCTC | CCATGACGCG | CGTCACGGGA | GGAGGACGGA | 120 |
| GGGGATTGTG | TTCGAATTAA | TTCGCGGCCG | CTCGGAACGC | GGCATCGAGT | GCAACCCAGT | 180 |
| GAAGATCAAG | GCCATAGAGA | GAACGGAGAT | TCCTACCAAG | CTGCGAGACA | TCCAAAAGTT | 240 |
| TACCGGGTGC | CTAGCCTCCC | TGAACCGCTT | CATCAGCCAG | GTAGGAGAGA | AGGCCGAGCG | 300 |
| GCCGCGAATT | C | | | | | 311 |

(2) INFORMATION FOR SEQ ID NO:24:

(i) SEQUENCE CHARACTERISTICS:
(A) LENGTH: 192 base pairs
(B) TYPE: nucleic acid
(C) STRANDEDNESS: double ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: My 190 Clone D5

( x i ) SEQUENCE DESCRIPTION: SEQ ID NO:24:

```
GAATTCGCGA  CCGCTCGGGA  AGAAAGCAAG  GGAAAGAATG  CCCCTCATCC  CTCTTATCTC      60
TCATCTCCTG  CCAGGGCTTG  CCATTGGCTT  AACCCAGTGG  ACAGAGAGCC  TGAATATGCA     120
GTCCATGTAA  ACCAACCTCC  TGGGGACCTG  TGGACAAGGG  CAAAGTGGGC  TCTGGCGAGC     180
GGCCGCGAAT  TC                                                             192
```

( 2 ) INFORMATION FOR SEQ ID NO:25:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer 470- 20-1-77F ( x i ) SEQUENCE DESCRIPTION: SEQ ID NO:25:

```
CTCTTTGTGT  AGTAGCCGAG  AGAT                                                24
```

( 2 ) INFORMATION FOR SEQ ID NO:26:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer 470- 20-1-211R ( x i ) SEQUENCE DESCRIPTION: SEQ ID NO:26:

```
CGAATGAGTC  AGAGGACGGG  GTAT                                                24
```

( 2 ) INFORMATION FOR SEQ ID NO:27:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO (v i) ORIGINAL SOURCE:
    (C) INDIVIDUAL ISOLATE: Primer 470- 20-1-152R (x i) SEQUENCE DESCRIPTION: SEQ ID NO:27:

TCGGTTACTG AGAGCAGCTC AGATGAG      27

(2) INFORMATION FOR SEQ ID NO:28:

(i) SEQUENCE CHARACTERISTICS:
        (A) LENGTH: 290 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: My 190 Clone D6-1

(x i) SEQUENCE DESCRIPTION: SEQ ID NO:28:

GAATTCGCGG CCGCTCGAAT ATGGTCTGGC GCCGAAGTCG ATGTTGATGC AGGGCATCGG      60
CGTGATGCGG TAAAGGCGTG GCAAAGCCTG AATTAATTCG CGGCCGCTCG CCCGTCCGTG     120
CAAAGTCAAA GGGCTAGATC CCGTGGTCAA ACGCTCCAGG GTTAGCCGGG ACGGGGCCC      180
TGGGGGGGAA GCAATGCCAT CGGAGCGTCG TACCGGGCCC TCATACATGC GGGGTGGTGT     240
TGTGGCATGT CTTAAGAGGC GACACGCGTC TCCCGAGCGG CCGCGAATTC                290

(2) INFORMATION FOR SEQ ID NO:29:

(i) SEQUENCE CHARACTERISTICS:
        (A) LENGTH: 185 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: My 190 Clone D64-1

(x i) SEQUENCE DESCRIPTION: SEQ ID NO:29:

GAATTCGCGG CCGCTCGGAA GGGTTTAGCA GACAAAGACA GCTGCCTCCC TAGACAGCCC      60
AAACAGGAAC TTCTCCAGAC AAGGACAGCC CAGCCTGACA GACCAGGGAA GGTTGGAGCA     120
GGGAGGCTCA GGAGCAAAGA CTTGAGTAAG AGTTAGGAGT TCCTGAGACG AGCGGCCGCG     180
AATTC                                                                 185

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
    (C) INDIVIDUAL ISOLATE: Primer 11F (x i) SEQUENCE DESCRIPTION: SEQ ID NO:30:

CACATGGCTG AATATCGACG                                                                                   20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: Primer 11R (x i) SEQUENCE DESCRIPTION: SEQ ID NO:31:

GGCAGACATG GCCTGCCCGG                                                                                   20

(2) INFORMATION FOR SEQ ID NO:32:

(i) SEQUENCE CHARACTERISTICS:
        (A) LENGTH: 145 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: My 190 Clone D24

(x i) SEQUENCE DESCRIPTION: SEQ ID NO:32:

GAATTCGCGG CCGCTCGGCC GGACTCCTCG TCATTGAAGC CAGGTTCAGG GGCTACTGAG          60

GGAGTCCTGG ACTAAGGGGT CCTCGGGCGT CCGGCCTGTT ACTCATTGGG CCAGACTGAT        120

GGGCTATGCG AGCGGCCGCG AATTC                                              145

(2) INFORMATION FOR SEQ ID NO:33:

(i) SEQUENCE CHARACTERISTICS:
        (A) LENGTH: 1062 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (v i) ORIGINAL SOURCE:
        (C) INDIVIDUAL ISOLATE: clone R27

(x i) SEQUENCE DESCRIPTION: SEQ ID NO:33:

GAAATTCGCG GCCGCTCGGG AGAAACAAGT GTGAGCAGCT GGTTTGCCGA GGGGAAGACA         60

GTGAATGGGG CTGGCTCTCA GGTGTGCGCA GAAGCCGGCC TTGGCACCGG GTTTGAGGAA       120

AGACAGGCTT ATTTTGGGCC CCACACAAGG AGCCAGGATC CGGCTCACAT CCGTCTCCCC       180

ATCCTGGCCG AGCGGCCGCG AATTAATTCG CGGCCGCTCG CAGGTCAGGG ATCCATGGGT       240

```
TTTTGCAACA  GAAGCCGTCC  ATGCTCTTCC  TCTGGAAGGT  GTAGCTTTTG  CTGTCAGGGT    300

GGCTGCTTTA  AATTCTCCCG  GGTGATGGTC  TGGATCTCGC  GGTCAGCAAT  TGGGGAAAGG    360

TGGGAAAGTG  TGTTACTGCT  CATTTCCGGG  GCCTTCTAGT  GCCTCAGGCT  GGGCTGTTCC    420

AGAAGGGCCC  ATTCTTTCCT  CAGACCTTGG  TCCTTCCCGG  GGAATAGTCC  TTCTCCCGTT    480

CTCAGCCAAG  TGGTCCACAT  AAGTGGCCCC  ATCCCTTCAA  GAGTAGGCCC  TGAACGGCTA    540

ATGGACCGAG  CGGCCGCGAA  TTAATTCGCG  GCCGCTCGCT  CAGGTTGCTG  ATAAATGTTT    600

ACTCATAGGC  CAGGCCTGCA  CAGGCCACAG  ACAAGGAGAG  GAAGCAGTTT  GTGGCTGGAG    660

AGTCGGACAG  TCCCACACCC  GCGCTCTGCT  GTGCTCTTGG  CCAGGCAGCC  TGGGAGAGGG    720

TGGCCCGAGC  GGCCGCGAAT  AATTCGCGGC  CGCTCGCTAG  AAGACCCGT  CGTCTCAGCC    780

CAAAATCTGC  TGAAACGGAT  AAGTAACTTC  AGCAAAGTCT  CAGGATACAA  AATCAATGTG    840

CAAAAGTCAC  AAGCATTCCT  ATACCTCAAT  AACAGACTTG  AAGAGTGCCA  AATCAAGAAC    900

GAACTGCCAT  TCACAATTGC  CGAGCGGCCG  CGAATTAATT  CAGATGTCAG  GACTGGAAAG    960

AGCACAGTAG  AAGGATGTCT  TAGGTCTTCC  ACTCTACAGA  AGAAAAAGAT  TCAGACCCAG   1020

TGTTTTCCAT  CCCACCCAGC  AACAGCGAGC  GGCCGCGAAT  TC                        1062
```

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 11F (JF)

( x i ) SEQUENCE DESCRIPTION: SEQ ID NO:34:

```
GGCGACGACT  CCTGGAGCC                                                       19
```

( 2 ) INFORMATION FOR SEQ ID NO:35:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Primer 11R (JF)

( x i ) SEQUENCE DESCRIPTION: SEQ ID NO:35:

```
CCAACTGGTA  ATGGTAGCG                                                       19
```

( 2 ) INFORMATION FOR SEQ ID NO:36:

( i ) SEQUENCE CHARACTERISTICS:
        ( A ) LENGTH: 624 base pairs
        ( B ) TYPE: nucleic acid
        ( C ) STRANDEDNESS: double (D) TOPOLOGY: linear (ii) MOLECULE TYPE: DNA (iii) HYPOTHETICAL: NO (iv) ANTI-SENSE: NO (vi) ORIGINAL SOURCE:
    (C) INDIVIDUAL ISOLATE: JFA Clone 17A21

(xi) SEQUENCE DESCRIPTION: SEQ ID NO:36:

```
GAATTCGCGG CCGCTCGGCC AGAAACGGCC TTGGAAAAGA AATTACGCCA AAACCAAGCA      60
GCGGTTGAAA AACGCAACGC GTTGGCCAAG AAAAATAGTG ACACCAGTGC GGCTAAAAAA     120
GGGCAGTCGA CGCACTTGTC ACCAGAACAG CAAGCCCTTG TTAAAAATTA TGGCTTACAG     180
CCAGCCCAGT ATCTCGCTTT CCAAGCCATG CCATTTCAGG CTTTTGGTGA TTCGGTCATG     240
TTAGATGCTG CGCCTTATCT ACAAGAAGTT AATCCACATA TGGTGGTGGA TGCGGCGGTT     300
GGTCGACAAC CTTATCAAAC GCCAAAAATC ATGGCGCAAG CCGCAGCCGC ACAACCATTA     360
GCAGATAATC TGCTCATTGG CTTAGGGACA AATGGGACGA TTAAGAAGCA AGACTTAGAT     420
CAAATTATGG CAATTGCCGG TAAAAAGCGT CAGGTCTATT GGATGAATAA CTTTGTGCAG     480
TCTCGTCCTT GGCAGGATAG TAACAATCAA TTGTTACAAA CCGCGCAGAA AACGTATAAG     540
AATTTGCACG TGGTTGATTG GTACGCAGTT GCCAAGCAAC ACGGTGACTG GTTTGCCGAT     600
GATGGGGCGA GCGGCCGCGA ATTC                                           624
```

(2) INFORMATION FOR SEQ ID NO:37:

(i) SEQUENCE CHARACTERISTICS:
        (A) LENGTH: 501 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: JFA Clone 1A2

(xi) SEQUENCE DESCRIPTION: SEQ ID NO:37:

```
GAATTCGCGG CCGCTCGCGA ACTCGTTGAG AGCCTCGACC ACCAGTGCGC ACTCATCGTT      60
ACTGATCCCC GTCGTCTTGA CGAGATCGTC GGCCTTCAAG CCCAGTCGGA CCGCCCCGTC     120
GTCGTCCTGC TCGCCACCGA CCCTGACGAC GCTCCTGACA AGCTTGCGGA AATTGTTGAC     180
GTTGTCGTCA CCCCTAACCC CCAGACCGAA CCTTGGGAAC ACCTCGGCGT CCCGGTGCAT     240
TCCATCGGCG TCCCGGCGAC TGGCGGCGGT CCGGCCCCTG GCGACCGCCC CAACCGAATT     300
GCCCTACTTG GCCCGTGCAC CGATGAGCAG CTTGCCGACG CTCTCCTCGC CTTCGACCAC     360
GCCTGCCAAG TTGTGCCCGG CTGGTCCTTG GAGATCTGCC TTGACGATGA ATCCAGAGCC     420
CGCTCGGCAG TGGCAGCCCG CCGCGACGTC GGTATTCACC CAGCTGGATC CGAAAACACG     480
GTTACGAGCG GCCGCGAATT C                                              501
```

(2) INFORMATION FOR SEQ ID NO:38:

(i) SEQUENCE CHARACTERISTICS:
        (A) LENGTH: 612 base pairs
        (B) TYPE: nucleic acid
        (C) STRANDEDNESS: double (D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: JFA Clone 4B11

(xi) SEQUENCE DESCRIPTION: SEQ ID NO:38:

| | | | | | | |
|---|---|---|---|---|---|---|
| GAATTCGCGG | CCGCTCGTGG | ACGCGGTCAT | CGAGTTCGAG | CGCCAGGCGC | TGCACGACTC | 60 |
| GACGTCCGAG | CGCGCGGCGG | TCTGAGGAGC | GGTGCCATGA | AGGACATCAC | CCTCTTTCCC | 120 |
| GCCGACATCG | CCGCAATGAC | CGTCGGCCAA | CTGGCCGCGT | TGCCCGCCGT | GCAGAAGGCC | 180 |
| GAGATCGACA | AGAACCGCGA | GCGGCCGCGA | ATTCGCGGCC | GCTCGCCCAA | AATATTTGCT | 240 |
| CGTAATTTGA | GATCTCTGCA | AAACAATGCA | CCTCCTGGCA | AAAACATCGA | TGTCAATTGT | 300 |
| TTGAACGTCA | ATTCTTGTTC | GTTGTCCGCA | AGCCCAAGCT | CACAAATTAA | CATGGCTTGT | 360 |
| AATGGAAACA | AGCAAGATCT | TCCCATACCG | TTTCCCCTGC | ACGAGCGGCC | GCGAATTCGC | 420 |
| GGCCGCTCGC | CCATCTCTTA | TAAGGACTCA | AATCTTTACG | TTAACGGCAA | GCAAGTTAAC | 480 |
| CAAGATTATA | TTGGGATTAA | TGAACGGACC | GAAGGCACAG | AGATGTCATT | TGGTAAGAAC | 540 |
| TGGTCATTAG | CGAGTCTGTC | AGCGAGTGAT | TTGTGGCAAA | AGAAGGATCG | TAACACGAGC | 600 |
| GGCCGCGAAT | TC | | | | | 612 |

(2) INFORMATION FOR SEQ ID NO:39:

(i) SEQUENCE CHARACTERISTICS:
(A) LENGTH: 333 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: GB Clone 478-4-1

(xi) SEQUENCE DESCRIPTION: SEQ ID NO:39:

| | | | | | | |
|---|---|---|---|---|---|---|
| GAATTCGTTC | GCCTGCTCGG | CGAGATACGC | GCGCGACAGG | ATCAGCGTGA | CGCCGGAGCC | 60 |
| GAGCAGCGCC | AGGATTTTCA | GGAACCGCGC | AAAATCATCG | ACAATAAAGC | TGCCGCCGAA | 120 |
| GGTCGTGAGC | TTGCCGCCGG | GCAGCCACAG | CACCAGGGCA | CCCGTGATAA | CGAGGAAAGC | 180 |
| AACCGCAAGA | CCGGTCACGA | GTTGTGTCGT | CTGCCCGCTG | CGAAACGCGC | CCAGCATCAG | 240 |
| CAGCGCCATG | GCGCCGGCGG | CCAGCGCCAG | TTCCGGCAGC | ACGGGGAGCA | GCGAATATCC | 300 |
| TGCGAAAGTC | ATAAGCCCAC | GCCTAGGGAA | TTC | | | 333 |

(2) INFORMATION FOR SEQ ID NO:40:

(i) SEQUENCE CHARACTERISTICS:
(A) LENGTH: 121 base pairs
(B) TYPE: nucleic acid
(C) STRANDEDNESS: double
(D) TOPOLOGY: linear (ii) MOLECULE TYPE: DNA (iii) HYPOTHETICAL: NO (i v) ANTI-SENSE: NO (v i) ORIGINAL SOURCE:
    (C) INDIVIDUAL ISOLATE: GB Clone 486- 17-5

(x i) SEQUENCE DESCRIPTION: SEQ ID NO:40:

```
GAATTCCCTA GGCGTGGGTC CAATTTATTT AGATGCAATA GTTGTGATTT GGAAATCACT      60

AAAGAGGATT TGATTAATTC AAATCAAGAA AACATAAATG CAAATCTCCA TGAAATTGAA     120

C                                                                     121
```

(2) INFORMATION FOR SEQ ID NO:41:

(i) SEQUENCE CHARACTERISTICS:
        (A) LENGTH: 213 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: GB Clone 486- 19-20

(x i) SEQUENCE DESCRIPTION: SEQ ID NO:41:

```
GAA TTC GTT GGT AAT AAG GTG GAG ATA GGT AAG AGT TGG CCT AAT AGG      48

GGC AAG CTA TTG AAG TTT GTT TAT GGA AAT GAG GAG GAG ACT AGT ACA      96

GGG GAT TTG GAG GCA AGG CGT AGA GAG AAG TGT CAG TCT TTA ATG GAG     144

GGC CCG CTT TGG TAG GGT AGC AGG GGC TGG AAC CCA GTG GCA GTG ACC     192

TGG GCC ACG CCT AGG GAA TTC                                         213
```

(2) INFORMATION FOR SEQ ID NO:42:

(i) SEQUENCE CHARACTERISTICS:
        (A) LENGTH: 183 base pairs
        (B) TYPE: nucleic acid
        (C) STRANDEDNESS: double
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: GB Clone 486- 19-21

(x i) SEQUENCE DESCRIPTION: SEQ ID NO:42:

```
GAA TTC GTT CTC CCA TTT CTG CCC AGC CAC ATC CTA TCA TGG TCA GCA      48

GCC AGC CCC AGC GCC ACC TTG GTG AAG CCT TCA GGG AGA CCT TGC CAT      96

CCC AGC AAG GGG CAC AGT AAG GAT GCC ACA GTC ACC CCA CCC CAC CCT     144

CAG GGC CAC CTC ATC TGG CAC CCC ACG CCT AGG GAA TTC                 183
```

(2) INFORMATION FOR SEQ ID NO:43:

(i) SEQUENCE CHARACTERISTICS:
        (A) LENGTH: 80 base pairs
        (B) TYPE: nucleic acid
        (C) STRANDEDNESS: double
        (D) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: GB Clone 486- 6-4

( x i ) SEQUENCE DESCRIPTION: SEQ ID NO:43:

```
GAA TTC CCT AGG CGT GGC CAG AAT ACA ACC AAA AAG AGA AAG AAA GGA        48

CCC CAA AGC AAT ACT AAT AAT CCA ACG AAT TC                             80
```

( 2 ) INFORMATION FOR SEQ ID NO:44:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: SISPA primer, top strand Linker AB ( x i ) SEQUENCE DESCRIPTION: SEQ ID NO:44:

```
GGAATTCGCG GCCGCTCG                                                    18
```

( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: Linker AB, bottom strand ( x i ) SEQUENCE DESCRIPTION: SEQ ID NO:45:

```
CGAGCGGCCG CGAATTCCTT                                                  20
```

( 2 ) INFORMATION FOR SEQ ID NO:46:

( i ) SEQUENCE CHARACTERISTICS:
        ( A ) LENGTH: 745 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: clone D12- 3

( x i ) SEQUENCE DESCRIPTION: SEQ ID NO:46:

```
GAATTCGCGG CCGCTCGCCA TGGAGATCAC CGCCGCAAAA GGAAGAAGGA GGGGTGGAGG       60

AGGGAGGAT CTAATGAGGC GACGAAATGG GGAGACGGTG GCGGCGAGA TCGGAAGCGG        120

AAGCCGGAAA CCCTAGCAAG GGGGAGAGAG AGCCGCCGAG CGGCCGCGAA TTAATTCGCG      180

GCCGCTCGGC TTTCCTTCTG TTGATCTACG CTTCGCCATC CCACGCTTC GCCCCCATGG       240
```

| | | | | | |
|---|---|---|---|---|---|
|CCGGGACTGC|TCTTCCGATT|GCGATGATAG|ACGCCCGCGG|CGGGGCCAGG|GGGCTCCGAG 300|
|CCTTGGCCCC|TGCCTTGCGG|CGGGTGCAGT|GGCCACCCAG|GTTCAAGCCA|GAAATGCAGA 360|
|GCCGGACATG|ATTCTTGTGT|TCAAGATCTA|CTTTGAAGTA|TTAGGAGAAG|GACCCCGCCT 420|
|TGCAATGCTG|AAGACAATCT|GCGCGTCGGA|CTCATCGTCA|TTGAAGCCTG|GTTCAGGGGC 480|
|TACTGAGGGA|GTCCTAGATT|AAGGGGTCCT|CGGATAGCCG|GCGAGCGGCC|GCGAATTAAT 540|
|TCGCGGCCGC|TCGTTAGAAT|CGTCCGGATC|AGTGTCAAAG|CTTGCATCGA|CGTAACCATT 600|
|TACGACTAGC|TCTTTGTCAC|CTCCATATAC|GAGAAACATA|TCCTTAGTCC|TTTTCAGGTA 660|
|TTTCAGGATG|TTCTTGACCG|TTGTCCAGTG|ATCCACTCCT|GGATTACTTT|GGTACCTACC 720|
|TGCCAAGCCG|AGCGGCCGCG|AATTC| | |745|

( 2 ) INFORMATION FOR SEQ ID NO:47:

( i ) SEQUENCE CHARACTERISTICS:
        ( A ) LENGTH: 201 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: clone D13

( x i ) SEQUENCE DESCRIPTION: SEQ ID NO:47:

| | | | | | |
|---|---|---|---|---|---|
|GAATTCGCGG|CCGCTCGGCA|GAATGCAGTT|GGCAGTTTTC|CCAACACTTA|CAGAACGAGC 60|
|TTGGTTGCAC|TGCCCTCCAA|AATGTGGACA|CCAGGCTTCT|CAGAGTCTGA|GCCTCAGACT 120|
|CCTCTCAGCT|CAGAGACATT|AGCACCAGCA|AGTGGCATCC|GCTCTTCAGA|GGCCCAAGCT 180|
|CCAGCGAGCG|GCCGCGAATT|C| | |201|

( 2 ) INFORMATION FOR SEQ ID NO:48:

( i ) SEQUENCE CHARACTERISTICS:
        ( A ) LENGTH: 519 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: clone D31- 2

( x i ) SEQUENCE DESCRIPTION: SEQ ID NO:48:

| | | | | | |
|---|---|---|---|---|---|
|GAATTCGCGG|CCGCTCGGGA|GAAGCAGAGG|AACCAGGGAA|GTATGGCGCG|GGCGATGGAA 60|
|GAATAACTGT|GGAGGTTGCG|GTGGCCGCGT|AGCCAGGCGG|ATTCCAAGGC|TGCGTGGGGA 120|
|AGCGGGGGCG|CCCACGTCCA|ATCAACCGCC|ACGCGAGCGG|CCGCGAATTA|ATTCGCGGCC 180|
|GCTCGCCTGT|TAAGGACGTG|CTAGAGAGCT|CCACCGGCAA|GAGCAAGAAG|TCCAAGGTTG 240|
|CACCACCAGA|AACTAAGAAG|GTCTCCGTCA|AGGAGGACGG|CACGGGCAGG|GCTTTCACTA 300|
|TAAGCTCCAC|GCTCGACAGC|AAATAGGAAA|GCCGAGCGGC|CGCGAATTAA|TTCGCGGCCG 360|
|CTCGGCATCA|GATCCAGCAG|CCGCCCCAGT|CGGTCTGCCT|CTGCATCGAC|CAGGCCCAAG 420|
|GCCCAGGGTG|AGCAGCCCCC|TGGCCTTTCC|TCTATTGGGC|TAGTCAATTT|CGGCCCGTAT 480|
|AGTGTTTTTT|TTCCTGCCTG|CGCGAGCGGC|CGCGAATTC| |519|

(  2 ) INFORMATION FOR SEQ ID NO:49:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: Sispa A'linker ( x i ) SEQUENCE DESCRIPTION: SEQ ID NO:49:

| | |
|---|---|
| CCACGCCTAG GGAATTCGTT | 20 |

(  2 ) INFORMATION FOR SEQ ID NO:50:

( i ) SEQUENCE CHARACTERISTICS:
( A ) LENGTH: 579 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( v i ) ORIGINAL SOURCE:
( C ) INDIVIDUAL ISOLATE: clone D76

( x i ) SEQUENCE DESCRIPTION: SEQ ID NO:50:

| | |
|---|---|
| GAATTCGCGG CCGCTCGCGA GCCTCCTCCT CGGCAGCTAG AACGAATGTC AGCTCGATCC | 60 |
| CCATCTGGGC AGGAGTCTAT GGAGACGCCA GATCCATGCT CTCTGGCTGC CGGAGAGTAT | 120 |
| GAACAACCAG AGCATGGTTG GCCGGGCGCC GATTCCGAGC TGCCGAGCGG CCGCGAATTC | 180 |
| AATTCGCGGC CGCTCGCGGT TAGGATCCCA TGAACCAGGA GCGCCAGCAC CGGTTCCTCG | 240 |
| ATCTTCCTAC TGGAGGCATG GTCATGGCTT TCATTCATTC ATTTCATTCT TAGTTCTGTT | 300 |
| GTGGAATCGA ACCGAGCGGC CGCGAATTAA TTCGCGGCCG CTCGCGAGCG GCCTCAAAGC | 360 |
| AACAGGCAGG AACCCTGCAG CTGTGATAGC GACGCAGGGC TTGCTGATAG CGTGCAGCAC | 420 |
| GCGTAGCAGC CCGAAGATGG TTCTCCTCGA GTAGCACGGC CGAGCGGCCG CGAATTAATT | 480 |
| CGCGGCCGCT CGGCCGGGGG TGGTGCGGCC ATGGCAAGCT GCTGAGCTAC GGGGACCACA | 540 |
| ATCGTCTCCT TCTTCTTCTT CACGAGCGGC CGCGAATTC | 579 |

(  2 ) INFORMATION FOR SEQ ID NO:51:

( i ) SEQUENCE CHARACTERISTICS:
( A ) LENGTH: 231 base pairs
( B ) TYPE: nucleic acid
( C ) STRANDEDNESS: double
( D ) TOPOLOGY: linear ( i i ) MOLECULE TYPE: DNA ( i i i ) HYPOTHETICAL: NO ( v i ) ORIGINAL SOURCE:
( C ) INDIVIDUAL ISOLATE: clone DR25- 1

( x i ) SEQUENCE DESCRIPTION: SEQ ID NO:51:

| | |
|---|---|
| GAATTCGCGG CCGCTCGGTA TCGTCCCGGC GCGGTGGATA TCACACCGGA ATCGCTGAAA | 60 |

-continued

```
TTCTGGATTG ACTATATCTC CGGAGGGACA GGGCGCTTCA TTTCCAAAAC CACGGATGCG        120

GCGGTGAAAT CGCTGAATGG TATTGATATA CCGGAACAGC AGGTGCCCTT CCTGGGGAAA        180

ATTTCGGGTG AGGTGATGCC GTATGCAGAC CAGCCGAGCG GCCGCGAATT C                231
```

( 2 ) INFORMATION FOR SEQ ID NO:52:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: Probe 1, 17A- 312F ( x i ) SEQUENCE DESCRIPTION: SEQ ID NO:52:

```
TATCAAACGC CAAAAATCAT GGCGCAAGCC GCAGCCGC                                 38
```

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: Probe 2, WT54-592F ( x i ) SEQUENCE DESCRIPTION: SEQ ID NO:53:

```
CATCAAGGAC CGTTGGGCGA TCGCCAGTAT                                          30
```

( 2 ) INFORMATION FOR SEQ ID NO:54:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: oligonucleotide primer 428-2-3F ( x i ) SEQUENCE DESCRIPTION: SEQ ID NO:54:

```
CGCCATGGCA GCTATTCTTA CTGGAGAA                                            28
```

( 2 ) INFORMATION FOR SEQ ID NO:55:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO 5,859,230

83
84
-continued (v i) ORIGINAL SOURCE:
　　(C) INDIVIDUAL ISOLATE: oligonucleotide primer 428-2-3R (x i) SEQUENCE DESCRIPTION: SEQ ID NO:55:

CGGGATCCCT ATTATCTGTT CAAAGCAGAA ATGGG　　　　　　　　　　　　　　　　35

(2) INFORMATION FOR SEQ ID NO:56:

(i) SEQUENCE CHARACTERISTICS:
　　　　(A) LENGTH: 25 base pairs
　　　　(B) TYPE: nucleic acid
　　　　(C) STRANDEDNESS: single
　　　　(D) TOPOLOGY: linear (i i) MOLECULE TYPE: DNA (i i i) HYPOTHETICAL: NO (v i) ORIGINAL SOURCE:
　　　　(C) INDIVIDUAL ISOLATE: oligonucleotide primer 17A-57F, 5'

(x i) SEQUENCE DESCRIPTION: SEQ ID NO:56:

GGCCATGGCG GCGGTTGAAA AACGC　　　　　　　　　　　　　　　　　　　　　　25

(2) INFORMATION FOR SEQ ID NO:57:

(i) SEQUENCE CHARACTERISTICS:
　　　　(A) LENGTH: 18 base pairs
　　　　(B) TYPE: nucleic acid
　　　　(C) STRANDEDNESS: single
　　　　(D) TOPOLOGY: linear (i i) MOLECULE TYPE: DNA (i i i) HYPOTHETICAL: NO (v i) ORIGINAL SOURCE:
　　　　(C) INDIVIDUAL ISOLATE: oligonucleotide primer 17A-602R, 3'

(x i) SEQUENCE DESCRIPTION: SEQ ID NO:57:

CCATCATCGG CAAACCAG　　　　　　　　　　　　　　　　　　　　　　　　　18

(2) INFORMATION FOR SEQ ID NO:58:

(i) SEQUENCE CHARACTERISTICS:
　　　　(A) LENGTH: 340 base pairs
　　　　(B) TYPE: nucleic acid
　　　　(C) STRANDEDNESS: double
　　　　(D) TOPOLOGY: linear (i i) MOLECULE TYPE: DNA (i i i) HYPOTHETICAL: NO (v i) ORIGINAL SOURCE:
　　　　(C) INDIVIDUAL ISOLATE: clone WT54

(x i) SEQUENCE DESCRIPTION: SEQ ID NO:58:

GCGGCCGCTC GCGATTAAGA AGCAAGACTT AGATCAAATT ATGGCAATTG CCGGTAAAAA　　60
GCGTCAGGTC TATTGGATGA ATAACTTTGT GCAGTCTCGT CCTTGGCAGG ATAGTAACAA　120
TCAATTGTTA CAAACCGCGC AGAAAACGTA TAAGAATTTG CACGTGGTTG ATTGGTACGC　180
AGTTGCCAAG CAACACGGTG ACTGGTTTGC CGATGATGGG GTACATCAAG GACCGTTGGG　240
CGATCGCCAG TATGTTCGGT TACTCGTTGA AACGGTGGGC CGCGTGTCAG GTGTTAAGTA　300
AACTACCGTC AGGTAGTTTT TTTATTTATT TGGGGTCTAG　　　　　　　　　　　　340

(2) INFORMATION FOR SEQ ID NO:59:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: oligonucleotide primer WT54-590F ( x i ) SEQUENCE DESCRIPTION: SEQ ID NO:59:

TACATCAAGG ACCGTTGGGC GATCG      25

( 2 ) INFORMATION FOR SEQ ID NO:60:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: oligonucleotide primer WT54-684R ( x i ) SEQUENCE DESCRIPTION: SEQ ID NO:60:

CTACCTGACG GTAGTTTACT TAACAC      26

( 2 ) INFORMATION FOR SEQ ID NO:61:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: oligonucleotide primer, 17A-215F ( x i ) SEQUENCE DESCRIPTION: SEQ ID NO:61:

CCAAGCCATG CCATTTCAGG      20

( 2 ) INFORMATION FOR SEQ ID NO:62:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: oligonucleotide primer, 17A-258F ( x i ) SEQUENCE DESCRIPTION: SEQ ID NO:62:

GGCCATGGAT GCTGCGCCTT ATCTACAAG      29

( 2 ) INFORMATION FOR SEQ ID NO:63:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA ( i i i ) HYPOTHETICAL: NO ( v i ) ORIGINAL SOURCE:
  ( C ) INDIVIDUAL ISOLATE: oligonucleotide primer, WT54-647R ( x i ) SEQUENCE DESCRIPTION: SEQ ID NO:63:

CCCACCGTTT CAACGAGTAA CCGAAC            26

( 2 ) INFORMATION FOR SEQ ID NO:64:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer KL- 1

( x i ) SEQUENCE DESCRIPTION: SEQ ID NO:64:

GCAGGATCCG AATTCGCATC TAGAGAT           27

( 2 ) INFORMATION FOR SEQ ID NO:65:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer KL- 2

( x i ) SEQUENCE DESCRIPTION: SEQ ID NO:65:

ATCTCTAGAT GCGAATTCGG ATCCTGCGA         29

( 2 ) INFORMATION FOR SEQ ID NO:66:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( v i ) ORIGINAL SOURCE:
    ( C ) INDIVIDUAL ISOLATE: oligonucleotide primer D6-NF ( x i ) SEQUENCE DESCRIPTION: SEQ ID NO:66:

CGCGCCATGG TATGGTCTGG CGCCGAAG          28

( 2 ) INFORMATION FOR SEQ ID NO:67:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: oligonucleotide primer D6-BR ( x i ) SEQUENCE DESCRIPTION: SEQ ID NO:67:

CGCGGGATCC CTATTACGTT TGACCACGGG ATCTAG        36

( 2 ) INFORMATION FOR SEQ ID NO:68:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: oligonucleotide primer D19-NF ( x i ) SEQUENCE DESCRIPTION: SEQ ID NO:68:

CGCGCCATGG CATTATTTTC ATTCGAGGAC G        31

( 2 ) INFORMATION FOR SEQ ID NO:69:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: oligonucleotide primer D19-BR ( x i ) SEQUENCE DESCRIPTION: SEQ ID NO:69:

CGCGGGATCC CTATTATCCC GGTGGCACGT CTTGTG        36

( 2 ) INFORMATION FOR SEQ ID NO:70:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( v i ) ORIGINAL SOURCE:
        ( C ) INDIVIDUAL ISOLATE: oligonucleotide primer 17A-NF, 5'

( x i ) SEQUENCE DESCRIPTION: SEQ ID NO:70:

CGGCCATGGA ATTCCCAGAA ACGGCCTTGG        30

( 2 ) INFORMATION FOR SEQ ID NO:71:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: oligonucleotide primer 17A-BR, 3'

( x i ) SEQUENCE DESCRIPTION: SEQ ID NO:71:

CCCGGATCCG AATTCTTACC CATCATCGGC AAACCAG        37

( 2 ) INFORMATION FOR SEQ ID NO:72:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: oligonucleotide primer 1A-NF, 5'

( x i ) SEQUENCE DESCRIPTION: SEQ ID NO:72:

CGGCCATGGA ATTCGAACTC GTTGAGAGC        29

( 2 ) INFORMATION FOR SEQ ID NO:73:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( i i ) MOLECULE TYPE: DNA ( i i i ) HYPOTHETICAL: NO ( v i ) ORIGINAL SOURCE:
      ( C ) INDIVIDUAL ISOLATE: oligonucleotide primer 1A-BR, 3'

( x i ) SEQUENCE DESCRIPTION: SEQ ID NO:73:

CCCGGATCCG AATTCTTAAA CCGTGTTTTC GGATCC        36

( 2 ) INFORMATION FOR SEQ ID NO:74:

( i ) SEQUENCE CHARACTERISTICS:
      ( A ) LENGTH: 109 base pairs
      ( B ) TYPE: nucleic acid
      ( C ) STRANDEDNESS: double
      ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
      ( C ) INDIVIDUAL ISOLATE: GB Clone 487- 13-5

( x i ) SEQUENCE DESCRIPTION: SEQ ID NO:74:

GAATTCCCTA GGCGTGGGGC ATCGCTATCA AAAAGTGATG CGTCAGGTTC ATCGGGGCAG    60

AATCGGAAGC CATATGCCTC CGATTTTACT GGCCGTCGAC AACGAATTC    109

( 2 ) INFORMATION FOR SEQ ID NO:75:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 14-11

( x i ) SEQUENCE DESCRIPTION: SEQ ID NO:75:

GAATTCCCTA GGCGTGGGGT CAGGGTCTCG CCCATCGGCA TCGTGACCGG CGCGGCGCCG    60

GGGCGCGTCA ATTCCACGCG TACCACGCGC ACCGGCTGGC CCAGGTAGGC GGCATCGAAC    120

GAATTC    126

( 2 ) INFORMATION FOR SEQ ID NO:76:

( i ) SEQUENCE CHARACTERISTICS:
        ( A ) LENGTH: 174 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 14-15

( x i ) SEQUENCE DESCRIPTION: SEQ ID NO:76:

GAA TTC CCT AGG CGT GGG GAA CAA CAG TAT GAA GAT GTT CTA CAT GGG    48

GCC AAG TCG GTA TCT AAG ATT GTC ACC GAC TCT TCA GAT GAT GTC TTA    96

GCT AAG CAA AAG GTC TAT GAA GGA TCT AAG GGT GAT AAC CTA GTC ATG    144

ACC ATG GAC ATC GAT TTC CAG AAC GAA TTC    174

( 2 ) INFORMATION FOR SEQ ID NO:77:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 15-7

( x i ) SEQUENCE DESCRIPTION: SEQ ID NO:77:

GAA TTC CCT AGG CGT GGG GAA GAG AAG ATG AGA AAT GAC AGA AAA GAA    48

```
AAT AAA CAA ATT AAA TTG AAG TAT CAA CAA AAA ATG GAA GAC AAC GAA        96

TTC                                                                     99
```

( 2 ) INFORMATION FOR SEQ ID NO:78:

( i ) SEQUENCE CHARACTERISTICS:
        ( A ) LENGTH: 163 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 19-7

( x i ) SEQUENCE DESCRIPTION: SEQ ID NO:78:

```
GAA TTC GTT ATA GGG AAA TCC AAA GAC AAC AGT GAA AAC ATA AAC AAG        48

AAC AGT AGA AGA AAT CTT TAG GGA AAT CCA AAG ACA ACA GTG AAA ACA        96

TAA ACA AGA ACA GTA GAA GAA AAT TTA GCC TAA GAT AGA GAA GAC ATG       144

GTC CAC GCC TAG GGA ATT C                                             163
```

( 2 ) INFORMATION FOR SEQ ID NO:79:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 4-1

( x i ) SEQUENCE DESCRIPTION: SEQ ID NO:79:

```
GAA TTC CCT AGG CGT GGC GAT AAC ACG ATT TCT AAC AAT GCA GCC AAG        48

CAG GTG TTT GAA GGC TTG TGG GCG GGC GAG GGC GAG GTA GAC GCG ATT        96

ATC GAA GCC AAA GGC CTC AAG CAG GTG TCT GAT ACA GGC GCG ATT GAA       144

CGA ATT C                                                             151
```

( 2 ) INFORMATION FOR SEQ ID NO:80:

( i ) SEQUENCE CHARACTERISTICS:
        ( A ) LENGTH: 165 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 6-1

( x i ) SEQUENCE DESCRIPTION: SEQ ID NO:80:

```
GAATTCGTTG  TTCGTCGTGT  GACCGGTCGG  TCAGAACCTC  GGGTGGTTAC  CCAGCAGCAG        60

CGCTCGCTCA  TCGGCGACGT  CCTTGCCCGC  AGCCTTCTTG  ACCGTGCCGA  GAGTCCAGCA       120

GTCGATGTGG  CGTGCGGTCA  GTACCGCCCC  ACGCCTAGGG  AATTC                       165
```

( 2 ) INFORMATION FOR SEQ ID NO:81:

( i ) SEQUENCE CHARACTERISTICS:
        ( A ) LENGTH: 125 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 6-10

( x i ) SEQUENCE DESCRIPTION: SEQ ID NO:81:

```
GAA  TTC  GTT  CGG  ACA  GCT  CGC  CAA  CCT  CAA  CCA  GAT  GAC  GTC  GCA  GAG    48

CTC  GGC  CGG  CGC  CTC  CGT  CAT  CAC  CCT  GCA  GTT  CAG  CCT  GGA  TCT  CGC    96

CCT  CGA  CAT  CGC  CCA  CAC  CTA  GGG  AAT  TC                                  125
```

( 2 ) INFORMATION FOR SEQ ID NO:82:

( i ) SEQUENCE CHARACTERISTICS:
        ( A ) LENGTH: 229 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 6-2

( x i ) SEQUENCE DESCRIPTION: SEQ ID NO:82:

```
GAA  TTC  CCT  AGG  CGT  GGA  GAA  AGT  TCT  AGT  GGT  CTG  GAT  AAA  AGA  TCA    48

AAT  CAG  CCC  CAA  CAA  GCC  CTT  AAG  CCA  AAA  CCT  AAT  CCA  GGG  CAA  GGC    96

TCT  AGA  AAG  TTC  TAG  TGG  TCA  CCG  AAT  TCC  CTA  GGC  GTG  GGA  ACA  TGA   144

CAC  ACC  CGG  CCA  TGA  GAT  AAA  TCA  CAT  TCA  GTG  CCA  TAT  TAA  AAA  AAA   192

TTA  ATG  CAA  ACA  AAA  GTC  CAT  TAT  CAA  CAA  CGA  ATT  C                    229
```

( 2 ) INFORMATION FOR SEQ ID NO:83:

( i ) SEQUENCE CHARACTERISTICS:
        ( A ) LENGTH: 151 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: GB Clone 487- 9-2

( x i ) SEQUENCE DESCRIPTION: SEQ ID NO:83:

| GAA | TTC | CCT | AGG | CGT | GGC | GAT | AAC | ACG | ATT | TCT | AAC | AAT | GCA | GCC | AAG | 48 |
| CAG | GTG | TTT | GAA | GGC | TTG | TGG | GCG | GGC | GAG | GGC | GAG | GTA | GAC | GCG | ATT | 96 |
| ATC | GAA | GCC | AAA | GGC | CTC | AAG | CAG | GTG | TCT | GAT | ACA | GGC | GCG | ATT | GAA | 144 |
| CGA | ATT | C | | | | | | | | | | | | | | 151 |

( 2 ) INFORMATION FOR SEQ ID NO:84:

( i ) SEQUENCE CHARACTERISTICS:
        ( A ) LENGTH: 105 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SC1-2

( x i ) SEQUENCE DESCRIPTION: SEQ ID NO:84:

| GAA | TTC | GCG | GCC | GCT | CGA | GGC | TGC | GGT | GGA | CAG | AGA | TCA | GGC | CAT | TCC | 48 |
| AAG | GCG | AAC | AAA | GCT | TCA | TAC | GCT | TCT | CCA | AGT | CAT | CCC | AAC | CCG | CGA | 96 |
| GAG | GAA | TTC | | | | | | | | | | | | | | 105 |

( 2 ) INFORMATION FOR SEQ ID NO:85:

( i ) SEQUENCE CHARACTERISTICS:
        ( A ) LENGTH: 123 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SC5-2

( x i ) SEQUENCE DESCRIPTION: SEQ ID NO:85:

| GAA | TTC | CTT | GAC | GAA | GAA | GAG | GAG | GCG | CTC | TAC | CTC | AGC | GCG | CAA | TTG | 48 |
| AAC | TTG | AGC | GAG | CGC | GCC | CGC | GAA | CTC | GTT | CAG | CGG | TTC | GAA | CTG | GGC | 96 |
| GAA | GGC | GTC | ACG | AGC | GGC | CGC | GAA | TTC | | | | | | | | 123 |

( 2 ) INFORMATION FOR SEQ ID NO:86:

( i ) SEQUENCE CHARACTERISTICS:
        ( A ) LENGTH: 229 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU1-1

( x i ) SEQUENCE DESCRIPTION: SEQ ID NO:86:

| | | | | | | | | | | | | | | | | |
|---|---|---|---|---|---|---|---|---|---|---|---|---|---|---|---|---|
| GAA | TTC | GCG | GCC | GCT | CGG | CGG | GAT | GGC | ACA | AGG | CTC | AAC | TCT | TCT | TCG | 48 |
| ACG | CAA | ACA | TTC | TAA | CAG | AAC | GGA | TCG | GGA | ACA | AAC | AAA | CTT | CGC | CGC | 96 |
| GCG | CTT | CAT | TGC | GCG | TCC | GGT | GCT | GAA | CGC | GCC | CGC | GTC | GAA | CTC | GAG | 144 |
| CCT | GTG | ATG | ACG | GGC | GAT | TCA | CCC | ATG | CTT | CGC | GTT | GCG | GAG | AAT | GCA | 192 |
| AGC | CGG | TCC | CTC | TCG | CGG | CTC | GAG | CGG | CCG | CGA | ATT | C | | | | 229 |

( 2 ) INFORMATION FOR SEQ ID NO:87:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU2-10

( x i ) SEQUENCE DESCRIPTION: SEQ ID NO:87:

| | | | | | | | | | | | | | | | | |
|---|---|---|---|---|---|---|---|---|---|---|---|---|---|---|---|---|
| GAA | TTC | GCG | GCC | GCT | CGA | CCC | ATC | GCG | CTC | CGG | CGT | CGG | GAT | CAG | ACG | 48 |
| GCG | TAT | GTT | GTA | GAA | GAC | GAT | CTC | GCG | TGT | TGC | GAC | GAA | GAA | CCC | ATC | 96 |
| GCG | CTC | CGG | CGT | CGG | GAT | CAG | ACG | GCG | TAT | GTT | GTA | GCC | TTC | CAT | GCC | 144 |
| GAA | AAG | CTT | CTG | CGG | ACG | CTG | GCC | CGG | AAT | GAA | CGA | GTA | GAC | GAA | CCC | 192 |
| GCT | GAT | GTA | GTA | AAC | GAT | GTC | GCG | AGC | GGC | CGC | GAA | TTC | | | | 231 |

( 2 ) INFORMATION FOR SEQ ID NO:88:

( i ) SEQUENCE CHARACTERISTICS:
        ( A ) LENGTH: 358 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU2-4

( x i ) SEQUENCE DESCRIPTION: SEQ ID NO:88:

| | | | | | | | | | | | | | | | | |
|---|---|---|---|---|---|---|---|---|---|---|---|---|---|---|---|---|
| GAA | TTC | GCG | GCC | GCT | CGG | TCC | GAA | GTT | GAC | ACA | AGC | ATG | AAG | TCA | AGT | 48 |
| GGT | CCA | AGG | CAA | CTG | ACT | TCT | GAA | CGT | TCA | GTT | AGA | ACC | CCA | AGG | AGA | 96 |
| ACT | GCA | AAT | GAA | CAT | TTG | TCG | TCG | CAT | ATT | GGC | AGC | TTC | CGT | TCT | GTC | 144 |
| TGC | GTC | TCT | CAC | CCT | TCC | TGT | CTT | AGC | GGG | CGA | GAT | GGA | CAC | CGG | TTA | 192 |
| TAC | ACC | ACC | ACC | GCC | AAC | CAC | CAA | CGC | TGC | GGG | CGA | GAT | GGA | CAC | TGG | 240 |
| CTA | TGC | CGG | GCA | GAT | GGA | CAC | GGG | CTA | CGC | GGG | AGA | GAT | GGG | CAC | TGG | 288 |
| AGC | AGC | TCA | AAC | ATC | ATC | TGC | TAG | CTC | GAT | CAC | AGA | GAT | TTT | GCT | TCT | 336 |
| TAT | CAC | GAG | CGG | CCG | CGA | ATT | C | | | | | | | | | 358 |

( 2 ) INFORMATION FOR SEQ ID NO:89:

( i ) SEQUENCE CHARACTERISTICS:
        ( A ) LENGTH: 300 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU2-5

( x i ) SEQUENCE DESCRIPTION: SEQ ID NO:89:

| | | | | | | | | | | | | | | | | |
|---|---|---|---|---|---|---|---|---|---|---|---|---|---|---|---|---|
| GAA | TTC | GCG | GCC | GCT | CGG | CGG | GTC | AAT | GAG | AGC | GCA | GGC | AAC | CGG | CAC | 48 |
| CCG | GAA | GTG | ATC | CCA | ACT | GGC | AAT | CAG | CAA | CAC | CAT | CTC | AAA | GCC | GAA | 96 |
| CGA | GAA | GCG | GGC | GTA | CTC | GTT | CAT | GCG | GCA | TTT | GCG | CCC | GAG | CGG | GTG | 144 |
| TTT | CTC | ACC | ACG | TTT | CCC | CTT | AAG | TGT | CGC | GTC | ACC | GAT | CAG | ATG | CAG | 192 |
| GGT | GGC | ATC | CTG | GGG | CGG | AGG | CAA | AAG | GCG | CAA | GGT | GTC | GGC | GCT | CAA | 240 |
| CTC | TTT | AAC | CAG | TGC | TCG | TTC | ATC | CCA | CCA | GCC | GCT | TCT | GAC | CCG | AGC | 288 |
| GGC | CGC | GAA | TTC | | | | | | | | | | | | | 300 |

( 2 ) INFORMATION FOR SEQ ID NO:90:

( i ) SEQUENCE CHARACTERISTICS:
        ( A ) LENGTH: 342 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU2-7

( x i ) SEQUENCE DESCRIPTION: SEQ ID NO:90:

| | | | | | | | | | | | | | | | | |
|---|---|---|---|---|---|---|---|---|---|---|---|---|---|---|---|---|
| GAA | TTC | GCG | GCC | GCT | CGG | GCC | ATT | GAA | CAG | GAT | TAT | CCT | GCT | CCG | AAA | 48 |
| CAG | AGG | GAA | GAG | CAT | ACC | CCT | GAT | AAA | CAA | CCT | CTC | TCT | TCC | AAC | ATA | 96 |
| CAA | ACT | GAT | TCC | GTG | GAT | CCT | GAA | CAG | AGC | AAT | CCG | AAC | CGT | TTC | TGT | 144 |
| CTT | CTG | TGC | AAA | GAA | TTT | TAT | GGT | TTC | AGG | TAC | ATC | TTC | GAT | AAC | AAC | 192 |
| GGA | AAC | ACC | GTT | GTT | CGT | CGC | TGC | TCA | CAC | GTC | CCC | GAA | GTA | GAG | AAG | 240 |
| AGG | TTC | AAG | CCC | TCG | GGA | AAC | CTC | TCC | CAG | TCA | TAG | ACC | CCA | CGC | CTA | 288 |
| AAG | GCG | GGG | GCT | TGC | GGG | TAT | GAC | CCG | GCA | AGC | CTG | TCG | AGC | GGC | CGC | 336 |
| GAA | TTC | | | | | | | | | | | | | | | 342 |

( 2 ) INFORMATION FOR SEQ ID NO:91:

( i ) SEQUENCE CHARACTERISTICS:
        ( A ) LENGTH: 122 base pairs
        ( B ) TYPE: nucleic acid
        ( C ) STRANDEDNESS: double
        ( D ) TOPOLOGY: linear ( i i ) MOLECULE TYPE: DNA (  i i i ) HYPOTHETICAL: NO (  i v ) ANTI-SENSE: NO (  v i ) ORIGINAL SOURCE:
    ( C ) INDIVIDUAL ISOLATE: SCH Clone SU2-9

(  x i ) SEQUENCE DESCRIPTION: SEQ ID NO:91:

| GAA | TTC | GCG | GCC | AGT | CGA | GCC | ACG | GAA | ATT | CAC | TTG | CAG | CAC | GGC | GTA | 4 8 |
| GCC | ACG | GTT | AGC | GAG | CCA | CTG | AAC | CAT | CGG | GTT | ATA | GCC | CCA | CGT | GTC | 9 6 |
| GCG | CGA | CCA | CGA | GCG | GCC | GCG | AAT | TC  |     |     |     |     |     |     |     | 1 2 2 |

( 2 ) INFORMATION FOR SEQ ID NO:92:

(  i ) SEQUENCE CHARACTERISTICS:
    ( A ) LENGTH: 305 base pairs
    ( B ) TYPE: nucleic acid
    ( C ) STRANDEDNESS: double
    ( D ) TOPOLOGY: linear (  i i ) MOLECULE TYPE: DNA (  i i i ) HYPOTHETICAL: NO (  i v ) ANTI-SENSE: NO (  v i ) ORIGINAL SOURCE:
    ( C ) INDIVIDUAL ISOLATE: SCH Clone SU4-3

(  x i ) SEQUENCE DESCRIPTION: SEQ ID NO:92:

| GAA | TTC | GCG | GCC | GCT | CGG | GGG | CAC | GCA | CAT | GCT | GAA | GCG | AGG | GTA | ACA | 4 8 |
| ACG | ACA | ACG | TCG | AAT | CAG | ACG | GGC | AGC | AGG | AGT | GCT | GAT | ACG | CCA | AAG | 9 6 |
| AGC | GCA | GGA | AGT | TGG | AAG | TTT | GAC | CCG | AAG | GTG | GAT | TTG | GAT | TGG | CGC | 1 4 4 |
| GGT | ACT | GGC | AAA | ACT | GTT | AGG | GAA | GCA | GTG | GAT | GAG | GCT | TTC | AAA | CGC | 1 9 2 |
| ACT | GGT | GTT | CCT | AAA | GAG | GAT | TTC | GAG | GTA | ACG | AAA | TGG | GCC | GTT | GAT | 2 4 0 |
| AAA | AAT | GGC | AAA | AGT | TTT | CCT | GTC | GAA | TGG | AGA | GCA | AAA | GGT | GGA | GCA | 2 8 8 |
| CGA | GCG | GCC | GCG | AAT | TC  |     |     |     |     |     |     |     |     |     |     | 3 0 5 |

( 2 ) INFORMATION FOR SEQ ID NO:93:

(  i ) SEQUENCE CHARACTERISTICS:
    ( A ) LENGTH: 240 base pairs
    ( B ) TYPE: nucleic acid
    ( C ) STRANDEDNESS: double
    ( D ) TOPOLOGY: linear (  i i ) MOLECULE TYPE: DNA (  i i i ) HYPOTHETICAL: NO (  i v ) ANTI-SENSE: NO (  v i ) ORIGINAL SOURCE:
    ( C ) INDIVIDUAL ISOLATE: SCH Clone SU4-4

(  x i ) SEQUENCE DESCRIPTION: SEQ ID NO:93:

| GAA | TTC | GCG | GCC | GCT | CGG | CGG | GCG | CTA | GAG | GCC | GGC | GCT | TTG | TTG | CAC | 4 8 |
| GAT | ATC | GGC | AAA | CTC | GCC | GTG | CCC | GAA | TAC | ATT | CTG | AAC | AAG | CCG | GGC | 9 6 |
| AAA | TTG | ACC | GCG | GCC | GAG | TTT | GAG | AAG | ATG | AAA | GTC | CAC | ACG | GTG | GTC | 1 4 4 |
| GGT | GCC | GAC | ATC | GTC | CGG | CGC | GTT | GGA | TTT | CCT | TAC | CCG | GTG | GAA | GAC | 1 9 2 |
| ATC | GTC | CGC | TAC | CAC | CAC | GAG | AAA | TGG | GAC | GCG | AGC | GGC | CGC | GAA | TTC | 2 4 0 |

( 2 ) INFORMATION FOR SEQ ID NO:94:

( i ) SEQUENCE CHARACTERISTICS:
        ( A ) LENGTH: 318 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU5-4

( x i ) SEQUENCE DESCRIPTION: SEQ ID NO:94:

```
GAA TTC GCG GCC GCT CGG CGG GCA CTG CTA CAA TTT GCA CAG AGT CAA        48
TAT CCT GAT GGT AAA GTT TCT GTG GTG ATT GGT GCA CCA GGC AAT AAA        96
GGT GTG TCA CGC CGT GCT GAC TTT GGT CGG GTG GTG TCA GAG TTT GCG       144
GAT ACG GTC TTT TTG ACG GCT GAT GAT CCA CAA TTT GAA TCG CCA ATG       192
GCC ATT GCC AAA GAA ATT GCG GCC CAC ATT ACC AAT CCT GAT GTG ACG       240
GTA CAT TTT GAA ATG GAT CGT ATC CAA GCC ATT CAA CAG GCG ATT GCC       288
CAG GCT AAC CCG CCG AGC GGC CGC GAA TTC                               318
```

( 2 ) INFORMATION FOR SEQ ID NO:95:

( i ) SEQUENCE CHARACTERISTICS:
        ( A ) LENGTH: 189 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU5-6

( x i ) SEQUENCE DESCRIPTION: SEQ ID NO:95:

```
GAA TTC GCG GCC GCT CGA CGG CAC AAA CTC TCC GCC CGC TAC CTG GAT        48
GAT GAT TCG ATC ACT ACG CCG AGC GCG ATG AAC TCG CCT TTC TTC ACC        96
ACC GAG TTC AAC GGC ATC TCG CGC AAC CTT CTG TTC ACC TAC ACG TGG       144
GTA GTC AAT CCG ACC ATC ACC AAC GAG CTG CGC GGC CGC GAA TTC           189
```

( 2 ) INFORMATION FOR SEQ ID NO:96:

( i ) SEQUENCE CHARACTERISTICS:
        ( A ) LENGTH: 210 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU6-2

( x i ) SEQUENCE DESCRIPTION: SEQ ID NO:96:

| GAA | TTC | GCG | GCC | GCT | CGG | GCG | GCG | AGT | TCG | AGC | AAC | GCG | GCG | AGG | CGT | 48 |
| TTA | AAT | TCA | GAA | GTG | TGC | GAT | GGG | GTT | TGG | CGT | AGG | AAA | TCG | ATC | CAG | 96 |
| AGC | GGA | GCG | TTA | AAG | AGG | AGG | CCA | TCG | ATC | CGT | CCA | AGT | GCG | GTT | TGA | 144 |
| TCG | ACG | ATC | AGA | TCA | ATA | GGA | TCA | AAA | CAA | GTC | CAA | TCA | GCG | AGT | TGT | 192 |
| GCG | AGC | GGC | CGC | GAA | TTC | | | | | | | | | | | 210 |

( 2 ) INFORMATION FOR SEQ ID NO:97:

( i ) SEQUENCE CHARACTERISTICS:
        ( A ) LENGTH: 234 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU6-4

( x i ) SEQUENCE DESCRIPTION: SEQ ID NO:97:

| GAA | TTC | GCG | GCC | GCT | CGG | GGC | GAA | GCG | GAT | CTG | TAC | TAC | AAG | ACG | GCC | 48 |
| GAC | GGC | GTG | GTA | CAT | GTG | GAA | GAG | GTC | AAG | AGC | ACG | TTT | CGG | GCA | TTG | 96 |
| AAC | CGT | AAG | TTG | GAA | AAG | GTG | AAG | AAG | GTA | GCT | GAA | GGA | GCC | AGA | GAC | 144 |
| GAT | CGA | GAG | AAG | CTG | CAA | AGA | ATC | ATG | AAG | GAT | ACG | CAG | TTG | GGG | CGG | 192 |
| TAT | GTG | AAG | TGG | GAG | CAA | GAA | GGG | GCG | AGC | GGC | CGC | GAA | TTC | | | 234 |

( 2 ) INFORMATION FOR SEQ ID NO:98:

( i ) SEQUENCE CHARACTERISTICS:
        ( A ) LENGTH: 294 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU7-8

( x i ) SEQUENCE DESCRIPTION: SEQ ID NO:98:

| GAA | TTC | GCG | GCC | GCT | CGC | GGC | CAG | TTA | CCC | GAA | GGG | GAA | CCG | CTG | CTC | 48 |
| GCG | ACG | GAT | GAA | GTT | ACC | ATC | TAC | GGC | CCG | CGT | TCC | GAT | GAG | ATC | AAA | 96 |
| TCC | GGC | AAT | GCG | CGA | ACG | CTA | ATC | AGG | CAA | CAC | ATC | GCG | CAA | GCG | CGC | 144 |
| GCC | GGG | CGC | GAT | TAC | GTC | GCG | CTG | CTC | CTC | TAT | CTC | GAA | GAG | GCA | GCA | 192 |
| GAA | CAC | GAT | GCT | TTG | GTT | CGC | GAC | ATT | CGC | CGT | CAT | GTA | CGC | GAT | CGC | 240 |
| CTG | CGC | GTG | GCG | ACC | ACC | GCT | GGT | TAC | GGT | CCG | CGC | TCG | AGC | GGC | CGC | 288 |
| GAA | TTC | | | | | | | | | | | | | | | 294 |

( 2 ) INFORMATION FOR SEQ ID NO:99:

( i ) SEQUENCE CHARACTERISTICS:

(A) LENGTH: 273 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: SCH Clone SU7-9

(xi) SEQUENCE DESCRIPTION: SEQ ID NO:99:

| | | | | | | | | | | | | | | | | |
|---|---|---|---|---|---|---|---|---|---|---|---|---|---|---|---|---|
| GAA | TTC | GCG | GCC | GCT | CGG | GCG | GAC | CGA | TGG | CCC | GAA | CGA | TGG | TCC | GGT | 48 |
| TTG | CGA | CCC | ACG | CAC | GGG | AAG | AGC | CTT | TCC | CGG | CGG | CAT | CAT | CCC | GTT | 96 |
| GAG | TCG | CCA | GAC | AAC | GGT | CGG | GCG | GAA | CTA | CCT | GAA | CGC | CTT | TCC | GCT | 144 |
| GCC | GAC | GCG | CAA | CGT | CTT | CAA | CCC | GAG | CGA | CTC | GCT | CGA | AGC | CCG | CAA | 192 |
| CTA | CTT | CAC | GCA | GCG | CGC | TAA | TCG | CGA | GAT | CAT | CAA | CAA | CTT | CGG | GCT | 240 |
| GCG | CAT | CGA | CCA | CCG | TTT | CAG | CGA | AAG | GAA | TTC | | | | | | 273 |

(2) INFORMATION FOR SEQ ID NO:100:

(i) SEQUENCE CHARACTERISTICS:
(A) LENGTH: 198 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: SCH Clone SU8-3

(xi) SEQUENCE DESCRIPTION: SEQ ID NO:100:

| | | | | | | | | | | | | | | | | |
|---|---|---|---|---|---|---|---|---|---|---|---|---|---|---|---|---|
| GAA | TTC | GCG | GCC | GCT | CGA | TGC | GTG | GTC | TAT | GAC | GAT | CAG | CAC | GGC | CCG | 48 |
| GCG | CTT | GCA | CGC | CGA | GAT | GGT | TCG | GCT | GTT | GCA | GCA | GAG | CGA | AAG | ATG | 96 |
| GTG | AGC | CTA | GCG | CGG | GTA | AAG | TCC | AAC | TCT | GCT | GCT | GCT | GCG | CGT | TTG | 144 |
| AGT | TGC | AGC | GCG | GCG | AGA | GTT | GGT | GAG | CTT | GGT | GGG | GCG | AGC | GGC | CGC | 192 |
| GAA | TTC | | | | | | | | | | | | | | | 198 |

(2) INFORMATION FOR SEQ ID NO:101:

(i) SEQUENCE CHARACTERISTICS:
(A) LENGTH: 268 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: SCH Clone SU8-4

(xi) SEQUENCE DESCRIPTION: SEQ ID NO:101:

| | | | | | | | | | | | | | | | | |
|---|---|---|---|---|---|---|---|---|---|---|---|---|---|---|---|---|
| GAA | TTC | GCG | GCC | GCT | CGA | AAA | CTC | AAC | GCA | TAC | CAG | ACT | GAA | CCG | ACC | 48 |

| | | | | | | | | | | | | | | | | |
|---|---|---|---|---|---|---|---|---|---|---|---|---|---|---|---|---|
| CAG | CCG | GCT | AAG | GCT | TGA | CCA | GAT | AAC | CCA | ATG | TTA | AAG | AAT | CCA | GCT | 96 |
| GTT | TGC | GCC | ACA | GCA | AAA | CCA | AGC | GCT | GTT | AAA | ATC | AAT | GGC | GTC | ATT | 144 |
| TGA | GTC | AAG | ACA | CCA | CCG | ATG | TCT | TGC | ATT | GAA | CCA | AAG | GCT | GAA | CCC | 192 |
| AGT | AAC | GCC | ACA | TAA | CCA | GAA | ATC | GGA | TTA | TAC | CCG | AAA | ACC | AGC | ATA | 240 |
| ATA | ACG | GCC | CCC | GAG | CGG | CCG | CGA | ATT | C | | | | | | | 268 |

( 2 ) INFORMATION FOR SEQ ID NO:102:

( i ) SEQUENCE CHARACTERISTICS:
        ( A ) LENGTH: 345 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: SCH Clone SU8-7

( x i ) SEQUENCE DESCRIPTION: SEQ ID NO:102:

| | | | | | | | | | | | | | | | | |
|---|---|---|---|---|---|---|---|---|---|---|---|---|---|---|---|---|
| GAA | TTC | GCG | GCC | GCT | CGC | CCA | ACT | AAC | CCG | CCG | CCA | CCA | TCG | CCA | TCG | 48 |
| GCC | GCA | AAA | TGT | GGC | ACC | AAG | AGA | CGC | TCC | CCA | TCC | AGC | AAA | ACC | ACC | 96 |
| CAG | TCA | GCT | TTA | AAG | GTT | GCC | TCA | CAA | GCT | AGC | GCC | CCT | TTT | TCA | AAC | 144 |
| GAA | GGC | TCC | GGC | ATA | AAA | CTT | GCT | CCC | GAA | AAA | AAC | GGA | GAA | TTA | CGG | 192 |
| GGG | AAA | AAC | GCC | CGT | GCT | GAC | GGG | CCG | TGC | TTT | TTG | CCT | GGT | AAT | ATC | 240 |
| CAC | ATA | GTC | TTG | AAA | AAA | GTG | GTC | TTC | CGA | TGC | CGC | CGC | AAA | GCG | CCG | 288 |
| CCG | AAC | TCG | AAG | CGG | AGA | TCA | AGC | GCG | CCG | AAG | AAC | TTC | TCG | AGC | GGC | 336 |
| CGC | GAA | TTC | | | | | | | | | | | | | | 345 |

( 2 ) INFORMATION FOR SEQ ID NO:103:

( i ) SEQUENCE CHARACTERISTICS:
        ( A ) LENGTH: 258 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: Clone 2DR8

( x i ) SEQUENCE DESCRIPTION: SEQ ID NO:103:

| | | | | | |
|---|---|---|---|---|---|
| GAATTCGCGG | CCGCTCGATG | TATCAAAGCT | AATTCAAATG | ACTATAGAAG | CCAAAATGGC | 60 |
| GCCCTTTGGC | TCTCACCAAA | GGGCGCTTTC | TTGTAGAAAG | AGGAACCTAT | GTCAACTTTT | 120 |
| TCCGGATTTT | ATAAAAAATC | ACGCCAAGAA | CGCATTGATA | TTCTCCAACA | GAATCGTTCC | 180 |
| CTATCCGAAG | ATAGCTTGGA | CATTCTATAC | AAAGACGAAA | ACCTTCCAGA | AGCAATTGCA | 240 |
| GCGAGCGGCC | GCGAATTC | | | | | 258 |

( 2 ) INFORMATION FOR SEQ ID NO:104:

( i ) SEQUENCE CHARACTERISTICS:

(A) LENGTH: 430 base pairs
(B) TYPE: nucleic acid
(C) STRANDEDNESS: double
(D) TOPOLOGY: linear (ii) MOLECULE TYPE: DNA (iii) HYPOTHETICAL: NO (iv) ANTI-SENSE: NO (vi) ORIGINAL SOURCE:
(C) INDIVIDUAL ISOLATE: Clone 470-20-1 extension sequence (ix) FEATURE:
(A) NAME/KEY: CDS
(B) LOCATION: 2..430

(xi) SEQUENCE DESCRIPTION: SEQ ID NO:104:

```
A GCA ACA TCA GCC ACC GTC AAC CCC AAT GAG AAA AAG CGC GTG ACG       46
  Ala Thr Ser Ala Thr Val Asn Pro Asn Glu Lys Lys Arg Val Thr
  1               5                   10                  15

CTC TTT TCA ACG CAG CAC GAC ATC TTG ACG GTA AGC TTC CTG GTC GCG     94
Leu Phe Ser Thr Gln His Asp Ile Leu Thr Val Ser Phe Leu Val Ala
                20                  25                  30

TCG CTC TGT GGA AAT AAG GCT TTT AAT ACG GAA AGA GCC ACG TTG AAG    142
Ser Leu Cys Gly Asn Lys Ala Phe Asn Thr Glu Arg Ala Thr Leu Lys
            35                  40                  45

ACA CTT TCC TCC CCT TCG GCT GTC TCG GAC TCT TGG ATG ACC TCG AAT    190
Thr Leu Ser Ser Pro Ser Ala Val Ser Asp Ser Trp Met Thr Ser Asn
        50                  55                  60

GAG TCA GAG GAC GGG GTA TCC TCC TGC GAG GAG GAC ACC GAC GGG GTC    238
Glu Ser Glu Asp Gly Val Ser Ser Cys Glu Glu Asp Thr Asp Gly Val
    65                  70                  75

TTC TCA TCT GAG CTG CTC TCA GTA ACC GAG ATA AGT GCT GGC GAT GGA    286
Phe Ser Ser Glu Leu Leu Ser Val Thr Glu Ile Ser Ala Gly Asp Gly
80                  85                  90                  95

GTA CGG GGG ATG TCT TCT CCC CAT ACA GGC ATC TCT CGG CTA CTA CCA    334
Val Arg Gly Met Ser Ser Pro His Thr Gly Ile Ser Arg Leu Leu Pro
                100                 105                 110

CAA AGA GAG GGT GTA CTG CAG TCC TCC ATG ATG ACA TCA ATG TGC GGT    382
Gln Arg Glu Gly Val Leu Gln Ser Ser Met Met Thr Ser Met Cys Gly
            115                 120                 125

TCA AGA ATC CTC GCA GCA TTC TCG ATC GCT TGG AGA GCA GCA GCC GCC    430
Ser Arg Ile Leu Ala Ala Phe Ser Ile Ala Trp Arg Ala Ala Ala Ala
        130                 135                 140
```

(2) INFORMATION FOR SEQ ID NO:105:

(i) SEQUENCE CHARACTERISTICS:
(A) LENGTH: 143 amino acids
(B) TYPE: amino acid
(D) TOPOLOGY: linear (ii) MOLECULE TYPE: protein (xi) SEQUENCE DESCRIPTION: SEQ ID NO:105:

```
Ala Thr Ser Ala Thr Val Asn Pro Asn Glu Lys Lys Arg Val Thr Leu
1               5                   10                  15

Phe Ser Thr Gln His Asp Ile Leu Thr Val Ser Phe Leu Val Ala Ser
                20                  25                  30

Leu Cys Gly Asn Lys Ala Phe Asn Thr Glu Arg Ala Thr Leu Lys Thr
            35                  40                  45

Leu Ser Pro Ser Ala Val Ser Asp Ser Trp Met Thr Ser Asn Glu
        50                  55                  60
```

| | | | | | | | | | | | | | | | |
|---|---|---|---|---|---|---|---|---|---|---|---|---|---|---|---|
| Ser | Glu | Asp | Gly | Val | Ser | Ser | Cys | Glu | Glu | Asp | Thr | Asp | Gly | Val | Phe |
| 65 | | | | | 70 | | | | 75 | | | | | | 80 |
| Ser | Ser | Glu | Leu | Leu | Ser | Val | Thr | Glu | Ile | Ser | Ala | Gly | Asp | Gly | Val |
| | | | | 85 | | | | | 90 | | | | | 95 | |
| Arg | Gly | Met | Ser | Ser | Pro | His | Thr | Gly | Ile | Ser | Arg | Leu | Leu | Pro | Gln |
| | | | 100 | | | | | 105 | | | | | 110 | | |
| Arg | Glu | Gly | Val | Leu | Gln | Ser | Ser | Met | Met | Thr | Ser | Met | Cys | Gly | Ser |
| | | 115 | | | | | 120 | | | | | 125 | | | |
| Arg | Ile | Leu | Ala | Ala | Phe | Ser | Ile | Ala | Trp | Arg | Ala | Ala | Ala | Ala | |
| | 130 | | | | | 135 | | | | | 140 | | | | |

(2) INFORMATION FOR SEQ ID NO:106:

(i) SEQUENCE CHARACTERISTICS:
        (A) LENGTH: 237 base pairs
        (B) TYPE: nucleic acid
        (C) STRANDEDNESS: double
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: PNF2161 Clone 470-20-1

(xi) SEQUENCE DESCRIPTION: SEQ ID NO:106:

```
GAATTCGCGG  CCGCTCGGGC  TGTCTCGGAC  TCTTGGATGA  CCTCGAATGA  GTCAGAGGAC        60
GGGGTATCCT  CCTGCGAGGA  GGACACCGAC  GGGGTCTTCT  CATCTGAGCT  GCTCTCAGTA       120
ACCGAGATAA  GTGCTGGCGA  TGGAGTACGG  GGGATGTCTT  CTCCCCATAC  AGGCATCTCT       180
CGGCTACTAC  CACAAAGAGA  GGGTGTACTG  CAGTCCTCCA  CGAGCGGCCG  CGAATTC         237
```